United States Patent
Asaki et al.

(10) Patent No.: US 7,205,302 B2
(45) Date of Patent: Apr. 17, 2007

(54) HETEROCYCLIC COMPOUND DERIVATIVES AND MEDICINES

(75) Inventors: Tetsuo Asaki, Kyoto (JP); Taisuke Hamamoto, Osaka (JP); Keiichi Kuwano, Osaka (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 344 days.

(21) Appl. No.: 10/476,196

(22) PCT Filed: Apr. 25, 2002

(86) PCT No.: PCT/JP02/04118

§ 371 (c)(1),
(2), (4) Date: Oct. 23, 2003

(87) PCT Pub. No.: WO02/088084

PCT Pub. Date: Nov. 7, 2002

(65) Prior Publication Data

US 2004/0102436 A1    May 27, 2004

(30) Foreign Application Priority Data

Apr. 26, 2001   (JP) .............................. 2001-129765

(51) Int. Cl.
| | | |
|---|---|---|
| C97D 241/18 | (2006.01) | |
| C07D 241/20 | (2006.01) | |
| A61K 31/4966 | (2006.01) | |
| A61P 7/02 | (2006.01) | |
| A61P 9/08 | (2006.01) | |
| A61P 9/10 | (2006.01) | |
| A61P 9/12 | (2006.01) | |
| C07D 253/065 | (2006.01) | |
| C07D 239/42 | (2006.01) | |
| C07D 213/74 | (2006.01) | |
| A61K 31/53 | (2006.01) | |
| A61K 31/505 | (2006.01) | |
| A61K 31/4488 | (2006.01) | |

(52) U.S. Cl. ................. 514/252.1; 544/336; 544/408; 544/180; 544/216; 544/297; 544/298; 514/241; 514/245; 514/269; 514/272; 514/345; 514/352; 546/300; 546/301

(58) Field of Classification Search ................ 544/336, 544/408; 514/252.1
See application file for complete search history.

(56) References Cited

FOREIGN PATENT DOCUMENTS

| EP | 0 088 593 A2 | 9/1983 |
|---|---|---|
| GB | 1 604 084 | 12/1981 |
| JP | 7-33752 A1 | 2/1992 |
| JP | 5-208961 A1 | 8/1993 |
| JP | 5-508845 A1 | 12/1993 |
| WO | WO-92/01675 A2 | 2/1992 |
| WO | WO-92/02513 A1 | 2/1992 |

OTHER PUBLICATIONS

Meanwell, Nicholas A. et al., Nonprostanoid prostacyclin mimetics. 3. Structural variations of the diphenyl heterocycle moiety, J. Med. Chem., 1992, vol. 35, No. 19, pp. 3498 to 3512; particularly, compound Nos. 13aw, 13ax, 13aaa on table II.

Konno, Shoetsu et al., Studies on as-triazine derivatives. XIX. Synthesis of 2, 3-diarylpyrazine and 2, 3-diarypyridine derivatives as blood platelet aggregation inhibitors. Yakugaku Zasshi, 1993, vol. 113, No. 1, pp. 40 to 52; particularly, tables III, IV.

Bhalla, M. et al., Synthesis and pharmacological evaluation of 1, 2, 4-triazine and its congeners, Boll. Chim. Farm., 1995, vol. 134, No. 1, pp. 9 to 15; compounds on formulas IV, V of Fig. 1.

*Primary Examiner*—Venkataraman Balasubramanian
(74) *Attorney, Agent, or Firm*—Darby & Darby

(57) ABSTRACT

The present invention provides a compound which is useful as a $PGI_2$ receptor agonist, and a pharmaceutical composition.

The present invention is directed to a pharmaceutical composition comprising a compound represented by the following formula [1]:

$$R^1\text{-}Y\text{=}Z\text{-}...\text{-}R^2\text{-}N\text{-}A\text{-}D\text{-}E\text{-}G\text{-}C(R^3)(R^4)\text{-}Q \quad (1)$$

($R^1$ and $R^2$ are the same or different and each represents optionally substituted aryl, Y represents N or CH, Z represents N or CH, A represents NH, $NR^5$, O, S, or ethylene, $R^5$ represents alkyl, D represents alkylene or alkenylene, E represents phenylene or single bond, G represents O, S, or $CH_2$, $R^3$ and $R^4$ are the same or different and each represents hydrogen or alkyl, Q represents carboxy, alkoxycarbonyl, tetrazolyl, carbamoyl, or N-(alkylsulfonyl)carbamoyl), or a pharmaceutically acceptable salt thereof as an active ingredient.

15 Claims, No Drawings

HETEROCYCLIC COMPOUND DERIVATIVES AND MEDICINES

TECHNICAL FIELD

The present invention relates to a novel heterocyclic derivative which is useful as a medicine, or a salt thereof, and a $PGI_2$ receptor agonist containing the same as an active ingredient.

BACKGROUND ART

Prostaglandin $I_2$ ($PGI_2$) is produced from arachidonic acid via prostaglandin $H_2$ ($PGH_2$) in the living body and has various potent pharmacological effects such as inhibition of platelet aggregation, vasodilation, inhibition of lipid deposition, and inhibition of leucocyte activation. It is therefore considered that $PGI_2$ is effective for treatment of peripheral vascular diseases (for example, arteriosclerosis obliterans, intermittent claudication, peripheral arterial embolism, vibration disease, and Raynaud's disease), systemic lupus erythematosus, reocclusion or restenosis after percutaneous transluminal coronary angioplasty (PTCA), arteriosclerosis, thrombosis, diabetic neuropathy, diabetic nephropathy, hypertension, ischemic diseases (for example, cerebral infarction and myocardial infarction), transient ischemic attack and glomerulonephritis, or acceleration of angiogenesis in peripheral blood vessel reconstruction technique or angiogenesis therapy.

However, $PGI_2$ is not suited for use as a medicine because it is chemically unstable and has very short biological half-life, and also has such a problem that side effect is likely to arise because it is difficult to separate the desired effect from the other effect. For the purpose of persistence of drug efficacy, relief of side effect and improvement of compliance, long acting preparations of prostaglandins have been researched and developed. However, satisfactory results have never been achieved.

Under these circumstances, it is expected that a $PGI_2$ receptor agonist, which is non-prostanoid and has excellent affinity to $PGI_2$ receptor and chemical stability, exerts excellent therapeutic effect a medicine as compared with conventional $PGI_2$ preparations, and thus it has intensively been researched and developed.

For example, it has been known that imidazole derivatives (Br. J. Pharmcol., 102, 251 (1991)), oxazole derivatives (J. Med. Chem., 35, 3498 (1992), J. Med. Chem., 36, 3884 (1993)), pyrazole derivatives (Folia Phermacol. Jp., 106, 181 (1995), Bioorg. Med. Chem. Lett., 5, 1071 (1995), Bioorg. Med. Chem. Lett., 5, 1083 (1995)), pyrazinone derivatives (Bioorg. Med. Chem. Lett., 10, 2787 (2000)) and oxime derivatives (Folia Phermacol. Jp., 106, 181 (1995), Bioorg. Med. Chem. Lett., 5, 1071 (1995), Bioorg. Med. Chem. Lett., 5, 1083 (1995)) have $PGI_2$ receptor agonistic activity.

Also it is known that 2,3-diphenylpyrazine derivatives (Japanese Unexamined Patent Publication No. Hei-7-33752) have a herbicidal effect, 2,3-diphenylpyridine derivatives and 5,6-diphenylpyrimidine derivatives (WO92/01675) have a leukotriene $B_4$ antagonism and 2,3-diphenylpyridine derivatives (WO96/18616) have a nitric oxide synthesis inhibitory effect. However, it is not known that these compounds have a $PGI_2$ receptor agonistic activity.

DISCLOSURE OF THE INVENTION

An object of the present invention is to provide a novel $PGI_2$ receptor agonist and a novel heterocyclic derivative.

To achieve the above object, the present inventors have synthesized various compounds during the process of study and found that heterocyclic derivatives represented by the following general formula (1) (hereinafter also referred to as heterocyclic derivatives (1)) have excellent $PGI_2$ receptor agonistic activity, and thus the present invention has been completed.

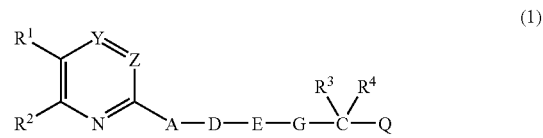

(1)

wherein $R^1$ and $R^2$ are the same or different and each represents an optionally substituted aryl, and the substituents are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro, Y represents N, N→O or $CR^5$, Z represents N or $CR^6$; and $R^5$ and $R^6$ are the same or different and each represents hydrogen, alkyl or halogen, A represents $NR^7$, O, S, SO, $SO_2$, or ethylene, and $R^7$ represents hydrogen, alkyl, alkenyl or cycloalkyl, D represents alkylene or alkenylene which are optionally substituted with hydroxy, or A and D are combined with each other to form a divalent group represented by the following formula (2):

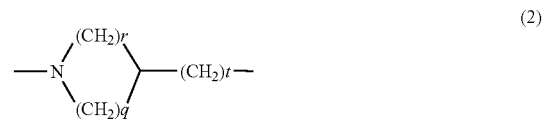

(2)

r represents an integer of 0 to 2, q represents an integer of 2 to 3, and t represents an integer of 0 to 4, E represents phenylene or single bond, or D and E are combined with each other to form a divalent group represented by the following formula (3):

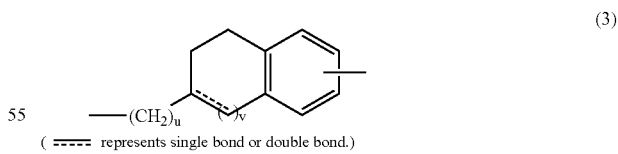

(3)

( ===== represents single bond or double bond.)

u represents an integer of 0 to 2, and v represents 0 or 1,

G represents O, S, SO, $SO_2$, or $C(R^8)(R^9)$, and $R^8$ and $R^9$ are the same or different and each represents hydrogen or alkyl, $R^3$ and $R^4$ are the same or different and each represents hydrogen or alkyl, Q represents carboxy, alkoxycarbonyl, tetrazolyl, carbamoyl, monoalkylcarbamoyl, dialkylcarbamoyl, or a group represented by the following formula (22):

$R^{10}$ represents amino, monoalkylamino, dialkylamino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro.

Among the heterocyclic derivatives represented by the formula (1), preferable compounds are the following compounds wherein $R^1$ and $R^2$ are the same or different and each represents optionally substituted phenyl, and the substituents are the same or different and 1 to 3 substituents are selected from the group consisting of halogen, alkyl and alkoxy, Y and Z correspond to either of the following cases (1) and (2):
(1) Y is N or CH, and Z is N or CH, and
(2) Y is N→O, and Z is CH, A represents $NR^7$, and $R^7$ represents hydrogen, alkyl, or cycloalkyl, D represents alkylene or alkenylene, E represents single bond, G represents O, S, SO, $SO_2$, or $C(R^8)(R^9)$, and $R^8$ and $R^9$ each represents hydrogen, $R^3$ and $R^4$ are the same or different and each represents hydrogen or alkyl, and Q represents carboxy, alkoxycarbonyl, tetrazolyl, or a group represented by the formula (22), and $R^{10}$ represents amino, monoalkylamino, dialkylamino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro.

Among the heterocyclic derivatives represented by the formula (1), more preferable compounds are the following compounds wherein $R^1$ and $R^2$ are the same or different and each represents optionally substituted phenyl, and the substituents are the same or different and 1 to 3 substituents are selected from the group consisting of halogen, alkyl and alkoxy, Y and Z correspond to either of the following cases (1) and (2):
(1) Y is N, and Z is CH, and
(2) Y is CH, and Z is N or CH, A represents $NR^7$, and $R^7$ represents hydrogen or alkyl, D represents alkylene, E represents single bond, G represents O, $R^3$ and $R^4$ are the same or different and each represents hydrogen or alkyl, Q represents carboxy, tetrazolyl, or a group represented by the formula (22), and $R^{10}$ represents amino, mono alkylamino, dialkylamino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro.

Among the heterocyclic derivatives represented by the formula (1), particularly preferable compounds are the following compounds wherein $R^1$ and $R^2$ are the same or different and each represents optionally substituted phenyl, and the substituents are the same or different and 1 to 3 substituents are selected from the group consisting of halogen, alkyl and alkoxy, Y represents N, and Z represents CH, A represents $NR^7$, and $R^7$ represents alkyl, D represents alkylene, E represents single bond, G represents O, $R^3$ and $R^4$ are the same or different and each represents hydrogen or alkyl, and Q represents carboxy or a group represented by the formula (22), and $R^{10}$ represents amino monoalkylamino, dialkylamino, hydroxy, optionally substituted alkyl, optionally substituted aryl, optionally substituted aryloxy or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro.

Specific examples of preferable compounds among the heterocyclic derivatives represented by the formula (1) include the following compounds (1) to (32):

(1) 2-{4-[N-(5,6-di-p-tolylpyrazin-2-yl)-N-methylamino]butyloxy}acetic acid,
(2) 2-{4-[N-(5,6-diphenylpyrazin-2-yl)-N-methylamino]butyloxy}acetic acid,
(3) 2-{4-[N-(5,6-diphenylpyrazin-2-yl)-N-isopropylamino]butyloxy}acetic acid,
(4) 2-{4-[N-(5,6-di-p-tolylpyrazin-2-yl)-N-isopropylamino]butyloxy}acetic acid,
(5) 2,3-diphenyl-5-{N-[4-(carboxymethoxy)butyl]-N-methylamino}pyrazine 1-oxide,
(6) 2-{4-[N-(4,5-di-p-tolylpyrimidin-2-yl)-N-methylamino]butyloxy}acetic acid,
(7) 7-[N-(5,6-diphenylpyrazin-2-yl)-N-methylamino]heptanoic acid,
(8) 2-{4-[N-(5,6-diphenylpyrazin-2-yl)-N-isopropylamino]butylthio}acetic acid,
(9) 2-{4-[N-(5,6-diphenylpyrazin-2-yl)-N-methylamino]-(Z)-2-buten-1-yloxy}acetic acid,
(10) 2-{4-[N-(5,6-di-p-tolyl-1,2,4-triazin-3-yl)-N-isopropylamino]butyloxy}acetic acid,
(11) 2-{4-[N-(5,6-diphenylpyrazin-2-yl)-N-ethylamino]butyloxy}acetic acid,
(12) 2-{4-[N-(2,3-diphenylpyridin-6-yl)-N-methylamino]butyloxy}acetic acid,
(13) 2-{4-[N-(5,6-diphenylpyrazin-2-yl)-N-isopropylamino]butylsulfinyl}acetic acid,
(14) 2-{4-[N-(5,6-diphenyl-1,2,4-triazin-3-yl)-N-methylamino]butyloxy}acetic acid,
(15) 2-{4-[N-(4,5-diphenylpyrimidin-2-yl)-N-methylamino]butyloxy}acetic acid,
(16) 2-{4-[N-(5,6-diphenylpyrazin-2-yl)-N-isopropylamino]butyloxy}-N-(p-toluenesulfonyl)acetamide,
(17) 2-{4-[N-(5,6-diphenylpyrazin-2-yl)-N-isopropylamino]butyloxy}-N-(isopropylsulfonyl)acetamide,

(18) 2-{4-[N-(5,6-diphenylpyrazin-2-yl)-N-isopropylamino]butyloxy}-N-(trifluoromethanesulfonyl)acetamide,
(19) 2-{4-[N-(5,6-diphenylpyrazin-2-yl)-N-isopropylamino]butyloxy}-N-(o-toluenesulfonyl)acetamide,
(20) N-(benzenesulfonyl)-2-{4-[N-(5,6-diphenylpyrazin-2-yl)-N-isopropylamino]butyloxy}acetamide,
(21) N-(4-chlorobenzenesulfonyl)-2-{4-[N-(5,6-diphenylpyrazin-2-yl)-N-isopropylamino]butyloxy}acetamide,
(22) 2-{4-[N-(5,6-diphenylpyrazin-2-yl)-N-isopropylamino]butyloxy}-N-(4-methoxybenzenesulfonyl)acetamide,
(23) 2-{4-[N-(5,6-diphenylpyrazin-2-yl)-N-isopropylamino]butyloxy}-N-(4-fluorobenzenesulfonyl)acetamide,
(24) 2-{4-[N-(5,6-diphenylpyrazin-2-yl)-N-isopropylamino]butyloxy}-N-(2-thiophenesulfonyl)acetamide,
(25) N-(aminosulfonyl)-2-{4-[N-(5,6-diphenylpyrazin-2-yl)-N-isopropylamino]butyloxy}acetamide,
(26) N-(N,N-dimethylaminosulfonyl)-2-{4-[N-(5,6-diphenylpyrazin-2-yl)-N-isopropylamino]butyloxy}acetamide,
(27) 2-{4-[N-(5,6-diphenylpyrazin-2-yl)-N-isopropylamino]butyloxy}-N-(morpholin-4-ylsulfonyl)acetamide,
(28) 2-{4-[N-(5,6-diphenylpyrazin-2-yl)-N-isopropylamino]butyloxy}-N-(pyrrolidin-1-ylsulfonyl)acetamide,
(29) N-[2-{4-[N-(5,6-diphenylpyrazin-2-yl)-N-isopropylamino]butyloxy}acetyl]sulfamic acid phenyl ester,
(30) N-[2-{4-[N-(5,6-diphenylpyrazin-2-yl)-N-isopropylamino]butyloxy}acetyl]sulfamic acid,
(31) N-[2-{4-[N-(5,6-diphenylpyrazin-2-yl)-N-isopropylamino]butyloxy}acetyl]sulfamic acid sodium salt, and
(32) 2-{4-[N-(5,6-diphenylpyrazin-2-yl)-N-isopropylamino]butyloxy}-N-(methylsulfonyl)acetamide.

Heterocyclic derivatives represented by the following general formula (1z) wherein substituents correspond to any one of the following cases (I) to (V) (hereinafter also referred to as heterocyclic derivatives (1z)) are novel compounds which have never been described in documents.

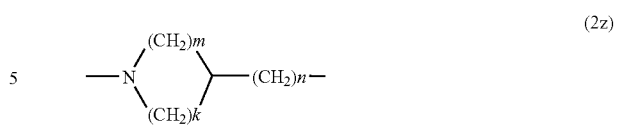

(I)
$R^{91}$ and $R^{92}$ are the same or different and each represents optionally substituted aryl, and the substituents are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro, $Y^9$ represents N or N→O, $Z^9$ represents N or $CR^{96}$, and $R^{96}$ represents hydrogen, alkyl, or halogen, $A^9$ represents $NR^{97}$, O, S, SO, $SO_2$, or ethylene, and $R^{97}$ represents hydrogen, alkyl, alkenyl, or cycloalkyl $D^9$ represents alkylene or alkenylene which are optionally substituted with hydroxy, or $A^9$ and $D^9$ are combined with each other to form a divalent group represented by the following formula (2z):

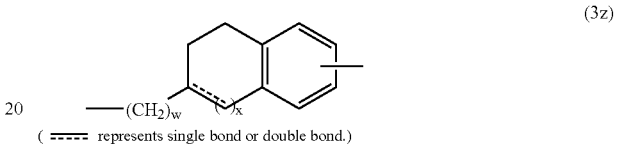

m represents an integer of 0 to 2, k represents an integer of 2 to 3, and n represents an integer of 0 to 4, $E^9$ represents phenylene or single bond, or $D^9$ and $E^9$ are combined with each other to form a divalent group represented by the following formula (3z):

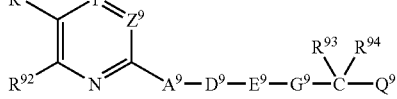

( ===== represents single bond or double bond.)

w represents an integer of 0 to 2, and x represents 0 or 1, $G^9$ represents O, S, SO, $SO_2$, or $C(R^{98})(R^{99})$, and $R^{98}$ and $R^{99}$ are the same or different and each represents hydrogen or alkyl, $R^{93}$ and $R^{94}$ are the same or different and each represents hydrogen or alkyl, $Q^9$ represents carboxy, alkoxycarbonyl, tetrazolyl, carbamoyl, monoalkylcarbamoyl, dialkylcarbamoyl, or a group represented by the

following formula (22z):

$R^{910}$ represents amino, monoalkylamino, dialkylamino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro;

(II)
$R^{91}$ and $R^{92}$ are the same or different and each represents optionally substituted aryl, and the substituents are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro, $Y^9$ represents $CR^{95}$, $Z^9$ represents N or $CR^{96}$, and $R^{95}$ and $R^{96}$ are the same or different and each represents hydrogen, alkyl, or halogen, $A^9$ represents SO or $SO_2$, $D^9$ represents alkylene or alkenylene which are optionally substituted with hydroxy, or $A^9$ and $D^9$ are combined with each other to form a divalent group represented by the following formula (2z):

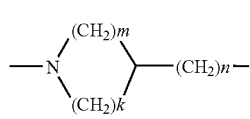
(2z)

m represents an integer of 0 to 2, k represents an integer of 2 to 3, and n represents an integer of 0 to 4, $E^9$ represents phenylene or single bond, or $D^9$ and $E^9$ are combined with each other to form a divalent group represented by the following formula (3z):

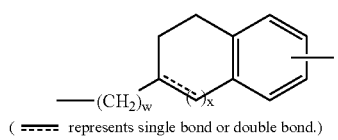
(3z)

(==== represents single bond or double bond.)

w represents an integer of 0 to 2, and x represents 0 or 1, $G^9$ represents O, S, SO, $SO_2$, or $C(R^{98})(R^{99})$, and $R^{98}$ and $R^{99}$ are the same or different and each represents hydrogen or alkyl, $R^{93}$ and $R^{94}$ are the same or different and each represents hydrogen or alkyl, $Q^9$ represents carboxy, alkoxycarbonyl, tetrazolyl, carbamoyl, monoalkylcarbamoyl, dialkylcarbamoyl, or a group represented by the following formula (22z):

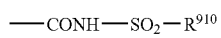
(22z)

$R^{910}$ represents amino, monoalkylamino, dialkylamino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro;

(III)

$R^{91}$ and $R^{92}$ are the same or different and each represents optionally substituted aryl, and the substituents are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro, $Y^9$ represents $CR^{95}$, $Z^9$ represents N or $CR^{96}$, and $R^{95}$ and $R^{96}$ are the same or different and each represents hydrogen, alkyl, or halogen, $A^9$ represents $NR^{97}$, O, S, or ethylene, and $R^{97}$ represents hydrogen, alkyl, alkenyl, or cycloalkyl, $D^9$ represents alkenylene, or $A^9$ and $D^9$ are combined with each other to form a divalent group represented by the following formula (2z):

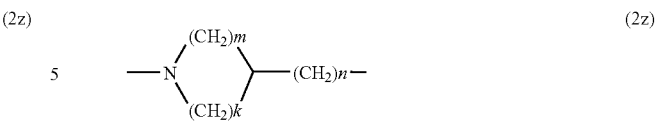
(2z)

m represents an integer of 0 to 2, k represents an integer of 2 to 3, and n represents an integer of 0 to 4, $E^9$ represents phenylene or single bond, or $D^9$ and $E^9$ are combined with each other to form a divalent group represented by the following formula (3z):

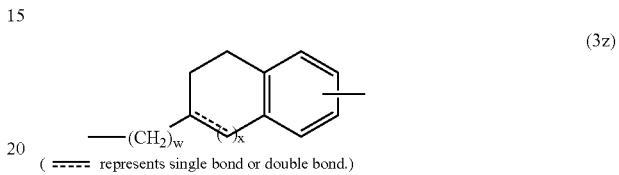
(3z)

(==== represents single bond or double bond.)

w represents an integer of 0 to 2, and x represents 0 or 1, $G^9$ represents O, S, SO, $SO_2$ or $C(R^{98})(R^{99})$, and $R^{98}$, $R^{99}$ are the same or different and each represents hydrogen or alkyl, $R^{93}$ and $R^{94}$ are the same or different and each represents hydrogen or alkyl, $Q^9$ represents carboxy, alkoxycarbonyl, tetrazolyl, carbamoyl, monoalkylcarbamoyl, dialkylcarbamoyl, or a group represented by the following formula (22z):

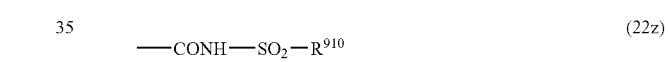
(22z)

$R^{910}$ represents amino, monoalkylamino, dialkylamino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro;

(IV)

$R^{91}$ and $R^{92}$ are the same or different and each represents optionally substituted aryl, and the substituents are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro, $Y^9$ represents $CR^{95}$, $Z^9$ represents N or $CR^{96}$, and $R^{95}$ and $R^{96}$ are the same or different and each represents hydrogen, alkyl, or halogen, $A^9$ represents $NR^{97}$, O, S, or ethylene, and $R^{97}$ represents hydrogen, alkyl, alkenyl, or cycloalkyl, $D^9$ represents alkylene which is optionally substituted with hydroxy, $E^9$ represents phenylene, $G^9$ represents O, S, SO, $SO_2$, or $C(R^{98})(R^{99})$, and $R^{98}$ and $R^{99}$ are the same or different and each represents hydrogen or alkyl, $R^{93}$ and $R^{94}$ are the same or different and each represents hydrogen or alkyl, $Q^9$ represents carboxy, alkoxycarbonyl, tetrazolyl, carbamoyl, monoalkylcarbamoyl, dialkylcarbamoyl, or a group represented by the following formula (22z):

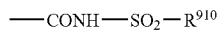
(22z)
—CONH—SO$_2$—R$^{910}$ $R^{910}$ represents amino, monoalkylamino, dialkylamino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro; and (V)
$R^{91}$ and $R^{92}$ are the same or different and each represents optionally substituted phenyl, and the substituents are the same or different and 1 to 3 substituents are selected from the group consisting of halogen, alkyl, haloalkyl, arylalkyl, alkoxy, alkylthio, alkoxyalkyl, hydroxy, amino, monoalkylamino, dialkylamino, carboxy, cyano and nitro, $Y^9$ represents CR$^{95}$, $Z^9$ represents N or CR$^{96}$, and $R^{95}$ and $R^{96}$ each represents hydrogen, $A^9$ represents NR$^{97}$, and $R^{97}$ represents hydrogen, alkyl, alkenyl, or cycloalkyl, $D^9$ represents alkylene which is optionally substituted with hydroxy, $E^9$ represents single bond, $G^9$ represents O, $R^{93}$ and $R^{94}$ are the same or different and each represents hydrogen or alkyl, $Q^9$ represents carboxy, alkoxycarbonyl, tetrazolyl, carbamoyl, monoalkylcarbamoyl, dialkylcarbamoyl, or a group represented by the following formula (22z):

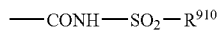
(22z)
—CONH—SO$_2$—R$^{910}$ and $R^{910}$ represents amino, monoalkylamino, dialkylamino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro.

Among novel heterocyclic derivatives (1z) described above, preferable compounds are the following compounds wherein substituents correspond to any one of the following cases (i) to (iii):

(i)
$R^{91}$ and $R^{92}$ are the same or different and each represents optionally substituted phenyl, and the substituents are the same or different and 1 to 3 substituents are selected from the group consisting of halogen, alkyl and alkoxy, $Y^9$ and $Z^9$ correspond to either of the following cases (1) and (2):

(1) $Y^9$ is N, and $Z^9$ is N or CH, and (2) $Y^9$ is N→O, and $Z^9$ is CH, $A^9$ represents NR$^{97}$, and $R^{97}$ represents hydrogen, alkyl, or cycloalkyl, $D^9$ represents alkylene, $E^9$ represents single bond, $G^9$ represents O, S, SO, SO$_2$, or C(R$^{98}$)(R$^{99}$), and $R^{98}$ and $R^{99}$ each represents hydrogen, $R^{93}$ and $R^{94}$ are the same or different and each represents hydrogen or alkyl, and $Q^9$ represents carboxy, alkoxycarbonyl, tetrazolyl, or a group represented by the formula (22z), $R^{910}$ represents amino, monoalkylamino, dialkylamino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro;

(ii)
$R^{91}$ and $R^{92}$ are the same or different and each represents optionally substituted phenyl, and the substituents are the same or different and 1 to 3 substituents are selected from the group consisting of halogen, alkyl and alkoxy, $Y^9$ represents CH, and $Z^9$ represents N or CH, $A^9$ represents NR$^{97}$, and $R^{97}$ represents hydrogen, alkyl, or cycloalkyl, $D^9$ represents alkylene, $E^9$ represents single bond, $G^9$ represents O, $R^{93}$ and $R^{94}$ are the same or different and each represents hydrogen or alkyl, $Q^9$ represents carboxy, alkoxycarbonyl, tetrazolyl, or a group represented by the formula (22z), $R^{910}$ represents amino, monoalkylamino, dialkylamino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro; and (iii)
$R^{91}$ and $R^{92}$ are the same or different and each represents optionally substituted phenyl, and the substituents are the same or different and 1 to 3 substituents are selected from the group consisting of halogen, alkyl and alkoxy, $Y^9$ and $Z^9$ correspond to either of the following cases (1) and (2):

(1) $Y^9$ is N or CH, and $Z^9$ is N or CH, and (2) $Y^9$ is N→O, and $Z^9$ is CH, $A^9$ represents NR$^{97}$, and $R^{97}$ represents hydrogen, alkyl, or cycloalkyl, $D^9$ represents alkenylene, $E^9$ represents single bond, $G^9$ represents O, S, SO, SO$_2$, or C(R$^{98}$)(R$^{99}$), and $R^{98}$ and $R^{99}$ each represents hydrogen, $R^{93}$ and $R^{94}$ are the same or different and each represents hydrogen or alkyl, $Q^9$ represents carboxy, alkoxycarbonyl, tetrazolyl, or a group represented by the formula (22z), $R^{910}$ represents amino, monoalkylamino, dialkylamino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro.

Among novel heterocyclic derivatives (1z) described above, more preferable compounds are the following compounds wherein $R^{91}$ and $R^{92}$ are the same or different and each represents optionally substituted phenyl, and the substituents are the same or different and 1 to 3 substituents are selected from the group consisting of halogen, alkyl and alkoxy, $Y^9$ and $Z^9$ correspond to either of the following cases (1) and (2):

(1) $Y^9$ is N, and $Z^9$ is CH,
(2) $Y^9$ is CH, and $Z^9$ is N or CH,
$A^9$ represents $NR^{97}$, and $R^{97}$ represents hydrogen or alkyl,
$D^9$ represents alkylene,
$E^9$ represents single bond,
$G^9$ represents O,
$R^{93}$ and $R^{94}$ are the same or different and each represents hydrogen or alkyl,
$Q^9$ represents carboxy, tetrazolyl, or a group represented by the formula (22z), $R^{910}$ represents amino, monoalkylamino, dialkylamino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro.

Among novel heterocyclic derivatives (1z) described above, particularly preferable compounds are the following compounds wherein $R^{91}$ and $R^{92}$ are the same or different and each represents optionally substituted phenyl, and the substituents are the same or different and 1 to 3 substituents are selected from the group consisting of halogen, alkyl and alkoxy, $Y^9$ represents N, and $Z^9$ represents CH,
$A^9$ represents $NR^{97}$, and $R^{97}$ represents alkyl,
$D^9$ represents alkylene,
$E^9$ represents single bond,
$G^9$ represents O,
$R^{93}$ and $R^{94}$ are the same or different and each represents hydrogen or alkyl,
$Q^9$ represents carboxy or a group represented by the formula (22z), $R^{910}$ represents amino, monoalkylamino, dialkylamino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro.

Specific examples of preferable compounds among novel heterocyclic derivatives (1z) described above include the following compounds (1) to (32):

(1) 2-{4-[N-(5,6-di-p-tolylpyrazin-2-yl)-N-methylamino]butyloxy}acetic acid,
(2) 2-{4-[N-(5,6-diphenylpyrazin-2-yl)-N-methylamino]butyloxy}acetic acid,
(3) 2-{4-[N-(5,6-diphenylpyrazin-2-yl)-N-isopropylamino]butyloxy}acetic acid,
(4) 2-{4-[N-(5,6-di-p-tolylpyrazin-2-yl)-N-isopropylamino]butyloxy}acetic acid,
(5) 2,3-diphenyl-5-{N-[4-(carboxymethoxy)butyl]-N-methylamino}pyrazine 1-oxide,
(6) 2-{4-[N-(4,5-di-p-tolylpyrimidin-2-yl)-N-methylamino]butyloxy}acetic acid,
(7) 7-[N-(5,6-diphenylpyrazin-2-yl)-N-methylamino]heptanoic acid,
(8) 2-{4-[N-(5,6-diphenylpyrazin-2-yl)-N-isopropylamino]butylthio}acetic acid,
(9) 2-{4-[N-(5,6-diphenylpyrazin-2-yl)-N-methylamino]-(Z)-2-buten-1-yloxy}acetic acid,
(10) 2-{4-[N-(5,6-di-p-tolyl-1,2,4-triazin-3-yl)-N-isopropylamino]butyloxy}acetic acid,
(11) 2-{4-[N-(5,6-diphenylpyrazin-2-yl)-N-ethylamino]butyloxy}acetic acid,
(12) 2-{4-[N-(2,3-diphenylpyridin-6-yl)-N-methylamino]butyloxy}acetic acid,
(13) 2-{4-[N-(5,6-diphenylpyrazin-2-yl)-N-isopropylamino]butylsulfinyl}acetic acid,
(14) 2-{4-[N-(5,6-diphenyl-1,2,4-triazin-3-yl)-N-methylamino]butyloxy}acetic acid,
(15) 2-{4-[N-(4,5-diphenylpyrimidin-2-yl)-N-methylamino]butyloxy}acetic acid,
(16) 2-{4-[N-(5,6-diphenylpyrazin-2-yl)-N-isopropylamino]butyloxy}-N-(p-toluenesulfonyl)acetamide,
(17) 2-{4-[N-(5,6-diphenylpyrazin-2-yl)-N-isopropylamino]butyloxy}-N-(isopropylsulfonyl)acetamide,
(18) 2-{4-[N-(5,6-diphenylpyrazin-2-yl)-N-isopropylamino]butyloxy}-N-(trifluoromethanesulfonyl)acetamide,
(19) 2-{4-[N-(5,6-diphenylpyrazin-2-yl)-N-isopropylamino]butyloxy}-N-(o-toluenesulfonyl)acetamide,
(20) N-(benzenesulfonyl)-2-{4-[N-(5,6-diphenylpyrazin-2-yl)-N-isopropylamino]butyloxy}acetamide,
(21) N-(4-chlorobenzenesulfonyl)-2-{4-[N-(5,6-diphenylpyrazin-2-yl)-N-isopropylamino]butyloxy}acetamide,
(22) 2-{4-[N-(5,6-diphenylpyrazin-2-yl)-N-isopropylamino]butyloxy}-N-(4-methoxybenzenesulfonyl)acetamide,
(23) 2-{4-[N-(5,6-diphenylpyrazin-2-yl)-N-isopropylamino]butyloxy}-N-(4-fluorobenzenesulfonyl)acetamide,
(24) 2-{4-[N-(5,6-diphenylpyrazin-2-yl)-N-isopropylamino]butyloxy}-N-(2-thiophenesulfonyl)acetamide,
(25) N-(aminosulfonyl)-2-{4-[N-(5,6-diphenylpyrazin-2-yl)-N-isopropylamino]butyloxy}acetamide,
(26) N-(N,N-dimethylaminosulfonyl)-2-{4-[N-(5,6-diphenylpyrazin-2-yl)-N-isopropylamino]butyloxy}acetamide,
(27) 2-{4-[N-(5,6-diphenylpyrazin-2-yl)-N-isopropylamino]butyloxy}-N-(morpholin-4-ylsulfonyl)acetamide,
(28) 2-{4-[N-(5,6-diphenylpyrazin-2-yl)-N-isopropylamino]butyloxy}-N-(pyrrolidin-1-ylsulfonyl)acetamide,
(29) N-[2-{4-[N-(5,6-diphenylpyrazin-2-yl)-N-isopropylamino]butyloxy}acetyl]sulfamic acid phenyl ester,
(30) N-[2-{4-[N-(5,6-diphenylpyrazin-2-yl)-N-isopropylamino]butyloxy}acetyl]sulfamic acid,
(31) N-[2-{4-[N-(5,6-diphenylpyrazin-2-yl)-N-isopropylamino]butyloxy}acetyl]sulfamic acid sodium salt, and
(32) 2-{4-[N-(5,6-diphenylpyrazin-2-yl)-N-isopropylamino]butyloxy}-N-(methylsulfonyl)acetamide.

The present invention will be described in detail below.

Examples of "alkyl" include a straight or branched alkyl having 1 to 6 carbon atoms, for example, methyl, ethyl, n-propyl, isopropyl, n-butyl, isobutyl, sec-butyl, tert-butyl, n-pentyl, isopentyl, n-hexyl, and isohexyl. Particularly, alkyl having 1 to 4 carbon atoms is preferable.

Examples of the alkyl moiety of "haloalkyl", "arylalkyl", "alkylthio", "alkoxyalkyl", "alkylsulfonyl", "monoalkylamino", "dialkylamino", "monoalkylcarbazoyl" and "dialkylcarbamoyl" include alkyl described above.

Examples of "alkoxy" include a straight or branched alkoxy having 1 to 6 carbon atoms, for example, methoxy, ethoxy, n-propoxy, isopropoxy, n-butoxy, isobutoxy, sec-butoxy, tert-butoxy, n-pentyloxy, isopentyloxy, n-hexyloxy, and isohexyloxy. Particularly, alkoxy having 1 to 4 carbon atoms is preferable.

Examples of the alkyl moiety of "alkoxycarbonyl" and "alkoxyalkyl" include alkyl described above.

Examples of "alkenyl" include a straight or branched alkenyl having 2 to 6 carbon atoms, for example, vinyl, 1-propenyl, 2-propenyl, 1-butenyl, 2-butenyl, 3-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl. Particularly, alkenyl having 3 to 4 carbon atoms is preferable.

Examples of "cycloalkyl" include a cycloalkyl having 3 to 8 carbon atoms, for example, cyclopropyl, cyclobutyl, cyclopentyl, cyclohexyl, cycloheptyl, and cyclooctyl. Particularly, cycloalkyl having 5 to 7 carbon atoms is preferable.

Examples of "halogen" include fluorine, chlorine, bromine and iodine atoms.

Examples of "aryl" include a aryl having 6 to 10 carbon atoms, for example, phenyl, 1-naphthyl, and 2-naphthyl. Particularly, phenyl is preferable.

Examples of the aryl moiety of "arylalkyl" and "aryloxy" include aryl described above.

Examples of "alkylene" include a straight or branched alkylene having 1 to 8 carbon atoms, for example, methylene, ethylene, 1-methylethylene, 2-methylethylene, trimethylene, tetramethylene, pentamethylene, hexamethylene, heptamethylene, and octamethylene. Particularly, alkylene having 3 to 6 carbon atoms is preferable, and alkylene having 4 carbon atoms is more preferable.

Examples of "alkenylene" include a straight or branched alkenylene having 2 to 8 carbon atoms, for example, ethenylene, 1-propenylene, 2-propenylene, 1-butenylene, 2-butenylene, 3-butenylene, 1-pentenylene, 2-pentenylene, 3-pentenylene, 4-pentenylene, 4-methyl-3-pentenylene, 1-hexenylene, 2-hexenylene, 3-hexenylene, 4-hexenylene, 5-hexenylene, 1-heptenylene, 2-heptenylene, 3-heptenylene, 4-heptenylene, 5-heptenylene, 6-heptenylene, 1-octenylene, 2-octenylene, 3-octenylene, 4-octenylene, 5-octenylene, 6-octenylene, and 7-octenylene. Particularly, alkenylene having 3 to 6 carbon atoms is preferable, and alkenylene having 4 carbon atoms is more preferable.

Examples of "heterocyclic group" include the following groups (1) to (2).

(1) Examples of the heterocyclic group include 5- to 6-membered aromatic ring group having 1 to 4 hetero atoms selected from nitrogen, oxygen and sulfur atoms, or a benzene condensed ring thereof, and nitrogen and sulfur atoms may formed an oxide when a ring-constituent atom is nitrogen atom or sulfur atom. Examples thereof include 1-pyrrolyl, 2-pyrrolyl, 3-pyrrolyl, 3-indolyl, 2-furanyl, 3-furanyl, 3-benzofuranyl, 2-thienyl, 3-thienyl, 3-benzothienyl, 1,3-oxazol-2-yl, 4-isooxazolyl, 2-thiazolyl, 5-thiazolyl, 2-benzothiazolyl, 1-imidazolyl, 2-imidazolyl, 4-imidazolyl, 2-benzimidazolyl, 1H-1,2,4-triazol-1-yl, 1H-tetrazol-5-yl, 2H-tetrazol-5-yl, 2-pyridyl, 3-pyridyl, 4-pyridyl, 3-pyrazolyl, 2-pyrimidinyl, 4-pyrimidinyl, 2-pyrazinyl, and 1,3,5-triazin-2-yl.

(2) Examples of the heterocyclic group include 4- to 8-membered saturated ring group which optionally has 1 to 4 same or different nitrogen, oxygen or sulfur atoms, or a benzene condensed ring thereof, and nitrogen and sulfur atoms may formed an oxide when a ring-constituent atom is nitrogen atom or sulfur atom. Examples thereof include piperidino, piperazinyl, 3-methylpiperazin-1-yl, homopiperazinyl, morpholino, thio morpholino, 1-pyrrolidinyl, 2-pyrrolidinyl, and 2-tetrahydrofuranyl.

The compounds of the present invention can be produced, for example, by the method described below.

In the following method, in case the starting material has a substituent which would not like to be reacted (for example, hydroxy, amino, or carboxy), the starting material is commonly used in the reaction after previously being protected with a protective group (for example, methoxymethyl, 2-methoxyethoxymethyl, benzyl, 4-methoxybenzyl, triphenylmethyl, 4,4'-dimethoxytrityl, acetyl, tert-butoxycarbonyl, benzyloxycarbonyl, phthaloyl, tetrahydropyranyl, or tert-butyldimethylsilyl) by a known method. After the completion of the reaction, the protective group can be eliminated by a known method such as catalytic reduction, alkali treatment, or acid treatment.

Method 1 (Preparation of a Heterocyclic Derivative (1a) wherein A is $NR^7$, O, or S in the Heterocyclic Derivative (1))

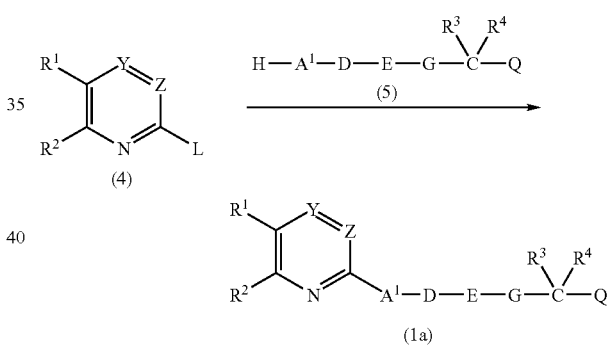

wherein $A^1$ represents $NR^7$, O, or S, L represents an eliminating group such as halogen, mesyloxy, or tosyloxy, and Y, Z, $R^1$, $R^2$, $R^3$, $R^4$, D, E, G and Q are as defined in the general formula (1)

A heterocyclic derivative (1a) can be prepared by reacting a compound (4) with a compound (5). This reaction is usually carried out by using excess compound (5) or a base in the absence of a solvent or in a proper solvent. The amount of the compound (5) is from 1 to 20 moles, and preferably from 1 to 10 moles, per mole of the compound (4). Examples of the base include organic amine (for example, pyridine, triethylamine, triethanolamine, N-methyldiethanolamine, N,N-diisopropylethanolamine, or triisopropanolamine), metal hydride (for example, sodium hydride), and inorganic base (for example, potassium carbonate, sodium hydrogen carbonate, sodium hydroxide, or potassium hydroxide). The solvent is not specifically limited as far as it does not take part in the reaction and examples thereof include ethers such as tetrahydrofuran and diethyl ether; amides such as N,N-dimethylformamide and N,N-dimethylacetamide; nitrites such as acetonitrile and propionitrile; hydrocarbons such as benzene and toluene; and mixed solvents thereof. The reaction temperature varies depending on the kind of the starting material and base to be used and reaction temperature, but is usually from 0° C. to 300° C. The reaction time varies depending on the kind of the starting material to be used and reaction temperature, but is preferably from 30 minutes to 100 hours.

Method 2 (Separate Preparation of a Heterocyclic Derivative (1a))

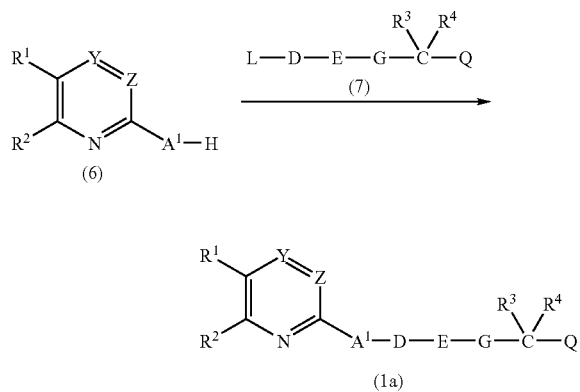

wherein $A^1$ and L are as defined above, and Y, Z, $R^1$, $R^2$, $R^3$, $R^4$, D, E, G and Q are as defined in the general formula (1)

A heterocyclic derivative (1a) can be prepared by reacting a compound (6) (also including a tautomer) with a compound (7). This reaction is carried out in an organic solvent (for example, ethers such as tetrahydrofuran and diethyl ether; amides such as N,N-dimethylformamide and N,N-dimethylacetamide; nitrites such as acetonitrile and propionitrile; hydrocarbons such as benzene and toluene; and mixed solvents thereof) in the presence of a base. The base to be used is the same as that described in the method 1. The amount of the compound (7) is from 1 to 10 moles, and preferably from 1 to 2 moles, per mole of the compound (6). The reaction temperature varies depending on the kind of the starting material and base to be used, but is usually from 0 to 150° C. The reaction time varies depending on the kind of the starting material and base and the reaction temperature, but is preferably from 30 minutes to 24 hours.

Method 3 (Preparation of a Heterocyclic Derivative (1b) wherein A is $NR^7$, O, or S, and G is O in the Heterocyclic Derivative (1))

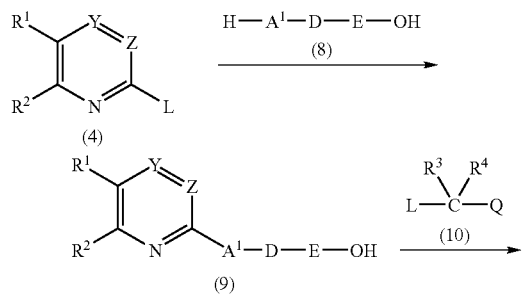

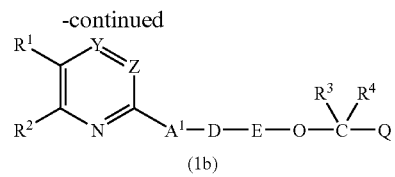

wherein $A^1$ and L are as defined above, and Y, Z, $R^1$, $R^2$, $R^3$, $R^4$, D, E and Q are as defined in the general formula (1)

Step 1

A compound (9) can be prepared by reacting a compound (4) with a compound (8). This reaction can be carried out in the same manner as in the method 1.

Step 2

A heterocyclic derivative (1b) can be prepared by reacting a compound (9) with a compound (10). This reaction can be carried out according to a known method, for example, a method of B. P. Czech et al. (Tetrahedron, 41, 5439 (1985)), a method of A. Takahashi et al. (J. Org. Chem., 53, 1227 (1988)), or a method of N. A. Meanwell et al. (J. Med. Chem., 35, 3498 (1992)).

Method 4 (Separate Preparation of a Heterocyclic Derivative (1b) wherein A is $NR^7$, O, or S, and G is O in the Heterocyclic Derivative (1))

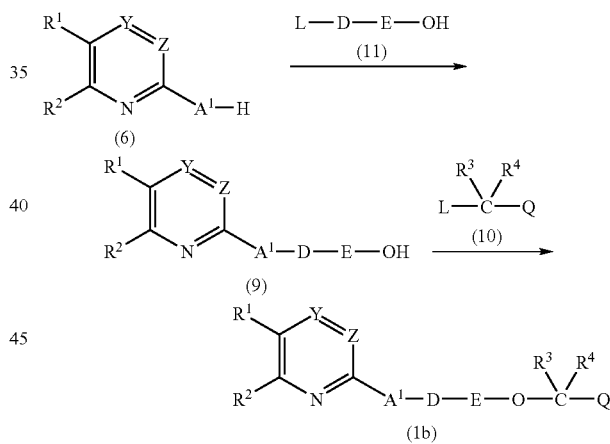

wherein $A^1$ and L are as defined above, and Y, Z, $R^1$, $R^2$, $R^3$, $R^4$, D, E and Q are as defined in the general formula (1)

Step 1

A compound (9) can be prepared by reacting a compound (6) (also including a tautomer) with a compound (11). This reaction can be carried out in the same manner as in the method 2.

Step 2

A heterocyclic derivative (1b) can be prepared by reacting a compound (9) with a compound (10) in the same manner as in the step 2 of the method 3.

Method 5 (Preparation of Heterocyclic Derivative (1c) wherein E is Single Bond, and G is O or S in the Heterocyclic Derivative (1))

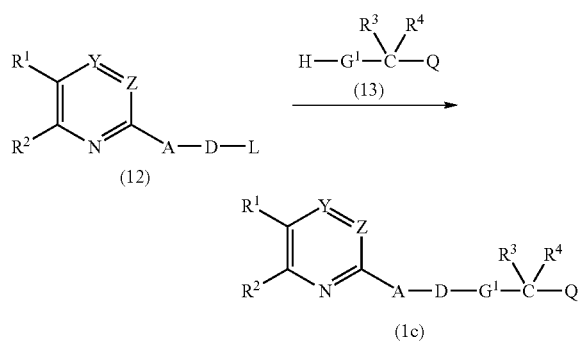

wherein $G^1$ represents O or S, A and L are as defined above, and Y, Z, $R^1$, $R^2$, $R^3$, $R^4$, D and Q are as defined in the general formula (1)

A heterocyclic derivative (1c) can be prepared by reacting a compound (12) with a compound (13). This reaction is carried out by using a base in the absence of a solvent or in a proper solvent. The base to be used is the same as that described in the method 1. The solvent to be used is not specifically limited as far as it does not take part in the reaction and examples thereof include ethers such as tetrahydrofuran and diethyl ether; amides such as N,N-dimethylformamide and N,N-dimethylacetamide; nitriles such as acetonitrile and propionitrile; hydrocarbons such as benzene and toluene; water; and mixed solvents thereof. When using additives, for example, phase transfer catalysts such as hexadecyltributyl phosphonium bromide and iodides such as sodium iodide, the reaction easily proceeds, sometimes. The reaction temperature varies depending on the kind of the starting material to be used, but is usually from 0° C. to 100° C. The reaction time varies depending on the kind of the starting material to be used and the reaction temperature, but is preferably from 30 minutes to 24 hours.

Method 6 (Preparation of a Heterocyclic Derivative (1e) wherein G is SO or a Heterocyclic Derivative (1f) wherein G is $SO_2$ in the Heterocyclic Derivative (1))

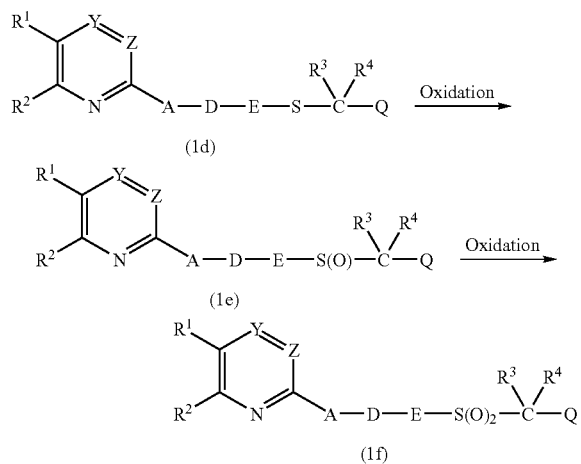

wherein A, Y, Z, $R^1$, $R^2$, $R^3$, $R^4$, D, E and Q are as defined in the general formula (1)

A heterocyclic derivative (1e) can be prepared by oxidizing the heterocyclic derivative (1d) [compound wherein G is S in the heterocyclic derivative (1)] obtained by any method described above or below. This reaction can be carried out in a proper solvent (it is not specifically limited as far as it does not take part in the reaction and examples thereof include amides such as N,N-dimethylformamide and N,N-dimethylacetamide; hydrocarbons such as benzene and toluene; halogenated hydrocarbons such as chloroform and dichloromethane; alcohols such as methanol and ethanol; organic acids such as acetic acid and trifluoroacetic acid; water; and mixed solvents thereof) at −20 to 100° C. in the presence of an oxidizing agent (for example, hydrogen peroxide, peracetic acid, metaperiodate, m-chloroperoxybenzoic acid, halogen, or N-chlorosuccinimide). The reaction time varies depending on the kind of the starting material and the oxidizing agent and the reaction temperature, but is preferably from 30 minutes to 24 hours. The amount of the oxidizing agent is preferably from 1 to 10 moles per mole of the heterocyclic derivative (1d).

A heterocyclic derivative (1f) can be prepared by oxidizing the heterocyclic derivative (1d) or the heterocyclic derivative (1e). This reaction can be carried out in the same solvent as described above in the presence of an oxidizing agent. Examples of the oxidizing agent include hydrogen peroxide, peracetic acid, potassium peroxysulfate, permaganates, and sodium perborate. The reaction temperature and reaction time are the same as those described above.

In case a mixture of the heterocyclic derivative (1e) and the heterocyclic derivative (1f) is obtained as a product, the heterocyclic derivative (1e) and the heterocyclic derivative (1f) can be respectively separated and purified from the mixture by a conventional separation and purification means, for example, extraction, concentration, neutralization, filtration, recrystallization, column chromatography, or thin layer chromatography.

Method 7 (Preparation of a Heterocyclic Derivative (1h) wherein A is SO or a Heterocyclic Derivative (1i) wherein A is $SO_2$ in the Heterocyclic Derivative

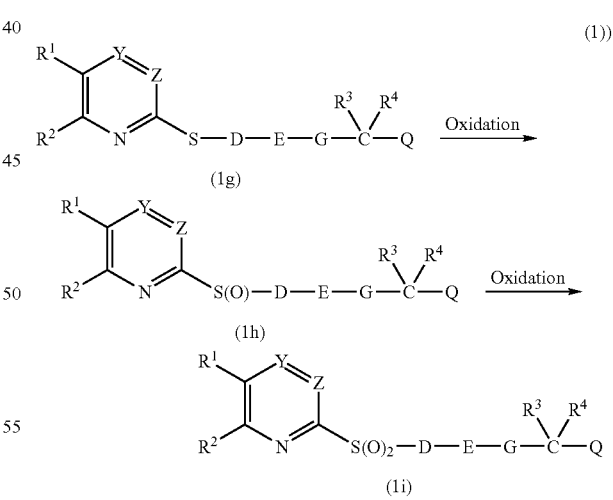

wherein Y, Z, $R^1$, $R^2$, $R^3$, $R^4$, D, E, G and Q are as defined in the general formula (1)

A heterocyclic derivative (1h) can be prepared by oxidizing a heterocyclic derivative (1g) [compound wherein A is S in the heterocyclic derivative (1)] obtained by any method described above. This reaction can be carried out in the same manner as in the preparation of the heterocyclic derivative (1e) from the heterocyclic derivative (1d) in the method 6.

The heterocyclic derivative (1i) can be prepared by oxidizing the heterocyclic derivative (1g) or the heterocyclic derivative (1h). This reaction can be carried out in the same manner as in the preparation of the heterocyclic derivative (1f) from the heterocyclic derivative (1d) or heterocyclic derivative (1e) in the method 6.

In case a mixture of the heterocyclic derivative (1h) and the heterocyclic derivative (1i) is obtained as a product, the heterocyclic derivative (1h) and the heterocyclic derivative (1i) can be respectively separated and purified from the mixture by a conventional separation and purification means, for example, extraction, concentration, neutralization, filtration, recrystallization, column chromatography, or thin layer chromatography.

Method 8 (Preparation of Heterocyclic Derivative (1j) wherein A is Ethylene in the Heterocyclic Derivative (1))

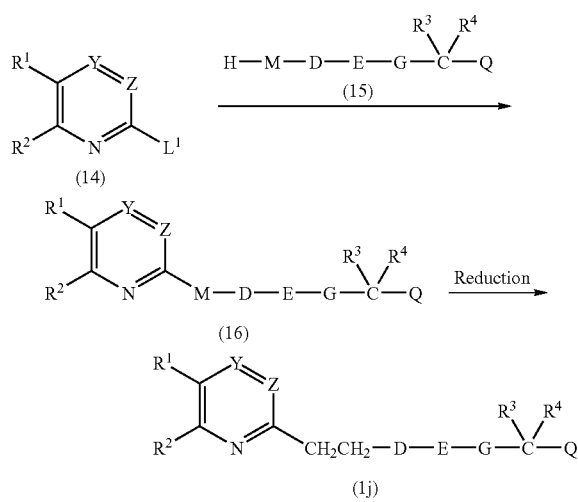

wherein $L^1$ represents halogen, M represents —CH═CH— or —C≡C—, and Y, Z, $R^1$, $R^2$, $R^3$, $R^4$, D, E, G and Q are as defined in the general formula (1)

Step 1

A compound (16) can be prepared by reacting a compound (14) with a compound (15). This reaction can be carried out in a proper solvent at 20 to 150° C. in the presence of a catalyst. As the solvent, for example, there can be used polar solvents such as acetonitrile and N,N-dimethylformamide; ether solvents such as diethyl ether, tetrahydrofuran, and dioxane; hydrocarbon solvents such as benzene and toluene; basic solvents such as triethylamine and piperidine; and mixed solvents thereof. As the catalyst, for example, there can be used palladium catalysts such as dichloro(triphenylphosphine)palladium and tetrakis(triphenylphosphine)palladium; and metal halides such as copper iodide and copper bromide. The reaction time varies depending on the starting material, catalyst and reaction temperature, but is usually from 30 minutes to 48 hours. The amount of the compound (15) is from 1 to 10 moles, and preferably from 1 to 3 moles, per mole of the compound (14).

Using a compound (14) and an alkynyl tin, alkenyl tin, alkynyl zinc or alkenyl zinc compound, a compound (16) can be prepared by a known method. Examples of the method include a method of Y. Akita et al. (Chem. Pharm. Bull., 34, 1447 (1986), Heterocycles, 23, 2327 (1985)).

Step 2

A heterocyclic derivative (1j) can be prepared by catalytic reduction of a compound (16). The compound (1j) can be prepared by reacting with hydrogen under normal pressure or predetermined pressure at 20 to 50° C. in a proper solvent in the presence of a catalyst. Examples of the catalyst to be use include platinum catalyst and palladium catalyst. A weight ratio of the catalyst to the compound (16) is preferably from about 10 to 50%. The solvent is not specifically limited as far as it does not taken part in the reaction and examples thereof include water, methanol, ethanol, propanol, N,N-dimethylformamide, tetrahydrofuran, ethyl acetate, acetic acid, and a mixed solvent thereof.

Alternatively, the heterocyclic derivative (1j) can be prepared directly from the compound (14) by a method of T. Watanabe et al. (Heterocycles, 29, 123 (1989)).

Method 9 (Preparation of a Heterocyclic Derivative (1k) wherein A is Ethylene and G is 0 in the Heterocyclic Derivative (1))

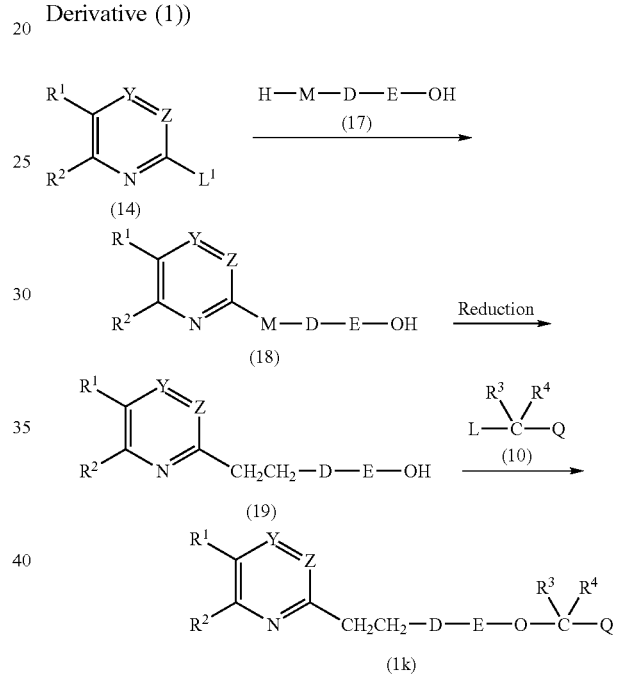

wherein $L^1$ represents halogen, M represents —CH═CH— or —C≡C—, and Y, Z, $R^1$, $R^2$, $R^3$, $R^4$, D, E, G and Q are as defined in the general formula (1)

Step 1

A compound (18) can be prepared by reacting a compound (14) with a compound (17). This reaction can be carried out in the same manner as in the step 1 of the method 8.

Step 2

A compound (19) can be prepared by catalytic reduction of a compound (18). This reaction can be carried out in the same manner as in the step 2 of the method 8.

Step 3

A heterocyclic compound (1k) can be prepared by reacting a compound (19) with a compound (10). This reaction can be carried out in the same manner as in the step 2 of the method 3.

Method 10 (Preparation of a Heterocyclic Derivative (1n) wherein Q is Carboxy in the Heterocyclic Derivative (1))

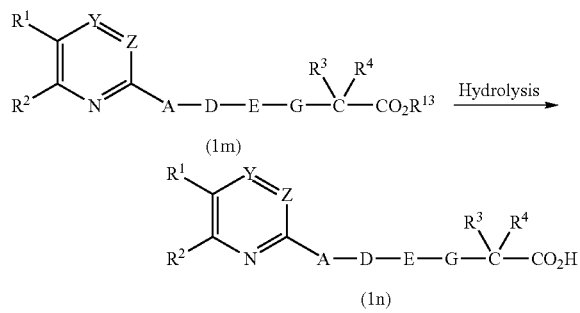

wherein $R^{13}$ represents alkyl, and A, Y, Z, $R^1$, $R^2$, $R^3$, $R^4$, D, E and G are as defined in the general formula (1)

A heterocyclic derivative (1n) can be prepared by hydrolyzing the heterocyclic derivative (1m) obtained by any method described above. This reaction is carried out in a proper solvent in the presence of an acid or a base. Examples of the acid to be used include inorganic acids such as hydrochloric acid and sulfuric acid and examples of the base to be used include inorganic bases such as sodium hydroxide and potassium hydroxide. Examples of the solvent to be used include alcohols such as methanol and ethanol; ethers such as tetrahydrofuran and dioxane; water; and mixed solvents thereof. The reaction temperature varies depending on the starting material and catalyst, but is usually from −10 to 100° C. The reaction time varies depending on the starting material, catalyst and reaction temperature, but is usually from 30 minutes to 5 hours.

Method 11 (Preparation of a Heterocyclic Derivative (1p) wherein Q is Carbamoyl, Monoalkylcarbamoyl, Dialkylcarbamoyl, or a Group Represented by the Formula (22) in the Heterocyclic Derivative (1))

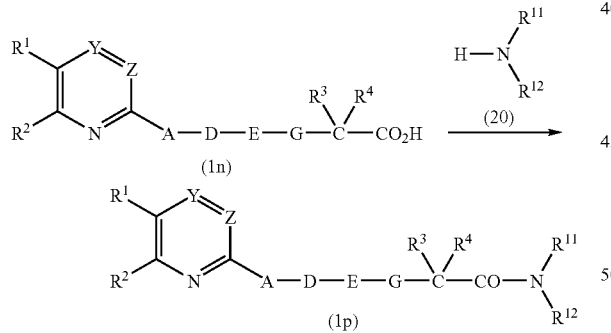

wherein $R^{11}$ and $R^{12}$ are the same or different and each represents hydrogen, alkyl, aminosulfonyl, monoalkylaminosulfonyl, dialkylaminosulfonyl, optionally substituted alkylsulfonyl, optionally substituted arylsulfonyl, optionally substituted aryloxysulfonyl, or optionally substituted heterocyclic sulfonyl, and A, Y, Z, $R^1$, $R^2$, $R^3$, $R^4$, D, E and G are as defined in the general formula (1)

A heterocyclic derivative (1p) can be prepared by reacting a heterocyclic derivative (1n) or a reactive derivative thereof with a compound (20). Examples of the reactive derivative of the heterocyclic derivative (1n) include those used commonly in the amidation, for example, acid halide (acid chloride or acid bromide), mixed acid anhydride, imidazolide, and active amide. When using carboxylic acid of the heterocyclic derivative (1n), the reaction is carried out at −20 to 100° C. using condensing agents (for example, 1-ethyl-3-(3-dimethylaminopropyl)carbodiimide, dicyclohexyl carbodiimide, diethyl cyanophophonate, and diphenylphophoryl azide) in the presence or absence of a base (for example, organic base such as triethylamine, N,N-dimethylaniline, pyridine, 4-dimethylaminopyridine, or 1,8-diazabicyclo[5.4.0]undec-7-ene). The solvent to be used is not specifically limited as far as it does not take part in the reaction and examples thereof include ethers such as tetrahydrofuran and diethyl ether; amides such as N,N-dimethylformamide and N,N-dimethylacetamide; nitrites such as acetonitrile and propionitrile; hydrocarbons such as benzene and toluene; halogenated hydrocarbons such as chloroform and dichloromethane; and mixed solvents thereof. In this case, additives (for example, 1-hydroxybenzotriazole, N-hydroxysuccinimide) can also be added. The reaction time varies depending on the kind of the condensing agent and the reaction temperature, but is preferably from 30 minutes to 24 hours. The amount of the compound (20) and the condensing agent is preferably from 1 to 3 moles per mole of the heterocyclic derivative (1n). When using acid halide as the reactive derivative of the heterocyclic derivative (1n), the reaction is carried out at −20 to 100° C. using the same base and solvent as those described above. The reaction time varies depending on the kind of the acid halide and the reaction temperature, but is preferably from 30 minutes to 24 hours. The amount of the compound (20) is preferably from 1 to 3 moles per mole of the acid halide.

Method 12 (Preparation of a Heterocyclic Derivative (1r) wherein Q is —CONHSO$_3$H in the Heterocyclic Derivative (1))

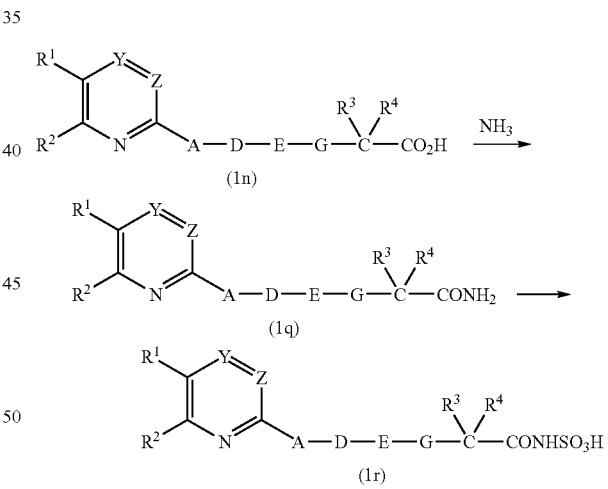

Step 1

A compound (1q) can be prepared by reacting a compound (1n) or a reactive derivative thereof with ammonia. This reaction can be carried out in the same manner as in the method 11.

Step 2

A compound (1r) can be prepared by using the compound (1q) obtained in the step 1 according to a known method (Tetrahedron, 39, 2577 (1983), Tetrahedron, 56, 5667 (2000), J. Org. Chem., 50, 3462 (1985), J. Chem. Soc., Perkin Trans. I, 649 (1988)), for example, by dissolving 2-picolione in a halogenated solvent, adding chlorosulfonic acid and adding a compound (1q). The reaction temperature and reaction time vary depending on the starting material, but the reaction is preferably carried out at −50 to 100° C. for 30 minutes to 5 hours.

The compounds (4) to (20) used as the starting material in these reactions are known compounds, or can be prepared according to a known method, or by the method described in Reference Examples.

The compounds of the present invention can be separated and purified from the above reaction mixture by a conventional separation and purification means, for example, extraction, concentration, neutralization, filtration, recrystallization, column chromatography, or thin layer chromatography.

The compounds of the present invention can be used as a medicine in the form of a free base or acid, but can also be used after forming into a pharmaceutically acceptable salt by a known method. In case the compounds of the present invention are basic, examples of "salt" include salts of inorganic acids such as hydrochloric acid, sulfuric acid, nitric acid, phosphoric acid, hydrofluoric acid and hydrobromic acid, and salts of organic acids such as acetic acid, tartaric acid, lactic acid, citric acid, fumaric acid, maleic acid, succinic acid, methanesulfonic acid, ethanesulfonic acid, benzenesulfonic acid, p-toluenesulfonic acid, naphthalenesulfonic acid and camphorsulfonic acid.

In case the compounds of the present invention are acidic, examples of "salt" include alkali metal salts such as sodium salt and potassium salt, and alkali earth metal salts such as calcium salt.

In the compounds of the present invention, geometrical isomers (Z form and E form) exist and these isomers and a mixture thereof are also included in the present invention.

In the compounds of the present invention, those having asymmetric carbon also exist and these optical isomers and a racemic form thereof are also included in the present invention. The optical isomer can be prepared from the racemic form obtained as described above by optically resolving with an optically active acid (for example, tartaric acid, dibenzoyltartaric acid, mandelic acid, or 10-camphorsulfonic acid) utilizing its basicity, or using a previously prepared optically active compound as the starting material.

The compounds of the present invention are excellent $PGI_2$ receptor agonists and exert platelet aggregation inhibitory effect, vasodilation effect, bronchodilatation effect, lipid deposition inhibitory effect and leucocyte activation inhibitory effect as shown in Test Examples described below, and also have low toxicity. Therefore, the compounds of the present invention are useful as a preventive or therapeutic agent for transient ischemic attack (TIA), diabetic neuropathy, diabetic gangrene, peripheral vascular disease (for example, arteriosclerosis obliterans, intermittent claudication, peripheral arterial embolism, vibration disease and Raynaud's disease), systemic lupus erythematosus, reocclusion or restenosis after percutaneous transluminal coronary angioplasty (PTCA), arteriosclerosis, thrombosis (for example, acute cerebral thrombosis), diabetic nephropathy, hypertension, pulmonary hypertension, ischemic diseases (for example, cerebral infarction and myocardial infarction), angina pectoris (for example, stable angina and unstable angina), glomerulonephritis, diabetic nephropathy, allergy, bronchial asthma, ulcer, bedsore (decubitus), restenosis after intervention of coronary artery such as atherectomy and indwelling of stent, and thrombocytopia caused by dialysis. Also the compounds of the present invention are useful as an agent for acceleration of gene therapy or angiogenesis therapy such as autologous bone marrow cell transplantation.

When the compounds of the present invention are administered as a medicine, they can be administered to a mammal including human as they are or in a mixture with a pharmaceutically acceptable non-toxic inert carrier, for example, as a pharmaceutical composition containing the compound at a level of 0.1% to 99.5%, preferably 0.5% to 90%.

As a carrier, one or more of auxiliary agents for formulations such as solid, semi-solid and liquid diluent, filler and other auxiliary agents for drug formulations may be used. It is desirable that a pharmaceutical composition is administered as a unit dosage form. The pharmaceutical composition can be administered into tissue, or intravenously, orally, topically (percutaneously) or rectally. It is a matter of course that a dosage form suitable for any of the administration modes described above is employed. For example, oral administration is preferable.

While it is desirable that the dose may be adjusted depending on the conditions of the patients including the age and body weight, the administration route, nature and degree of the disease as well as a daily dose as an active ingredient in an adult is usually 0.01 mg to 1000 mg per adult, preferably 0.1 mg to 100 mg per adult.

In some cases, a lower dose may be sufficient or a higher dose may be required. Usually, the dose is given once or several times as being divided into portions.

BEST MODE FOR CARRYING OUT THE INVENTION

The present invention will now be described in more detail with reference to Production Examples of Reference Examples, Examples and Test Examples, but the present invention is not limited thereto.

REFERENCE EXAMPLE 1

4-(isopropylamino)-1-butanol 100.40 g of 4-amino-1-butanol was dissolved in a mixed solvent of 108 ml of acetone and 160 ml of ethanol and, after adding 2.1 g of platinum (IV) oxide, hydrogenation was carried out under the pressure of 2 to 3 atms for 48 hours. A catalyst was removed by filtering the reaction solution and the filtrated was concentrated to obtain 147.64 g of the desired compound as a colorless oily substance.

REFERENCE EXAMPLE 2

4-(cyclopentylamino)-1-butanol

In the same manner as in Reference Example 1, except that cyclopentanone was used in place of acetone, a pale yellow oily substance was prepared.

REFERENCE EXAMPLE 3

4-(cyclohexylamino)-1-butanol

In the same manner as in Reference Example 1, except that cyclohexanone was used in place of acetone, a colorless crystal having a melting point of 48 to 50° C. was prepared.

REFERENCE EXAMPLE 4

4-(aminomethyl)-1-butanol

Step 1

4-(formylamino)-1-butanol 10 g of 4-amino-1-butanol was dissolved in 100 ml of ethanol and 13.6 ml of ethyl formate was added. After the mixture was heated at reflux for 18 hours, the solvent was evaporated under reduced pressure to obtain 13.29 g of the desired compound as a pale yellow oily substance.

Step 2

4-(aminomethyl)-1-butanol 6.36 g of aluminum lithium hydride was suspended in 100 ml of tetrahydrofuran and a solution of 13.29 g of 4-(formylamino)-1-butanol in 50 ml of tetrahydrofuran was dropwise at the rate which enables slow reflux. After the mixture was refluxed for 1.5 hours, the reaction solution was ice-cooled and 6.3 ml of water, 6.3 ml of an aqueous 15% sodium hydroxide solution and 18.9 ml of water were added dropwise in order, followed by stirring for 30 minutes. The insoluble matter was removed by filtration and the solvent in the filtrate was evaporated under reduced pressure. The residue was distilled off under reduced pressure to obtain 6.73 g of he desired compound as a colorless oily substance. Boiling point: 84 to 85° C./16 mmHg.

REFERENCE EXAMPLE 5

(±)-3-(2-pyrrolidinyl)-1-propanol

Step 1

(±)-N-benzyloxycarbonyl-2-pyrrolidine carboxylic acid methyl ester

To a solution of 28.83 g of (±)-N-benzyloxycarbonyl-2-pyrrolidine carboxylic acid in 180 ml of N,N-dimethylformamide, 23.23 g of potassium hydrogen carbonate and 10.8 ml of methyl iodide were added. After stirring at room temperature for 15 hours, the reaction solution was diluted with water and then extracted twice with diethyl ether. After the extract was washed with an aqueous 5% sodium hydrogen sulfite solution and water and dried over anhydrous magnesium sulfate, the solvent was evaporated under reduced pressure to obtain 26.52 g of the desired compound as a yellowish oily substance.

Step 2

(±)-N-benzyloxycarbonyl-2-formylpyrrolidine

To a solution of 12.00 g of (±)-N-benzyloxycarbonyl-2-pyrrolidine carboxylic acid methyl ester in 50 ml of dry dichloromethane, 50 ml of diisobutylaluminum hydride (1M toluene solution) was added dropwise under an argon atmosphere at −70° C. or lower, followed by stirring for 2 hours. To the reaction solution, 230 ml of 1N hydrochloric acid was added dropwise, and then the mixture was heated to room temperature and extracted with diethyl ether. The extract was washed with water and dried over anhydrous magnesium sulfate, and then the solvent was evaporated under reduced pressure. The residue was purified by silica gel column chromatography to obtain 4.72 g of the desired compound as a colorless oily substance.

Step 3

(±)-3-(N-benzyloxycarbonylpyrrolidin-2-yl)acrylic Acid Ethyl Ester 376 mg of 60% sodium hydride was washed with hexane to remove an oil component and suspended in 10 ml of anhydrous tetrahydrofuran, and then a solution of 2.11 g of diethyl ethoxycarbonylmethanephosphonate in 2 ml of anhydrous tetrahydrofuran was added dropwise at room temperature. After stirring for 10 minutes, a solution of 2.00 g of (±)-N-benzyloxycarbonyl-2-formylpyrrolidine in 5 ml of anhydrous tetrahydrofuran was added dropwise over about 10 minutes, followed by stirring for additional 30 minutes. The reaction solution was poured into water, extracted with diethyl ether and dried over magnesium sulfate, and then the solvent was evaporated under reduced pressure. The residue was purified by silica gel column chromatography to obtain 1.86 g of the desired compound as a colorless oily substance.

Step 4

(±)-3-(N-benzyloxycarbonylpyrrolidin-2-yl)-2-propen-1-ol

To a solution of 1.86 g of (±)-3-(N-benzyloxycarbonylpyrrolidin-2-yl)acrylic acid ethyl ester in 15 ml of dry dichloromethane1, 12.9 ml of diisobutylaluminum hydride (1M toluene solution) was added dropwise under an argon atmosphere at −70° C. or lower, followed by stirring for one hour. To the reaction solution, 60 ml of 1N hydrochloric acid was added dropwise, and then the mixture was heated to room temperature and extracted with diethyl ether. The extract was washed with water and dried over anhydrous magnesium sulfate, and then the solvent was evaporated under reduced pressure. The residue was purified by silica gel column chromatography to obtain 0.75 g of the desired compound as a colorless oily substance.

Step 5

(±)-3-(2-pyrrolidinyl)-1-propanol 0.73 g of (±)-3-(N-benzyloxycarbonylpyrrolidin-2-yl)-2-propen-1-ol was dissolved in 7 ml of ethanol and, after adding 200 mg of 5% palladium-carbon, the mixture was heated to 35° C. and hydrogenated at atmospheric pressure for 8 hours. A catalyst was removed by filtering the reaction solution and the filtrate was concentrated under reduced pressure to obtain 0.34 g of the desired compound as a pale yellow oily substance.

REFERENCE EXAMPLE 6

6-chloro-2,3-diphenylpyridine

Step 1

2,3-diphenylpyridin-1-oxide 1 g of 2,3-diphenylpyridine was dissolved in chloroform and 1.4 g of 70% m-chloroperoxybenzoic acid was added, followed by stirring at room temperature for 15 hours. After the reaction solution was washed with an aqueous 5% potassium carbonate solution and saturated brine, and dried over anhydrous magnesium sulfate, the solvent was evaporated under reduced pressure to obtain 1.3 g of a crude crystal. The crude crystal was washed with diisopropyl ether to obtain 922 mg of the desired compound as a colorless crystal having a melting point of 167 to 170° C.

Step 2

6-chloro-2,3-diphenylpyridine

To 922 mg of 2,3-diphenylpyridin-1-oxide, 3 ml of phosphorus oxychloride was added, followed by stirring at 100° C. for 15 minutes. The reaction solution was poured into iced water, extracted with ethyl acetate and then washed with an aqueous 5% potassium carbonate solution and saturated brine. After drying over anhydrous magnesium sulfate, the solvent was evaporated under reduced pressure. The residue was purified by silica gel column chromatography to obtain 428 mg of the desired compound as an oily substance.

REFERENCE EXAMPLE 7

(±)-1-(2-pyrrolidinyl)-4-(2-tetrahydropyranyloxy)butane

Step 1

(±)-1-(N-benzyloxycarbonylpyrrolidin-2-yl)-4-(2-tetrahydropyranyloxy)-1-butene

Under an argon atmosphere, a suspension of 6.76 g 3-(2-tetrahydropyranyloxy)propyltriphenylphosphonium bromide in 30 ml of dry tetrahydrofuran was ice-cooled and 8.7 ml of n-butyllithium (1.6M hexane solution) was added dropwise. After stirring for 15 minutes, an ice bath was removed and the mixture was continuously stirred for one hour. A solution of 2.70 g of (±)-N-benzyloxycarbonyl-2-formylpyrrolidine obtained in the Step 2 of Reference Example 5 in 15 ml of dry tetrahydrofuran was added dropwise at room temperature, followed by stirring for 2 hours. The reaction solution was ice-cooled and an aqueous saturated ammonium chloride solution was added and, after extracting with diethyl ether, the extract was washed with saturated brine and dried over anhydrous magnesium sulfate, and then the solvent was evaporated under reduced pressured. The residue was purified by silica gel column chromatography to obtain 3.40 g of the desired compound as a colorless oily substance.

Step 2

(±)-1-(2-pyrrolidinyl)-4-(2-tetrahydropyranyloxy)butane 3.40 g of (±)-1-(N-benzyloxycarbonylpyrrolidin-2-yl)-4-(2-tetrahydropyranyloxy)-1-butene was dissolved in 30 ml of ethanol and 600 mg of 5% palladium-carbon was added. The mixture was heated to 35° C. to 40° C. and hydrogenated under normal pressure for 24 hours. A catalyst was removed by filtering the reaction solution and the filtrate was concentrated under reduced pressure. The residue was purified by silica gel column chromatography to obtain 1.42 g of a mixture of the desired compound and (±)-1-(2-pyrrolidinyl)-4-(2-tetrahydropyranyloxy)-1-butene as a pale yellow oily substance. To a solution of the resulting mixture in 14 ml of methanol, 200 mg of 5% palladium-carbon was added. The mixture was hydrogenated under 2 atms at 30 to 40° C. for 2 hours. The above post-treatment and purification were carried out to obtain 1.43 g of the desired compound as a pale yellow oily substance.

REFERENCE EXAMPLE 8

3-(methoxymethoxy)-N-methylbenzylamine

Step 1

3-(methoxymethoxy)benzaldehyde

A solution of 100 g of 3-hydroxybenzaldehyde and 214 ml of N-ethyldiisopropylamine in 800 ml of dichloromethane was ice-cooled and a solution of 68.4 ml of chloromethyl methyl ether in 200 ml of dichloromethane was added dropwise. After stirring for one hour, an ice bath was removed and the mixture was continuously stirred at room temperature overnight. The reaction solution was washed in turn with an aqueous 10% sodium hydroxide solution and 10% citric acid and dried over magnesium sulfate, and then the solvent was evaporated under reduced pressure. The residue was distilled off under reduced pressure to obtain 81.3 g of the desired compound as a colorless oily substance. Boiling point: 125 to 127° C./10 mmHg Step 2

3-(methoxymethoxy)-N-methylbenzylamine

5% platinum-carbon was suspended in 10 ml of methanol and a solution of 3.00 g of 3-(methoxymethoxy)benzaldehyde in 10 ml of methanol and 2.1 ml of 40% methylamine (methanol solution) were added. After heating to 30° C. under 2 atm, hydrogen was added for 22 hours. A catalyst was removed by filtering the reaction solution and the filtrate was concentrated. The residue was purified by silica gel column chromatography to obtain 2.51 g of the desired compound as a yellowish oily substance.

REFERENCE EXAMPLE 9

1-[3-(benzyloxy)phenyl]-2-(methylamino)ethane

Step 1

1-[3-(benzyloxy)phenyl]-2-(formylamino)ethane

To a solution of 8.60 g of 2-[3-(benzyloxy)phenyl]ethylamine in 50 ml of ethanol, 4.6 ml of ethyl formate was added and the mixture was heated at reflux for 18 hours. The solvent was evaporated under reduced pressure and the residue was purified by silica gel column chromatography to obtain 4.81 g of the desired compound as a pale orange oily substance.

Step 2

1-[3-(benzyloxy)phenyl]-2-(methylamino)ethane 1.07 g of aluminum lithium hydride was suspended in 20 ml of tetrahydrofuran and a solution of 4.78 g of 1-[3-(benzyloxy)phenyl]-2-(formylamino)ethane in 10 ml of tetrahydrofuran was added dropwise at room temperature. The mixture was stirred at room temperature for 30 minutes and then heated at reflux for 2 hours. The reaction solution was ice-cooled and 1 ml of water, 1 ml of an aqueous 15% sodium hydroxide solution and 3 ml of water were added dropwise in order, followed by stirring for 30 minutes. The insoluble solid was removed by filtration and the solvent in the filtrate was evaporated under reduced pressure. The residue was purified by silica gel column chromatography to obtain 3.46 g of the desired compound as a pale yellow oily substance.

REFERENCE EXAMPLE 10

1-methylamino-4-(methoxymethoxy)indane

Step 1

4-(methoxymethoxy)-1-indanone

To a solution of 4.12 g of 4-hydroxy-1-indanone and 7.3 ml of N-ethyldiisopropylamine in 30 m of dichloromethane, 2.3 ml of chloromethyl methyl ether was added dropwise while stirring under ice cooling. An ice bath was removed and the mixture was continuously stirred overnight. The reaction solution was diluted with diethyl ether, washed with water, an aqueous 10% citric acid solution and an aqueous 5% sodium hydroxide solution, and then dried over anhydrous magnesium sulfate. The solvent was evaporated under reduced pressure to obtain 4.23 g of the desired compound as a pale orange crystal having a melting point of 51 to 54° C.

Step 2

1-methylamino-4-(methoxymethoxy)indane

To a solution of 1.00 g of 4-(methoxymethoxy)-1-indanone in 10 ml of ethanol, 2.8 ml of 40% methylamine (methanol solution) and 367 mg of sodium cyanoborohydride were added. While stirring at room temperature, 0.55 ml of acetic acid was added dropwise and the mixture was heated at reflux for 4 hours. The reaction solution was air-cooled, combined with water and then extracted with ethyl acetate. After drying over anhydrous magnesium sulfate, the solvent was evaporated. The residue was purified by silica gel column chromatography to obtain 0.61 g of the desired compound as a deep green oily substance.

REFERENCE EXAMPLE 11

2-(4-bromobutyloxy)acetic acid tert-butyl ester

Step 1

4-(2-tetrahydropyranyloxy)-1-butanol

To a solution of 100.0 g of 1,4-butanediol and 20 ml of 3,4-dihydro-2H-pyrane in 80 ml of dichloromethane and 140 ml of tetrahydrofuran, 1.8 g of pyridinium p-toluenesulfonate was added. After stirring at room temperature for 18 hours, the solvent was evaporated under reduced pressure. The residue was extracted three times with diethyl ether after adding saturated brine. After the extract was washed with a small amount of water and dried over anhydrous magnesium sulfate, the solvent was evaporated to obtain 35.98 g of the desired crude product as a colorless oily substance.

Step 2

2-[4-(2-tetrahydropyranyloxy)butyloxy]acetic Acid Tert-Butyl Ester 35.98 g of 4-(2-tetrahydropyranyloxy)-1-butanol was dissolved in 300 ml of benzene and then 33.95 g of tetra-n-butylammonium hydrogen sulfate and 300 ml of an aqueous 40% potassium hydroxide solution were added. While stirring vigorously under ice cooling, 10.5 ml of tert-butyl bromoacetate was added dropwise so as to control the inner temperature to 5 to 10° C. or lower. After stirring for 45 minutes, an ice bath was removed and the mixture was stirred at room temperature for one hour. The reaction solution was diluted with water and then extracted with diethyl ether. The extract was washed with saturated brine and dried over anhydrous magnesium sulfate, and then the solvent was evaporated under reduced pressure. The residue was purified by silica gel column chromatography to obtain 36.21 g of the desired compound as a colorless oily substance.

Step 3

2-(4-hydroxybutyloxy)acetic Acid Tert-Butyl Ester

To a solution of 36.21 g of 2-[4-(2-tetrahydropyranyloxy)butyloxy]acetic acid tert-butyl ester in 360 ml of methanol, 47.77 g of p-toluenesulfonic acid monohydrate was added. After stirring at room temperature for 30 minutes, the reaction solution was neutralized with an aqueous sodium hydrogen carbonate solution and the solvent was evaporated under reduced pressure. The residue was diluted with water, extracted with diethyl ether, washed with water and dried over anhydrous magnesium sulfate, and then the solvent was evaporated under reduced pressure. The residue was purified by silica gel column chromatography to obtain 17.02 g of the desired compound as a colorless oily substance.

Step 4

2-(4-bromobutyloxy)acetic Acid Tert-Butyl Ester

To a solution of 17.02 g of 2-(4-hydroxybutyloxy)acetic acid tert-butyl ester in 400 ml of dichloromethane, 24.04 g of triphenylphosphine and 31.78 g of carbon tetrabromide were added. After stirring at room temperature for one hour, the solvent was evaporated under reduced pressure. The residue was purified by silica gel column chromatography to obtain 16.95 g of the desired compound as a colorless oily substance.

REFERENCE EXAMPLE 12

5,6-diphenyl-2-(ethylamino)pyrazine 1.00 g of 2-chloro-5,6-diphenylpyrazine was added to 18.7 ml of 2M ethylamine in methanol and the mixture was reacted in a sealed tube at 80° C. for 16 hours. After cooling, 12 ml of a 2M ethylaminemethanol solution was further added, followed by continuous stirring in the sealed tube at 90° C. for 17.5 hours and further stirring at room temperature for 46 hours. After the solvent was evaporated under reduced pressure, the residue was purified by silica gel column chromatography to obtain 531 mg of the desired compound as a pale yellow crystal having a melting point of 121 to 123° C.

REFERENCE EXAMPLE 13

2-allylamino-5,6-diphenylpyrazine

To a solution of 1.00 g of 2-chloro-5,6-diphenylpyrazine in 10 ml of methanol, 2.14 g of allylamine was added and the mixture was reacted in a sealed tube at 80° C. for 41 hours, followed by stirring at room temperature for 54 hours. After the solvent was evaporated under reduced pressure, the reaction solution was combined with water, extracted with chloroform, dried over anhydrous magnesium sulfate, and then the solvent was evaporated under reduced pressure. The residue was purified by silica gel column chromatography to obtain 330 mg of the desired compound as a pale yellow crystal having a melting point of 97 to 100° C.

REFERENCE EXAMPLE 14

2-[4-chloro-(Z)-2-buten-1-yloxy]acetic acid tert-butyl ester

Step 1

(Z)-4-(2-tetrahydropyranyloxy)-2-buten-1-ol 50 g of 1,4-butenediol was dissolved in 200 ml of tetrahydrofuran and 280 mg of pyridinium p-toluenesulfonate was added and a solution prepared by dissolving 10.27 g of 3,4-dihydro-2H-pyrane in 50 ml of tetrahydrofuran was added dropwise under ice cooling. After the temperature was returned to room temperature, the reaction solution was stirred for 21 hours. The solvent was evaporated under reduced pressure and the residue was extracted with diethyl ether after adding water. The extract was washed with saturated brine and dried over anhydrous magnesium sulfate, and then the solvent was evaporated under reduced pressure to obtain 7.05 g of a desired crude product as a colorless oily substance.

Step 2

2-[4-(2-tetrahydropyranyloxy)-(Z)-2-buten-1-yloxy]acetic Acid Tert-Butyl Ester 6.00 g of (Z)-4-(2-tetrahydropyranyloxy)-2-buten-1-ol was dissolved in 10 ml of benzene and 1.18 g of tetra-n-butylammonium hydrogen sulfate and 10 ml of an aqueous 50% sodium hydroxide solution were added and 6.75 ml of tert-butyl bromoacetate was added dropwise while stirring under ice cooling. After 10 minutes, the temperature was returned to room temperature and the reaction solution was stirred for one hour. The solution was extracted with diethyl ether after adding ice water. The extract was washed with saturated brine and the solvent was evaporated under reduced pressure. The residue was purified by silica gel column chromatography to obtain 1.00 g of the desired compound as a colorless oily substance.

Step 3

2-[4-hydroxy-(Z)-2-buten-1-yloxy]acetic Acid Tert-Butyl Ester

To a solution of 1.00 g of 2-[4-(2-tetrahydropyranyloxy)-(Z)-2-buten-1-yloxy]acetic acid tert-butyl ester in 30 ml of methanol, 88 mg of pyridinium p-toluenesulfonate was added and the mixture was heated at reflux for 3 hours. The solvent was evaporated under reduced pressure and the reaction solution was extracted with ethyl acetate after adding water. After the extract was dried over anhydrous magnesium sulfate, the solvent was evaporated under reduced pressure to obtain 420 mg of the desired compound as an oily substance.

Step 4

2-[4-chloro-(Z)-2-buten-1-yloxy]acetic Acid Tert-Butyl Ester

To a solution of 420 mg of 2-[4-hydroxy-(Z)-2-buten-1-yloxy]acetic acid tert-butyl ester in 10 ml of N,N-dimethylformamide, 1.00 g of 2,4,6-collidine and 350 mg of lithium chloride were added. While stirring under ice cooling, 0.64 ml of methanesulfonyl chloride was added dropwise, followed by stirring at room temperature for 2 hours. The reaction solution was extracted with ethyl acetate after adding iced water, and dried over anhydrous magnesium sulfate, and then the solvent was evaporated under reduced pressure. The residue was purified by silica gel column chromatography to obtain 350 mg of the desired compound as a colorless oily substance.

REFERENCE EXAMPLE 15

2-[4-chloro-(E)-2-buten-1-yloxy]acetic acid methyl ester

Step 1

2-[3-formyl-(E)-2-propen-1-yloxy]acetic acid methyl ester

To a solution of 1.57 g of 2-[4-hydroxy-(Z)-2-buten-1-yloxy]acetic acid methyl ester in 157 ml of benzene, 7.90 g of celite and 4.87 g of pyridinium chlorochromate were added, followed by stirring at room temperature for 23 hours. The insoluble matter was removed by filtration and the solvent in the filtrate was evaporated under reduced pressure. After the was dissolved in ethyl acetate, the insoluble matter was removed by filtering trough celite to obtain 311 mg of the desired crude product as a brown oily substance.

Step 2

2-[4-hydroxy-(E)-2-buten-1-yloxy]acetic Acid Methyl Ester

To a solution of 311 mg of 2-[3-formyl-(E)-2-propen-1-yloxy]acetic acid methyl ester in 10 ml of methanol, 149 mg of sodium borohydride was added, followed by stirring at room temperature for 4.5 hours. The solvent was evaporated under reduced pressure and the residue was extracted with ethyl acetate after adding ice water. The extract was washed with saturated brine and dried over anhydrous magnesium sulfate, and then the solvent was evaporated under reduced pressure to obtain 187 mg of the desired crude product as an oily substance.

Step 3

2-[4-chloro-(E)-2-buten-1-yloxy]acetic Acid Methyl Ester

In the same manner as in the step 4 of Reference Example 14, except that 2-[4-hydroxy-(E)-2-buten-1-yloxy]acetic acid methyl ester was used in place of 2-[4-hydroxy-(Z)-2-buten-1-yloxy]acetic acid tert-butyl ester, the desired colorless oily substance was prepared.

REFERENCE EXAMPLE 16

2,3-diphenyl-5-(methylamino)pyrazine 1-oxide

To 1.00 g of 5-chloro-2,3-diphenylpyrazine 1-oxide, 20 ml of 40% methylamine in methanol was added and the mixture was reacted in a sealed tube at room temperature for 15 hours. The reaction solution was extracted with ethyl acetate after adding water. The extract was dried over anhydrous magnesium sulfate and the solvent was evaporated under reduced pressure. The resulting crude crystal was washed with diisopropyl ether to obtain 536 mg of the desired compound as a pale yellow crystal having a melting point of 145 to 147° C.

REFERENCE EXAMPLE 17

4,5-diphenyl-2-(methylamino)pyrimidine

Step 1

3-(dimethylamino)-1,2-diphenyl-2-propen-1-one 25.00 g of benzyl phenyl ketone was mixed with 92 ml of N,N-dimethylformamide dimethyl acetal and then heated at reflux for one hour. Almost all of N,N-dimethylformamide dimethyl acetal was evaporated under reduced pressure and the deposited crystal was washed with diethyl ether. After drying, 31.40 g of the desired compound was obtained as a pale yellow crystal having a melting point of 128 to 130° C.

Step 2

4,5-diphenyl-2-(methylamino)pyrimidine 10.00 g of 3-(dimethylamino)-1,2-diphenyl-2-propen-1-one, 6.90 g of 1-methylguanidine hydrochloride and 8.70 g of potassium carbonate were added to 20 ml of xylene and then heated at reflux for 13 hours using a reflux condenser equipped with a Dean-Stark water separator. The reaction solution was extracted with ethyl acetate after adding water, dried over anhydrous magnesium sulfate, and then the solvent was evaporated. The crude crystal was washed with diisopropyl ether and dried to obtain 6.51 g of the desired compound as a pale yellow crystal having a melting point of 136 to 138° C.

REFERENCE EXAMPLE 18

4,5-di-p-tolyl-2-(methylamino)pyrimidine

Step 1

N-methoxy-N-methyl-p-toluamide

To a solution of 10.00 g of p-toluoyl chloride in 300 ml of dichloromethane, 6.94 g of N,O-dimethylhydroxyamine hydrochloride was added. The reaction solution was ice-cooled and 11.5 ml of pyridine was added dropwise. After the completion of dropwise addition, the mixture was stirred at room temperature for one hour and the solvent was evaporated under reduced pressure. The residue was combined with water, extracted with diethyl ether and then washed in turn with 10% hydrochloric acid, water and an aqueous saturated sodium hydrogen carbonate solution. After drying over anhydrous magnesium sulfate, the solvent was evaporated under reduced pressure to obtain 10.40 g of the desired compound as a colorless oily substance.

Step 2

1,2-di-p-tolylethan-1-one

Under an argon atmosphere, a solution of 10.40 g of N-methoxy-N-methyl-p-toluamide in 100 ml of tetrahydrofuran was ice-cooled and 4-methylbenzylmagnesium chloride (solution prepared by dissolving 10.60 g of α-chloro-p-xylene and 1.94 g of magnesium in 85 ml of tetrahydrofuran) was added dropwise. After stirring for one hour, 100 ml of 10% hydrochloric acid was slowly added. The reaction solution was diluted with water, extracted with diethyl ether, washed with water and then dried over anhydrous magnesium sulfate. The solvent was evaporated under reduced pressure and the crude crystal was washed with diisopropyl ether and then dried under reduced pressure to obtain 8.43 g of the desired compound as a colorless crystal having a melting point of 93 to 100° C.

Step 3

4,5-di-p-tolyl-2-(methylamino)pyrimidine

In the same manner as in the Steps 1 and 2 of Reference Example 17, except that 1,2-di-p-tolylethan-1-one was used in place of benzyl phenyl ketone, the desired compound was obtained as a pale yellow crystal having a melting point of 160 to 162° C.

REFERENCE EXAMPLE 19

5-(benzyloxy)-2-(chloromethyl)-3,4-dihydronaphthalene

Step 1

5-(benzyloxy)-1-tetralone

To a solution of 4.86 g of 5-hydroxy-1-tetralone in 50 ml of acetonitrile, 5.13 g of benzyl bromide and 6.22 g of potassium carbonate were added and the mixture was heated at reflux for 4 hours. The insoluble matter was removed by filtration and the filtrate was concentrated. The residue was purified by silica gel column chromatography to obtain 6.62 g of the desired compound as a pale yellow oily substance.

Step 2

5-(benzyloxy)-2-(methoxycarbonyl)-1-tetralone

Under an argon atmosphere, 2.09 g of 60% sodium hydride was suspended in 30 ml of anhydrous dioxane and 11.51 g of dimethyl carbonate was added. While stirring with heating in an oil bath at 80 to 85° C., a solution of 6.58 g of 5-(benzyloxy)-1-tetralone in 15 ml of dioxane was added dropwise over about one hour. After stirring for one hour, the reaction solution was ice-cooled and 52 ml of an aqueous 1N acetic acid solution was added dropwise. The reaction solution was diluted with water, extracted with diethyl ether, washed with water and dried over anhydrous magnesium sulfate, and then the solvent was evaporated under reduced pressure. The residue was purified by silica gel column chromatography to obtain 7.95 g of the desired compound as a pale yellow oily substance.

Step 3

5-(benzyloxy)-1-hydroxy-2-(methoxycarbonyl)-1,2,3,4-tetrahydronaphthalene

A solution of 7.95 g of 5-(benzyloxy)-2-(methoxycarbonyl)-1-tetralone in 80 ml of methanol was ice-cooled and 0.97 g of sodium borohydride was added in five portions. After stirring for 30 minutes, an ice bath was removed and the mixture was further stirred for 30 minutes. The reaction solution was diluted with iced water, extracted with diethyl ether, washed with water and dried over anhydrous magnesium sulfate, and then the solvent was evaporated under reduced pressured. The residue was purified by silica gel column chromatography to obtain 5.96 g of the desired compound as a colorless oily substance.

Step 4

5-(benzyloxy)-2-(methoxycarbonyl)-3,4-dihydronaphthalene

To a solution of 5.96 g of 5-(benzyloxy)-1-hydroxy-2-(methoxycarbonyl)-1,2,3,4-tetrahydronaphthalene in 23 ml of anhydrous pyridine, 4.37 g of p-toluenesulfonyl chloride was added. After stirring with heating at 70° C. for 3 hours, 0.72 g of p-toluenesulfonyl chloride was further added, followed by stirring for 1.5 hours. The reaction solution was extracted with diethyl ether after adding iced water. The extract was washed in turn with water, 10% hydrochloric acid, water and an aqueous saturated sodium hydrogen carbonate solution and dried over anhydrous magnesium sulfate, the solvent was evaporated under reduced pressure. The residue was purified by silica gel column chromatography to obtain 2.79 g of the desired compound as a colorless crystal having a melting point of 64 to 67° C.

Step 5

5-(benzyloxy)-2-(hydroxymethyl)-3,4-dihydronaphthalene

Under an argon atmosphere, to a solution of 2.79 g of 5-(benzyloxy)-2-(methoxycarbonyl)-3,4-dihydronaphthalene in 30 ml of dry dichloromethane, 24 ml of diisobutylaluminum hydride (1M toluene solution) was added dropwise at −70° C. or lower, followed by stirring for 20 minutes. To the reaction solution, 26 ml of an aqueous 10% sodium hydroxide solution was added dropwise and, after heating to room temperature, the mixture was extracted with diethyl ether. The extract was washed with saturated brine and dried over anhydrous magnesium sulfate, and then the solvent was evaporated under reduced pressure. The residue was purified by silica gel column chromatography to obtain 2.25 g of the desired compound as a colorless crystal having a melting point of 59 to 61° C.

Step 6

5-(benzyloxy)-2-(chloromethyl)-3,4-dihydronaphthalene

Under an argon atmosphere, to a solution of 1.82 g of 5-(benzyloxy)-2-(hydroxymethyl)-3,4-dihydronaphthalene and 0.55 g of 4-(dimethylamino)pyridine in 30 ml of dichloromethane, 1.43 g of p-toluenesulfonyl chloride was added. After 1.2 ml of triethylamine was added dropwise, the mixture was stirred at room temperature for 1.5 hours. The reaction solution was poured into iced water and then extracted with diethyl ether. The extract was washed in turn with 5% hydrochloric acid, water and an aqueous saturated sodium hydrogen carbonate solution and dried over anhydrous magnesium sulfate, and then the solvent was evaporated under reduced pressure. The residue was purified by silica gel column chromatography to obtain 1.06 g of the desired compound as a colorless oily substance.

REFERENCE EXAMPLE 20

1-bromo-4-[N-(5,6-diphenylpyrazin-2-yl)-N-isopropylamino]butane

A solution of 1.50 g of 4-[N-(5,6-diphenylpyrazin-2-yl)-N-isopropylamino]-1-butanol and 1.18 g of triphenylphosphine in 20 ml of dichloromethane was ice-cooled and 1.49 g of carbon tetrabromide was added. After stirring for one hour, the solvent was evaporated under reduced pressure. The residue was purified by silica gel column chromatography to obtain 1.18 g of the desired compound as a yellow oily substance.

REFERENCE EXAMPLE 21

5,6-bis(4-methoxyphenyl)-2-chloropyrazine

In the same manner as in the preparation of 2-chloro-5,6-diphenylpyrazine described in the document (J. Am. Chem. Soc., 74, 1580 (1952)), the desired compound was prepared. Melting point: 126 to 127° C.

In the same manner as in Reference Example 21, the following compounds were prepared.

5,6-bis(4-fluorophenyl)-2-chloropyrazine (melting point: 91 to 92° C.)

2-chloro-5,6-di-p-tolylpyrazine (melting point: 112 to 117° C.)

REFERENCE EXAMPLE 22

Isopropylsulfonamide

While stirring under ice cooling, to a solution of saturated ammonia in 40 ml of anhydrous tetrahydrofuran, 1.126 ml of isopropylsulfonyl chloride was slowly added dropwise. After stirring under ice cooling for 3 hours, the insoluble matter was removed by filtration and then the solvent was evaporated under reduced pressure. To the resulting oily substance, diethyl ether was added and the deposited crystal was collected by filtration and then dried under reduced pressure to obtain 0.71 g of the desired compound as a yellowish crystal having a melting point of 56 to 59° C.

REFERENCE EXAMPLE 23

4-methoxybenzenesulfonamide

In the same manner as in Reference Example 22, except that 4-methoxybenzenesulfonyl chloride was used in place of isopropylsulfonyl chloride, the desired compounds was obtained as a colorless crystal having a melting point of 110 to 112° C.

REFERENCE EXAMPLE 24

4-fluorobenzenesulfonamide

In the same manner as in Reference Example 22, except that 4-fluorobenzenesulfonyl chloride was used in place of isopropylsulfonyl chloride, the desired compound was obtained as a colorless crystal having a melting point of 123 to 125° C.

REFERENCE EXAMPLE 25

2-thiophenesulfonamide

In the same manner as in Reference Example 22, except that 2-thiophenesulfonyl chloride was used in place of isopropylsulfonyl chloride, the desired compound was obtained as a colorless crystal having a melting point of 144 to 145.5° C.

REFERENCE EXAMPLE 26

Morpholin-4-ylsulfonamide 5.00 g of sulfamide, 4.09 g of morpholine and 5 ml of 1,2-diethoxyethane were mixed and heated with stirring in an oil bath at 120° C. for 11 hours. The reaction solution was air-cooled to room temperature and the crystal was washed with diethyl ether, washed with methanol and then dried under reduced pressure to obtain 5.98 g of the desired compound as an brownish crystal having a melting point of 158 to 161° C.

REFERENCE EXAMPLE 27

Pyrrolidin-1-ylsulfonamide

In the same manner as in Reference Example 26, except that pyrrolidine was used in place of morpholine, the desired compound was obtained as a brownish crystal having a melting point of 94 to 97° C.

REFERENCE EXAMPLE 28

Sulfamic acid phenyl ester

To a solution of 4.98 g of phenol in 9 ml of toluene, a solution of 7.49 g of chlorosulfonyl isocyanate in 5 ml of toluene was added dropwise at an inner temperature of 45° C. or lower. After the completion of dropwise addition, the mixture was heated in an oil bath at 110° C. and continuously stirred for 12 hours. The reaction solution was ice-cooled and the insoluble matter was removed by filtration, and then the filtrate was heated in an oil bath at 40° C. While stirring vigorously, 1.2 ml of water was slowly added dropwise. The reaction solution was ice-cooled and the deposited crystal was collected by filtration, washed with toluene and then dried under reduced pressure to obtain 6.46 g of the desired compound as a colorless crystal having a melting point of 78 to 80° C.

EXAMPLE 1

2-{4-[N-(5,6-diphenylpyrazin-2-yl)-N-isopropylamino]butyloxy}acetic acid tert-butyl ester Step 1

4-[N-(5,6-diphenylpyrazin-2-yl)-N-isopropylamino]-1-butanol 30 g of 2-chloro-5,6-diphenylpyrazine and 131.22 g of 4-(isopropylamino)-1-butanol were mixed and then heated with stirring at 190° C. for 10 hours. The reaction solution was air-cooled, poured into water, extracted with diethyl ether, dried over anhydrous magnesium sulfate and then concentrated. The residue was purified by silica gel column chromatography to obtain 22.96 g of the desired compound as a colorless crystal having a melting point of 102 to 103° C.

Step 2

2-{4-[N-(5,6-diphenylpyrazin-2-yl)-N-isopropylamino]butyloxy}acetic Acid Tert-Butyl Ester 22.84 g of 4-[N-(5,6-diphenylpyrazin-2-yl)-N-isopropylamino]-1-butanol was dissolved in 160 ml of benzene and 10.73 g of tetra-n-butylammonium hydrogen sulfate and 160 ml of an aqueous 40% potassium hydroxide solution were added. While stirring vigorously under ice cooling, 10.73 g of tert-butyl bromoacetate was added dropwise so as to control the inner temperature within a range from 5 to 10° C. After stirring for 45 minutes, an ice bath was removed and the mixture was stirred at room temperature for one hour. The reaction solution was diluted with water and then extracted with diethyl ether. The extract was washed with water and dried over anhydrous magnesium sulfate, and then the solvent was evaporated under reduced pressure. The residue was purified by silica gel column chromatography to obtain 21.70 g of the desired compound as a pale yellow oily substance.

$^1$H-NMR (CDCl$_3$)δ: 1.27 (6H,d), 1.48 (9H,s), 1.55 to 1.90 (4H,m), 3.45 (2H,t), 3.58 (2H,t), 3.95 (2H,s), 4.82 (1H,qn), 7.17 to 7.50 (10H,m), 8.00 (1H,s)

EXAMPLE 2

2-{4-[N-(5,6-diphenylpyrazin-2-yl)-N-cyclopentylamino]butyloxy}acetic acid tert-butyl ester In the same manner as in Example 1, except that 4-(cyclopentylamino)-1-butanol was used in place of 4-(isopropylamino)-1-butanol, the desired compound was prepared as a pale yellow oily substance.

$^1$H-NMR (CDCl$_3$)δ: 1.48 (9H,s), 1.63 to 1.79 (10H,m), 1.98 to 2.00 (2H,m), 3.48 (2H,t), 3.57 (2H,t), 3.95 (2H,s), 4.66 to 4.76 (1H,m), 7.20 to 7.48 (10H,m), 8.02 (1H,s)

EXAMPLE 3

2-{4-[N-(5,6-diphenylpyrazin-2-yl)-N-cyclohexylamino]butyloxy}acetic acid tert-butyl ester In the same manner as in Example 1, except that 4-(cyclohexylamino)-1-butanol was used in place of 4-(isopropylamino)-1-butanol, the desired compound was prepared as a yellow oily substance.

$^1$H-NMR (CDCl$_3$)δ: 1.16 to 1.90 (14H,m), 1.48 (9H,s), 3.48 (2H,t), 3.57 (2H,t), 3.95 (2H,s), 4.25 to 4.35 (1H,m), 7.21 to 7.49 (10H,m), 7.99 (1H,s)

EXAMPLE 4

2-{4-[N-(5,6-di-p-tolylpyrazin-2-yl)-N-isopropylamino]butyloxy}acetic acid tert-butyl ester In the same manner as in Example 1, except that 2-chloro-5,6-di-p-tolylpyrazine was used in place of 2-chloro-5,6-diphenylpyrazine, the desired compound was prepared as a yellow oily substance.

$^1$H-NMR (CDCl$_3$)δ: 1.24 to 1.29 (6H,m), 1.48 (9H,s), 1.68 to 1.75 (4H,m), 2.32 (3H,s), 2.33 (3H,s), 3.42 (2H,t), 3.57 (2H,t), 3.95 (2H,s), 4.79 (1H,qn), 7.03 to 7.09 (4H,m), 7.24 to 7.29 (2H,m), 7.34 to 7.38 (2H,m), 7.96 (1H,s)

EXAMPLE 5

2-{4-[N-(5,6-diphenylpyridin-2-yl)-N-methylamino]butyloxy}acetic acid tert-butyl ester In the same manner as in Example 1, except that 2-chloro-5,6-diphenylpyridine was used in place of 2-chloro-5,6-diphenylpyrazine and 4-(methylamino)-1-butanol was used in place of 4-(isopropylamino)-1-butanol, provided that the reaction temperature of the step 1 was controlled within a range from 100 to 150° C., the desired compound was prepared as a pale brown oily product.

$^1$H-NMR (CDCl$_3$)δ: 1.47 (9H,s), 1.60 to 1.80 (4H,m), 3.12 (3H,s), 3.56 (2H,t), 3.66 (2H,t), 3.92 (2H,s), 6.52 (1H,dd), 7.10 to 7.53 (11H,m)

EXAMPLE 6

2-{4-[N-(3-chloro-5,6-diphenylpyrazin-2-yl)-N-isopropylamino]butyloxy}acetic acid tert-butyl ester In the same manner as in Example 1, except that 2,3-dichloro-5,6-diphenylpyrazine was used in place of 2-chloro-5,6-diphenylpyrazine, the desired compound was prepared as a pale yellow oily substance.

$^1$H-NMR (CDCl$_3$)δ: 1.20 to 1.30 (6H,m), 1.40 to 1.50 (9H,m), 1.50 to 1.80 (4H,m), 3.41 to 3.51 (4H,m), 3.89 (2H,s), 4.37 (1H,qn), 7.20 to 7.50 (10H,m)

EXAMPLE 7

2-{4-[N-(5,6-di-p-tolyl-1,2,4-triazin-3-yl)-N-isopropylamino]butyloxy}acetic acid tert-butyl ester In the same manner as in Example 1, except that 3-chloro-5,6-di-p-tolyl-1,2,4-triazine was used in place of 2-chloro-5,6-diphenylpyrazine, provided that the reaction temperature of the step 1 was controlled at 80° C. and the reaction time was controlled to 40 minutes, the desired compound was prepared as a yellowish brown oily substance.

$^1$H-NMR (CDCl$_3$)δ: 1.31 (6H,d), 1.48 (9H,s), 1.60 to 1.90 (4H,m), 2.35 (6H,s), 3.50 to 3.70 (4H,m), 3.95 (2H,s), 5.10 (1H,m), 7.11 (4H,d), 7.40 (4H,ddd)

EXAMPLE 8

2-{4-[N-(5,6-diphenyl-1,2,4-triazin-3-yl)-N-isopropylamino]butyloxy}acetic acid tert-butyl ester In the same manner as in Example 1, except that 3-chloro-5,6-diphenyl-1,2,4-triazine was used in place of 2-chloro-5,6-diphenylpyrazine, provided that the reaction temperature of the step 1 was controlled to 80° C. and the reaction time was controlled to 30 minutes, the desired compound was prepared as a pale yellow oily substance.

$^1$H-NMR (CDCl$_3$)δ: 1.32 (6H,d), 1.47 (9H,s), 1.60 to 1.90 (4H,m),3.50 to 3.70 (4H,m), 3.95 (2H,s), 5.11 (1H,m), 7.25 to 7.55 (10H,m)

2-{4-[N-(5,6-di-p-tolylpyrazin-2-yl)-N-methylamino]butyloxy}acetic acid tert-butyl ester Step 1

4-[N-(5,6-di-p-tolylpyrazin-2-yl)-N-methylamino]-1-butanol

To a solution of 3.00 g of 2-chloro-5,6-di-p-tolylpyrazine and 1.57 g of 4-(methylamino)-1-butanol in 15 ml of N,N-dimethylformamide, 2.26 g of potassium carbonate was added. After heating with stirring at 100° C. for 26 hours, the reaction solution was extracted with diethyl ether after adding ice water. The extract was washed in turn with water and saturated brine and dried over anhydrous magnesium sulfate, and then the solvent was evaporated under reduced pressure. The residue was purified by silica gel column chromatography and the resulting crystal was washed with diisopropyl ether to obtain 2.76 g of the desired compound as a colorless crystal having a melting point of 94 to 96° C.

Step 2

2-{4-[N-(5,6-di-p-tolylpyrazin-2-yl)-N-methylamino]butyloxy}acetic acid tert-butyl ester In the same manner as in the step 2 of Example 1, except that 4-[N-(5,6-di-p-tolylpyrazin-2-yl)-N-methylamino]-1-butanol obtained in the step 1 was used, the desired compound was prepared as a pale yellow oily substance.
$^1$H-NMR (CDCl$_3$)δ: 1.47 (9H,s), 1.59 to 1.90 (4H,m), 2.32 (3H,s), 2.33 (3H,s), 3.16 (3H,s), 3.55 (2H,t), 3.66 (2H,t), 3.93 (2H,s), 7.00 to 7.10 (4H,m), 7.20 to 7.40 (4H,m), 7.99 (1H,s)

EXAMPLE 10

2-[4-{N-[5,6-bis(4-methoxyphenyl)pyrazin-2-yl]-N-methylamino}butyloxy]acetic acid tert-butyl ester In the same manner as in Example 9, except that 5,6-bis(4-methoxyphenyl)-2-chloropyrazine was used in place of 2-chloro-5,6-di-p-tolylpyrazine, the desired compound was prepared as a pale yellow oily substance.
$^1$H-NMR (CDCl$_3$)δ: 1.47 (9H,s), 1.60 to 1.85 (4H,m), 3.16 (3H,s), 3.56 (2H,t), 3.66 (2H,t), 3.80 (3H,s), 3.81 (3H,s), 3.94 (2H,s), 6.75 to 6.85 (4H,m), 7.26 to 7.46 (4H,m), 7.96 (1H,s)

EXAMPLE 11

2-[4-{N-[5,6-bis(4-fluorophenyl)pyrazin-2-yl]-N-methylamino}butyloxy]acetic acid tert-butyl ester In the same manner as in Example 9, except that 5,6-bis(4-fluorophenyl)-2-chloropyrazine was used in place of 2-chloro-5,6-di-p-tolylpyrazine, the desired compound was prepared as a pale yellow oily substance.
$^1$H-NMR (CDCl$_3$)δ: 1.47 (9H,s), 1.61 to 1.90 (4H,m), 3.17 (3H,s), 3.56 (2H,t), 3.67 (2H,t), 3.93 (2H,s), 6.91 to 7.03 (4H,m), 7.26 to 7.45 (4H,m), 8.01 (1H,s)

EXAMPLE 12

2-{4-[N-(5,6-diphenyl-3-methylpyrazin-2-yl)-N-methylamino]butyloxy}acetic acid tert-butyl ester In the same manner as in Example 9, except that 2-chloro-5,6-diphenyl-3-methylpyrazine was used in place of 2-chloro-5,6-di-p-tolylpyrazine, the desired compound was prepared as a pale yellow crystal having a melting point of 48 to 51° C.

EXAMPLE 13

2-{2-[1-(5,6-diphenylpyrazin-2-yl)piperidine-4-yl]ethoxy}acetic acid tert-butyl ester In the same manner as in Example 9, except that 2-chloro-5,6-diphenylpyrazine was used in place of 2-chloro-5,6-di-p-tolylpyrazine and 2-(piperidine-4-yl)ethanol was used in place of 4-(methylamino)-1-butanol, the desired compound was prepared as a yellowish crystal having a melting point of 104 to 106° C.

EXAMPLE 14

(±)-2-{3-[1-(5,6-diphenylpyrazin-2-yl)pyrrolidin-2-yl]propyloxy}acetic acid tert-butyl ester In the same manner as in Example 9, except that 2-chloro-5,6-diphenylpyrazine was used in place of 2-chloro-5,6-di-p-tolylpyrazine and (O)-3-(2-pyrrolidinyl)-1-propanol was used in place of 4-(methylamino)-1-butanol, the desired compound was prepared as pale yellow oily substance.
$^1$H-NMR (CDCl$_3$)δ: 1.47 (9H,s), 1.50 to 2.20 (8H,m), 3.40 to 3.75 (4H,m), 3.93 (2H,s), 4.15 to 4.30 (1H,m), 7.20 to 7.50 (10H,m), 7.90 (1H,s)

EXAMPLE 15

2-{4-[N-(5,6-diphenyl-1,2,4-triazin-3-yl)-N-methylamino]butyloxy}acetic acid tert-butyl ester In the same manner as in Example 9, except that 3-chloro-5,6-diphenyl-1,2,4-triazine was used in place of 2-chloro-5,6-di-p-tolylpyrazine, provided that the reaction temperature of the step 1 was controlled to room temperature and the reaction time was controlled to 3 hours, the desired compound was prepared as a pale yellow oily substance.
$^1$H-NMR (CDCl$_3$)δ: 1.47 (9H,s), 1.60 to 1.90 (4H,m), 3.34 (3H,s), 3.57 (2H,t), 3.86 (2H,t), 3.94 (2H,s), 7.25 to 7.55 (10H,m)

EXAMPLE 16

(±)-2-{4-[1-(5,6-diphenylpyrazin-2-yl)pyrrolidin-2-yl]butyloxy}acetic acid tert-butyl ester Step 1

(±)-1-[1-(5,6-diphenylpyrazin-2-yl)pyrrolidin-2-yl]-4-(2-tetrahydropyranyloxy)butane In the same manner as in the step 1 of Example 9, except that 2-chloro-5,6-diphenylpyrazine was used in place of 2-chloro-5,6-di-p-tolylpyrazine and (±)-1-(2-pyrrolidinyl)-4-(2-tetrahydropyranyloxy)butane was used in place of 4-(methylamino)-1-butanol, the desired compound was prepared as a yellowish crystal having a melting point of 94 to 96° C.

Step 2

(±)-4-[1-(5,6-diphenylpyrazin-2-yl)pyrrolidin-2-yl]-1-butanol

To a solution of 1.25 g of (±)-1-[1-(5,6-diphenylpyrazin-2-yl)pyrrolidin-2-yl]-4-(2-tetrahydropyranyloxy)butane in 13 ml of methanol, 0.52 g of p-toluenesulfonic acid monohydrate was added, followed by stirring at room temperature for 3 hours. The reaction solution was alkalified by adding an aqueous saturated sodium hydrogen carbonate solution, and then extracted with ethyl acetate. The extract was dried over anhydrous magnesium sulfate and the solvent was evaporated under reduced pressure to obtain 1.10 g of the desired compound as a pale yellow oily substance.

Step 3

(±)-2-{4-[1-(5,6-diphenylpyrazin-2-yl)pyrrolidin-2-yl]butyloxy}acetic acid tert-butyl ester In the same manner as in the step 2 of Example 1, except that (±)-4-[1-(5,6-diphenylpyrazin-2-yl)pyrrolidin-2-yl]-1-butanol was used, the desired compound was prepared as a pale yellow oily substance.

$^1$H-NMR (CDCl$_3$)δ: 1.30 to 2.20 (10H,m), 1.47 (9H,s), 3.42 to 3.75 (4H,m), 3.92 (2H,s), 4.08 to 4.20 (1H,m), 7.20 to 7.50 (10H,m), 7.89 (1H,s)

EXAMPLE 17

(±)-2-{2-[1-(5,6-diphenylpyrazin-2-yl)piperidin-3-yl]ethoxy}acetic acid tert-butyl ester Step 1

(±)-3-[2-(tert-butyldimethylsilyloxy)ethyl]-1-(5,6-diphenylpyrazin-2-yl)piperidine In the same manner as in the step 1 of Example 9, except that 2-chloro-5,6-diphenylpyrazine was used in place of 2-chloro-5,6-di-p-tolylpyrazine and (±)-3-[2-(tert-butyldimethylsilyloxy)ethyl]piperidine was used in place of 4-(methylamino)-1-butanol, the desired compound was prepared.

Step 2

(±)-2-[1-(5,6-diphenylpyrazin-2-yl)piperidin-3-yl]ethanol

To a solution of 1.20 g of 3-[2-(tert-butyldimethylsilyloxy)ethyl]-1-(5,6-diphenylpyrazin-2-yl)piperidine in 6 ml of tetrahydrofuran, 5.0 ml of 1M tetra-n-butylammonium fluoride in tetrahydrofuran was added. After stirring at room temperature for 2 hours, the solvent was evaporated under reduced pressure. The residue was purified by silica gel column chromatography to obtain 0.77 g of the desired compound as a pale yellow amorphous.

Step 3

(±)-2-{2-[1-(5,6-diphenylpyrazin-2-yl)piperidin-3-yl]ethoxy}acetic acid tert-butyl ester In the same manner as in the step 2 of Example 1, except that (±)-2-[1-(5,6-diphenylpyrazin-2-yl)piperidin-3-yl]ethanol was used, the desired compound was prepared as a pale yellow oily substance.

$^1$H-NMR (CDCl$_3$)δ: 1.48 (9H,s), 1.53 to 1.99 (7H,m), 2.80 (1H,dd), 3.05 (1H,td), 3.63 (2H,t), 3.96 (2H,s), 4.28 to 4.38 (2H,m), 7.21 to 7.48 (10H,m), 8.17 (1H,s)

EXAMPLE 18

(R)-2-[3-{2-[N-(5,6-diphenylpyrazin-2-yl)-N-methylamino]-1-hydroxyethyl}phenoxy]acetic acid methyl ester Step 1

(R)-3-{2-[N-(5,6-diphenylpyrazin-2-yl)-N-methylamino]-1-hydroxyethyl}phenol

In the same manner as in the step 1 of Example 9, except that 2-chloro-5,6-diphenylpyrazine was used in place of 2-chloro-5,6-di-p-tolylpyrazine and L-phenylephrine was used in place of 4-(methylamino)-1-butanol, the desired compound was prepared as a pale brown amorphous.

Step 2

(R)-2-[3-{2-[N-(5,6-diphenylpyrazin-2-yl)-N-methylamino]-1-hydroxyethyl}phenoxy]acetic acid methyl ester To a solution of 0.66 g of (R)-3-{2-[N-(5,6-diphenylpyrazin-2-yl)-N-methylamino]-1-hydroxyethyl}phenol and 0.28 g of methyl bromoacetate in 10 ml of acetonitrile, 2 mg of potassium iodide and 0.28 g of potassium carbonate were added and the mixture was heated at reflux for 4 hours. The insoluble matter was removed by filtration and the filtrate was concentrated under reduced pressure. The residue was purified by silica gel column chromatography to obtain 0.55 g of the desired compound as a pale orange amorphous.

$^1$H-NMR (CDCl$_3$)δ: 3.04 (3H,s), 3.75 to 4.01 (2H,m), 3.78 (3H,s), 4.63 (2H,s), 5.02 to 5.17 (2H,m), 6.79 to 6.85 (1H,m), 7.00 to 7.05 (2H,m), 7.20 to 7.50 (11H,m), 8.10 (1H,s)

EXAMPLE 19

2-[3-{[N-(5,6-diphenylpyrazin-2-yl)-N-methylamino]methyl}phenoxy]acetic acid methyl ester Step 1

1-{[N-(5,6-diphenylpyrazin-2-yl)-N-methylamino]methyl}-3-(methoxymethoxy)benzene In the same manner as in the step 1 of Example 9, except that 2-chloro-5,6-diphenylpyrazine was used in place of 2-chloro-5,6-di-p-tolylpyrazine and 3-(methoxymethoxy)-N-methylbenzylamine was used in place of 4-(methylamino)-1-butanol, the desired compound was prepared as a colorless crystal having a melting point of 109 to 111° C.

Step 2

3-{[N-(5,6-diphenylpyrazin-2-yl)-N-methylamino]methyl}phenol

To a suspension of 0.91 g of 1-{[N-(5,6-diphenylpyrazin-2-yl)-N-methylamino]methyl}-3-(methoxymethoxy)benzene in 10 ml of methanol, 2 ml of a 18% hydrogen chloride-methanol solution was added. After stirring at room temperature for 2 hours, 1 ml of a 18% hydrogen chloride-methanol solution was further added and the mixture was continuously stirred for one hour. After the solvent was evaporated under reduced pressure, the reaction solution was neutralized by adding an aqueous saturated sodium hydrogen carbonate solution and then extracted with ethyl acetate. The crude crystal was washed with diethyl ether and then dried to obtain 0.66 g of the desired compound as a colorless crystal having a melting point of 156 to 157° C.

Step 3

2-[3-{[N-(5,6-diphenylpyrazin-2-yl)-N-methylamino]methyl}phenoxy]acetic acid methyl ester In the same manner as in the step 2 of Example 18, except that 3-{[N-(5,6-diphenylpyrazin-2-yl)-N-methylamino]methyl}phenol was used, the desired compound was prepared as colorless crystal having a melting point of 132 to 134° C.

EXAMPLE 20

2-[3-{2-[N-(5,6-diphenylpyrazin-2-yl)-N-methylamino]ethyl}phenoxy]acetic acid methyl ester Step 1

1-(benzyloxy)-3-{2-[N-(5,6-diphenylpyrazin-2-yl)-N-methylamino]ethyl}benzene

In the same manner as in the step 1 of Example 9, except that 2-chloro-5,6-diphenylpyrazine was used in place of 2-chloro-5,6-di-p-tolylpyrazine and 1-[3-(benzyloxy)phenyl]-2-(methylamino)ethane was used in place of 4-(methylamino)-1-butanol, the desired compound was prepared as a pale yellow crystal having a melting point of 78 to 78.5° C.

Step 2

3-{2-[N-(5,6-diphenylpyrazin-2-yl)-N-methylamino]ethyl}phenol

To 1.17 g of 1-(benzyloxy)-3-{2-[N-(5,6-diphenylpyrazin-2-yl)-N-methylamino]ethyl}benzene, 12 ml of ethanol and 6 ml of hydrochloric acid were added, followed by heating with stirring at 80° C. for 17 hours. The reaction solution was air-cooled to room temperature, neutralized with an aqueous saturated sodium hydrogen carbonate solution and then extracted with ethyl acetate. The extract was washed with water, dried over anhydrous magnesium sulfate, and then the solvent was evaporated under reduced pressure. The crude crystal was washed with diisopropyl ether and then dried to obtain 0.87 g of the desired compound as a pale yellow crystal having a melting point of 158 to 161° C.

Step 3

2-[3-{2-[N-(5,6-diphenylpyrazin-2-yl)-N-methylamino]ethyl}phenoxy]acetic acid methyl ester In the same manner as in the step 2 of Example 18, except that 3-{2-[N-(5,6-diphenylpyrazin-2-yl)-N-methylamino]ethyl}phenol was used, the desired compound was prepared as a pale yellow oily substance.

$^1$H-NMR (CDCl$_3$)δ: 2.94 (2H,t), 3.12 (3H,s), 3.79 (3H,s), 3.85 (2H,t), 4.59 (2H,s), 6.70 to 6.91 (3H,m), 7.18 to 7.50 (11H,m), 8.02 (1H,s)

EXAMPLE 21

1-[N-(5,6-diphenylpyrazin-2-yl)-N-methylamino]-4-(methoxycarbonylmethoxy)indane

Step 1

1-[N-(5,6-diphenylpyrazin-2-yl)-N-methylamino]-4-(methoxymethoxy)indane

In the same manner as in the step 1 of Example 9, except that 2-chloro-5,6-diphenylpyrazine was used in place of 2-chloro-5,6-di-p-tolylpyrazine and 1-methylamino-4-(methoxymethoxy)indane was use in place of 4-(methylamino)-1-butanol, the desired compound was prepared as a pale yellow oily substance.

Step 2

1-[N-(5,6-diphenylpyrazin-2-yl)-N-methylamino]-4-hydroxyindane 220 mg of 1-[N-(5,6-diphenylpyrazin-2-yl)-N-methylamino]-4-(methoxymethoxy)indane was dissolved in 2 ml of a 25% hydrogen chloride-ethyl acetate solution, followed by stirring at room temperature for 3 hours. After adding water, the reaction solution was neutralized with an aqueous saturated sodium hydrogen carbonate solution and then extracted with ethyl acetate. After drying over anhydrous magnesium sulfate, the solvent was evaporated under reduced pressure. The residue was purified by silica gel column chromatography to obtain 167 mg of the desired compound as a pale yellow oily substance.

Step 3

1-[N-(5,6-diphenylpyrazin-2-yl)-N-methylamino]-4-(methoxycarbonylmethoxy)indane

In the same manner as in the step 2 of Example 18, except that 1-[N-(5,6-diphenylpyrazin-2-yl)-N-methylamino]-4-hydroxyindane was used, the desired compound was prepared as a pale yellow oily substance.

EXAMPLE 22

2-{4-[N-(5,6-diphenylpyrazin-2-yl)-N-methylamino]butyloxy}acetic acid methyl ester Under an argon atmosphere, to a solution of 763 mg of 5,6-diphenyl-2-(methylamino)pyrazine in 4 ml of N,N-dimethylformamide, 140 mg of 60% sodium hydride was added, followed by stirring at 80° C. for 30 minutes. The reaction solution was ice-cooled and a solution of 657 mg of 2-(4-bromobutyloxy)acetic acid methyl ester in 2 ml of N,N-dimethylformamide was slowly added. After an ice bath was removed, the mixture was stirred at room temperature for 14 hours. The reaction solution was combined with ice water and extracted with ethyl acetate and, after the extract was washed with saturated brine and dried over anhydrous magnesium sulfate, the solvent was evaporated under reduced pressure. The residue was purified by silica gel column chromatography to obtain 240 mg of the desired compound as a pale yellow oily substance.

$^1$H-NMR (CDCl$_3$)δ: 1.65 to 1.85 (4H,m), 3.18 (3H,s), 3.58 (2H,t), 3.68 (2H,t), 3.75 (3H,s), 4.06 (2H,s), 7.20 to 7.50 (10H,m), 8.03 (1H,s)

EXAMPLE 23

7-[N-(5,6-diphenylpyrazin-2-yl)-N-methylamino]heptanoic acid ethyl ester

In the same manner as in Example 22, except that ethyl 7-bromoheptanoic acid ethyl ester was used in place of 2-(4-bromobutyloxy)acetic acid methyl ester, the desired compound was prepared as a pale yellow oily substance.

$^1$H-NMR (CDCl$_3$)δ: 1.25 (3H,t), 1.30 to 1.80 (8H,m), 2.28 (2H,t), 3.17 (3H,s), 3.61 (2H,t), 4.12 (2H,q), 7.20 to 7.50 (10H,m), 8.02 (1H,s)

EXAMPLE 24

8-[N-(5,6-diphenylpyrazin-2-yl)-N-methylamino]octanoic acid methyl ester

In the same manner as in Example 22, except that 8-bromooctanoic acid methyl ester was used in place of 2-(4-bromobutyloxy)acetic acid methyl ester, the desired compound was prepared as a pale yellow oily substance.

$^1$H-NMR (CDCl$_3$)δ: 1.20 to 1.40 (5H,m), 1.50 to 1.75 (5H,m), 2.29 (2H,t), 3.17 (3H,s), 3.60 (2H,t), 3.66 (3H,s), 7.20 to 7.50 (10H,m), 8.01 (1H,s)

EXAMPLE 25

9-[N-(5,6-diphenylpyrazin-2-yl)-N-methylamino]nonanoic acid methyl ester

In the same manner as in Example 22, except that 9-bromononanoic acid methyl ester was used in place of 2-(4-bromobutyloxy)acetic acid methyl ester, the desired compound was prepared as a pale yellow oily substance.

¹H-NMR (CDCl₃)δ: 1.20 to 1.40 (8H,m), 1.50 to 1.75 (4H,m), 2.29 (2H,t), 3.17 (3H,s), 3.60 (2H,t), 3.66 (3H,s), 7.20 to 7.50 (10H,m), 8.01 (1H,s)

EXAMPLE 26

6-[N-(5,6-diphenylpyrazin-2-yl)-N-methylamino]hexanoic acid ethyl ester

In the same manner as in Example 22, except that 6-bromohexanoic acid ethyl ester was used in place of 2-(4-bromobutyloxy)acetic acid methyl ester, the desired compound was prepared as a pale yellow oily substance.

¹H-NMR (CDCl₃)δ: 1.24 (3H,t), 1.30 to 1.50 (2H,m), 1.60 to 1.80 (4H,m), 2.30 (2H,t), 3.16 (3H,s), 3.62 (2H,t), 4.12 (2H,q), 7.20 to 7.50 (10H,m), 8.01 (1H,s)

EXAMPLE 27

2-{4-[N-(5,6-diphenylpyrazin-2-yl)-N-ethylamino]butyloxy}acetic acid tert-butyl ester In the same manner as in Example 22, except that 5,6-diphenyl-2-(ethylamino)pyrazine was used in place of 5,6-diphenyl-2-(methylamino)pyrazine and 2-(4-bromobutyloxy)acetic acid tert-butyl ester was used in place of 2-(4-bromobutyloxy)acetic acid methyl ester, the desired compound was prepared as a pale yellow oily substance.

¹H-NMR (CDCl₃)δ: 1.25 (3H,t), 1.47 (9H,s), 1.60 to 1.85 (4H,m), 3.55 to 3.70 (6H,m), 3.93 (2H,s), 7.20 to 7.50 (10H,m), 8.00 (1H,s)

EXAMPLE 28

2-{4-[N-allyl-N-(5,6-diphenylpyrazin-2-yl)amino]butyloxy}acetic acid tert-butyl ester In the same manner as in Example 22, except that 2-allylamino-5,6-diphenylpyrazine was used in place of 5,6-diphenyl-2-(methylamino)pyrazine and 2-(4-bromobutyloxy)acetic acid tert-butyl ester was used in place of 2-(4-bromobutyloxy)acetic acid methyl ester, the desired compound was prepared as a pale yellow oily substance.

¹H-NMR (CDCl₃)δ: 1.47 (9H,s), 1.60 to 1.85 (4H,m), 3.55 to 3.70 (4H,m), 3.93 (2H,s), 4.05 to 4.25 (2H,m), 5.15 to 5.30 (2H,m), 5.80 to 6.15 (1H,m), 7.2 to 7.50 (10H,m), 7.99 (1H,s)

EXAMPLE 29

2-{4-[N-(5,6-diphenylpyrazin-2-yl)-N-methylamino]-(Z)-2-buten-1-yloxy}acetic acid tert-butyl ester In the same manner as in Example 22, except that 2-[4-chloro-(Z)-2-buten-1-yloxy]acetic acid tert-butyl ester was used in place of 2-(4-bromobutyloxy)acetic acid methyl ester, the desired compound was prepared as a brown oily product.

¹H-NMR (CDCl₃)δ: 1.48 (9H,s), 3.16 (3H,s), 3.92 (2H,s), 4.24 (2H,d), 4.37 (2H,d), 5.60 to 5.90 (2H,m), 7.20 to 7.50 (10H,m), 8.05 (1H,s)

EXAMPLE 30

2-{4-[N-(5,6-diphenylpyrazin-2-yl)-N-methylamino]-(E)-2-buten-1-yloxy}acetic acid methyl ester In the same manner as in Example 22, except that 2-[4-chloro-(E)-2-buten-1-yloxy]acetic acid methyl ester was used in place of 2-(4-bromobutyloxy)acetic acid methyl ester, the desired compound was prepared as a pale yellow oily substance.

EXAMPLE 31

2,3-diphenyl-5-{N-[4-(tert-butoxycarbonylmethoxy)butyl]-N-methylamino}pyrazine 1-oxide In the same manner as in Example 22, except that 2,3-diphenyl-5-(methylamino)pyrazine 1-oxide was used in place of 5,6-diphenyl-2-(methylamino)pyrazine and 2-(4-bromobutyloxy)acetic acid tert-butyl ester was used in place of 2-(4-bromobutyloxy)acetic acid methyl ester, the desired compound was prepared as a pale yellow oily substance.

¹H-NMR (CDCl₃)δ: 1.48 (9H,s), 1.60 to 1.80 (4H,m), 3.11 (3H,s), 3.50 to 3.65 (4H,m), 3.94 (2H,s), 7.15 to 7.40 (10H,m), 7.75 (1H,s)

EXAMPLE 32

2-{4-[N-(4,5-diphenylpyrimidin-2-yl)-N-methylamino]butyloxy}acetic acid tert-butyl ester In the same manner as in Example 22, except that 4,5-diphenyl-2-(methylamino)pyrimidine was used in place of 5,6-diphenyl-2-(methylamino)pyrazine and 2-(4-bromobutyloxy)acetic acid tert-butyl ester was used in place of 2-(4-bromobutyloxy)acetic acid methyl ester, the desired compound was prepared as a pale yellow oily substance.

¹H-NMR (CDCl₃)δ: 1.47 (9H,s), 1.60 to 1.90 (4H,m), 3.24 (3H,s), 3.57 (2H,t), 3.77 (2H,t), 3.93 (2H,s), 7.10 to 7.45 (10H,m), 8.33 (1H,s)

EXAMPLE 33

2-{4-[N-(4,5-di-p-tolylpyrimidin-2-yl)-N-methylamino]butyloxy}acetic acid tert-butyl ester In the same manner as in Example 22, except that 4,5-di-p-tolyl-2-(methylamino)pyrimidine was used in place of 5,6-diphenyl-2-(methylamino)pyrazine and 2-(4-bromobutyloxy)acetic acid tert-butyl ester was used in place of 2-(4-bromobutyloxy)acetic acid methyl ester, the desired compound was prepared as a pale yellow oily substance.

¹H-NMR (CDCl₃)δ: 1.47 (9H,s), 1.60 to 1.90 (4H,m), 2.32 (3H,s), 2.34 (3H,s), 3.23 (3H,s), 3.56 (2H,t), 3.72 (2H,t), 3.93 (2H,s), 6.99 to 7.11 (6H,m), 7.34 (2H,d), 8.28 (1H,s)

EXAMPLE 34

2-{4-[(5,6-diphenylpyrazin-2-yl)thio]butyloxy}acetic acid tert-butyl ester

To a solution of 500 mg of 5,6-diphenyl-2-pyrazinethiol in 20 ml of acetone, 321 mg of sodium carbonate was added and a solution of 556 mg of 2-(4-bromobutyloxy)acetic acid tert-butyl ester in 2 ml of acetone was added dropwise while stirring under ice-cooling, followed by stirring at room temperature for 24 hours. The solvent was evaporated under reduced pressure, and then the residue was combined with water and extracted with ethyl acetate. The extract was washed with saturated brine and dried over anhydrous magnesium sulfate, and then the solvent was evaporated under reduced pressure. The residue was purified by silica gel column chromatography to obtain 701 mg of the desired compound as a pale yellow oily substance.

$^1$H-NMR (CDCl$_3$)δ: 1.47 (9H,s), 1.70 to 2.00 (4H,m), 3.31 (2H,t), 3.55 (2H,t), 3.92 (2H,s), 7.20 to 7.50 (10H,m), 8.44 (1H,s)

EXAMPLE 35

5-(tert-butoxycarbonylmethoxy)-2-{[N-(5,6-diphenylpyrazin-2-yl)-N-methylamino]methyl}-1,2,3,4-tetrahydronaphthalene Step 1

5-(benzyloxy)-2-{[N-(5,6-diphenylpyrazin-2-yl)-N-methylamino]methyl}-3,4-dihydronaphthalene Under an argon atmospshere, 0.97 g of 60% sodium hydride was suspended in anhydrous N,N-dimethylformamide and 0.97 g of 5,6-diphenyl-2-(methylamino)-pyrazine was added in three portions. After stirring at 80° C. for 30 minutes, the reaction solution was ice-cooled and a solution of 0.97 g of 5-(benzyloxy)-2-(chloromethyl)-3,4-dihydronaphthalene in 5 ml of anhydrous N,N-dimethylformamide was added dropwise. After stirring for 30 minutes, the reaction solution was diluted with ice water and then extracted with diethyl ether. The extract was washed with water and dried over anhydrous magnesium sulfate, and then the solvent was evaporated under reduced pressure. The residue was purified by silica gel column chromatography to obtain 1.81 g of the desired compound as a pale yellow amorphous.

Step 2

2-{[N-(5,6-diphenylpyrazin-2-yl)-N-methylamino]methyl}-5-hydroxy-1,2,3,4-tetrahydronaphthalene To 800 mg of 5-(benzyloxy)-2-{[N-(5,6-diphenylpyrazin-2-yl)-N-methylamino]methyl}-3,4-dihydronaphthalene, 18 ml of ethanol, 15 ml of ethyl acetate and 80 mg of 10% palladium-carbon were added and, after the mixture was hydrogenated under 3 atm at room temperature for 31 hours, the reaction was continued at 30° C. for 23 hours. The catalyst was removed by filtration and the filtrate was evaporated under reduced pressure. The residue was purified by silica gel column chromatography to obtain 443 mg of the desired compound as a pale yellow oily substance.

Step 3

5-(tert-butoxycarbonylmethoxy)-2-{[N-(5,6-diphenylpyrazin-2-yl)-N-methylamino]methyl}-1,2,3,4-tetrahydronaphthalene To a solution of 413 mg of 2-[N-(5,6-diphenylpyrazin-2-yl)-N-methyl(aminomethyl)]-5-hydroxy-1,2,3,4-tetrahydronaphthalene and 210 mg of tert-butyl bromoacetate in 10 ml of acetonitrile, a catalytic amount of potassium iodide and 163 mg of potassium carbonate were added and the mixture was heated at reflux for 4 hours. The insoluble matter was removed by filtration and the filtrate was concentrated under reduced pressure. The residue was purified by silica gel column chromatography to obtain 423 mg of the desired compound as a pale orange oily substance.

$^1$H-NMR (CDCl$_3$)δ: 1.40 to 1.60 (1H,m), 1.48 (9H,s), 1.95 to 3.15 (6H,m), 3.24 (3H,s), 3.53 to 3.80 (2H,m), 4.51 (2H,s), 6.52 (1H,d), 6.72 (1H,d), 7.04 (1H,t), 7.10 to 7.50 (10H,m), 8.06 (1H,s)

EXAMPLE 36

2-{4-[N-(5,6-diphenylpyrazin-2-yl)-N-isopropylamino]butylthio}acetic acid methyl ester 1.17 g of 1-bromo-4-[N-(5,6-diphenylpyrazin-2-yl)-N-isopropylamino]butane, 0.29 g of methyl thioglycolate, 0.46 g of potassium carbonate, a catalytic amount of potassium iodide and 27 ml of acetonitrile were mixed and the mixture was refluxed for 4 hours. The insoluble matter was removed by filtration and the solvent was evaporated under reduced pressure. The residue was purified by silica gel column chromatography to obtain 1.19 g of the desired compound as a pale yellow crystal having a melting point of 64 to 67° C.

EXAMPLE 37

2-{4-[N-(5,6-diphenylpyrazin-2-yl)-N-isopropylamino]butylsulfinyl]acetic acid methyl ester A solution of 600 mg of 2-{4-[N-(5,6-diphenylpyrazin-2-yl)-N-isopropylamino]butylthio}acetic acid methyl ester obtained in Example 36 in 10 ml of dichloromethane was ice-cooled and 329 mg of 70% m-chloroperoxybenzoic acid was added. After stirring under ice cooling for 2 hours, the reaction solution was diluted with an aqueous saturated sodium hydrogen carbonate solution and then extracted with ethyl acetate. The extract was washed with water and dried over anhydrous magnesium sulfate, and then the solvent was evaporated under reduced pressure. The residue was purified by silica gel column chromatography to obtain 385 mg of the desired compound as a yellowish crystal having a melting point of 128 to 130° C.

EXAMPLE 38

2-{4-[N-(5,6-diphenylpyrazin-2-yl)-N-isopropylamino]butylsulfonyl}acetic acid methyl ester According to silica gel column chromatography in Example 37, 163 mg of the desired compound was obtained as a pale yellow crystal having a melting point of 123 to 125° C.

EXAMPLE 39

2-[4-(5,6-diphenylpyrazin-2-sulfinyl)butyloxy]acetic acid tert-butyl ester

While stirring under ice cooling, to a solution of 350 mg of 2-{4-[(5,6-diphenylpyrazin-2-yl)thio]butyloxy}acetic acid tert-butyl ester obtained in Example 34 in 5 ml of chloroform, 191 mg of 70% m-chloroperoxybenzoic acid was added, followed by stirring for 2 hours. The reaction solution was combined with 20 ml of a 0.2N sodium hydroxide solution, extracted with chloroform and dried over anhydrous magnesium sulfate, and then the solvent was evaporated under reduced pressure. The residue was purified by silica gel column chromatography to obtain 145 mg of the desired compound as a pale yellow oily substance.

$^1$H-NMR (CDCl$_3$)δ: 1.46 (9H,s), 1.70 to 2.20 (4H,m), 3.05 to 3.40 (2H,m), 3.55 (2H,dd), 3.92 (2H,s), 7.20 to 7.55 (10H,m), 9.16 (1H,s)

EXAMPLE 40

2-[4-(5,6-diphenylpyrazin-2-sulfonyl)butyloxy]acetic acid tert-butyl ester

To a solution of 350 mg of 2-{4-[(5,6-diphenylpyrazin-2-yl)thio]butyloxy}acetic acid tert-butyl ester obtained in Example 34 in 5 ml of chloroform, 421 mg of 70% m-chloroperoxybenzoic acid was added, followed by stirring at room temperature for 19 hours. The reaction solution was combined with 20 ml of 0.2N sodium hydroxide solution, extracted with chloroform and dried over anhydrous magnesium sulfate, and then the solvent was evaporated under reduced pressure. The residue was purified by silica gel column chromatography to obtain 380 mg of the desired compound as a colorless crystal having a melting point of 88 to 90° C.

EXAMPLE 41

2-[5-(5,6-diphenylpyrazin-2-yl)pentyloxy]acetic acid tert-butyl ester

Step 1

5,6-diphenyl-2-[5-(2-tetrahydropyranyloxy)-1-pentyn-1-yl]pyrazine

To a solution of 1.58 g of 2-chloro-5,6-diphenylpyrazine in 10 ml of triethylamine, 1.20 g of 5-(2-tetrahydropyranyloxy)-1-pentyne, 208 mg of dichlorobis(triphenylphosphine)palladium (II) and 56 mg of copper (I) iodide were added, followed by stirring under an argon atmosphere at 80° C. for 8 hours. The solvent was evaporated under reduced pressure and the residue was dissolved in diethyl ether, and then the insoluble matter was removed by filtration through celite. After the solvent was evaporated under reduced pressure, the residue was purified by silica gel column chromatography to obtain 1.79 g of the desired compound as a brown oily substance.

Step 2

5,6-diphenyl-2-(5-hydroxy-1-pentyn-1-yl)pyrazine

To a solution of 1.79 g of 5,6-diphenyl-2-[5-(2-tetrahydropyranyloxy)-1-pentyn-1-yl]pyrazine in methanol, 1.13 g of pyridinium p-toluenesulfonate was added and the mixture was heated at reflux for 30 minutes. The reaction solution was poured into ice water while stirring, extracted with ethyl acetate and then dried over anhydrous magnesium sulfate. After the solvent was evaporated under reduced pressure, the resulting crystal was recrystallized from diisopropyl ether to obtain 1.00 g of the desired compound as a yellow crystal having a melting point of 88 to 90° C.

Step 3

5,6-diphenyl-2-(5-hydroxypentan-1-yl)pyrazine

To a solution of 400 mg of 5,6-diphenyl-2-(5-hydroxy-1-pentyn-1-yl)pyrazine in 20 ml of ethanol, 80 mg of 5% palladium-carbon was added and the mixture was hydrogenated at 30° C. for 5 hours. After 40 mg of 5% palladium-carbon was further added, hydrogenation was continued for one hour. The catalyst was removed by filtering the reaction solution through celite and the filtrate was dried over anhydrous magnesium sulfate, and then the solvent was evaporated under reduced pressure to obtain 398 mg of the desired compound as a yellow oily substance.

Step 4

2-[5-(5,6-diphenylpyrazin-2-yl)pentyloxy]acetic acid tert-butyl ester

In the same manner as in the step 2 of Example 1, except that 5,6-diphenyl-2-(5-hydroxypentan-1-yl)pyrazine was used in place of 4-[N-(5,6-diphenylpyrazin-2-yl)-N-isopropylamino]-1-butanol, the desired compound was prepared as a pale yellow oily substance.

$^1$H-NMR (CDCl$_3$)δ: 1.40 to 2.00 (6H,m), 1.48 (9H,s), 2.92 (2H,t), 3.54 (2H,t), 3.95 (2H,s), 7.20 to 7.50 (10H,m), 8.46 (1H,s)

EXAMPLE 42

2-{4-[N-(5,6-diphenylpyrazin-2-yl)-N-isopropylamino]butyloxy}acetic acid 21.07 g of 2-{4-[N-(5,6-diphenylpyrazin-2-yl)-N-isopropylamino]butyloxy}acetic acid tert-butyl ester was dissolved in 200 ml of methanol and 60 ml of 1N sodium hydroxide solution was added. After the mixture was heated at reflux for 2 hours, the solvent was evaporated under reduced pressure and the residue was dissolved in water. After washing with diethyl ether, the aqueous layer was neutralized with 60 ml of 1N hydrochloric acid and then extracted with ethyl acetate. The extract was dried over anhydrous magnesium sulfate and the solvent was evaporated under reduced pressure, and then the residue was washed with diisopropyl ether to obtain 15.82 g of the desired compound.

Elemental analysis (for $C_{25}H_{29}N_3O_3$) Calcd. (%): C, 71.58; H, 6.97; N, 10.02. Found (%): C, 71.66; H, 7.03; N, 9.92.

EXAMPLE 43

2-{4-[N-(5,6-diphenylpyrazin-2-yl)-N-cyclopentylamino]butyloxy}acetic acid

In the same manner as in Example 42, except that 2-{4-[N-(5,6-diphenylpyrazin-2-yl)-N-cyclopentylamino]butyloxy}acetic acid tert-butyl ester was used, the desired compound was prepared as a pale yellow crystal having a melting point of 101 to 103° C.

Elemental analysis (for $C_{27}H_{31}N_3O_3$) Calcd. (%): C, 72.78; H, 7.01; N, 9.43. Found (%): C, 72.20; H, 7.26; N, 9.17.

EXAMPLE 44

2-{4-[N-(5,6-diphenylpyrazin-2-yl)-N-cyclohexylamino]butyloxy}acetic acid

In the same manner as in Example 42, except that 2-{4-[N-(5,6-diphenylpyrazin-2-yl)-N-cyclohexylamino]butyloxy}acetic acid tert-butyl ester was used, the desired compound was prepared as a pale yellow crystal having a melting point of 130 to 131° C.

Elemental analysis (for $C_{28}H_{33}N_3O_3$) Calcd. (%): C, 73.18; H, 7.24; N, 9.14. Found (%): C, 73.03; H, 7.34; N, 8.97.

EXAMPLE 45

2-{4-[N-(5,6-di-p-tolylpyrazin-2-yl)-N-isopropylamino]butyloxy}acetic acid

In the same manner as in Example 42, except that 2-{4-[N-(5,6-di-p-tolylpyrazin-2-yl)-N-isopropylamino]butyloxy}acetic acid tert-butyl ester was used, the desired compound was prepared as a pale yellow crystal having a melting point of 155 to 156° C.

Elemental analysis (for $C_{27}H_{33}N_3O_3$) Calcd. (%): C, 72.62; H, 7.22; N, 9.41. Found (%): C, 72.61; H, 7.55; N, 9.12.

EXAMPLE 46

2-{4-[N-(5,6-diphenylpyridin-2-yl)-N-methylamino]butyloxy}acetic acid sodium salt After 2-{4-[N-(5,6-diphenylpyridin-2-yl)-N-methylamino]butyloxy}acetic acid tert-butyl ester was hydrolyzed in the same manner as in Example 42, the resulting 2-{4-[N-(5,6-diphenylpyridin-2-yl)-N-methylamino]butyloxy}acetic acid was treated with the same amount of 1N sodium hydroxide solution to obtain the desired compound as a pale brown amorphous.

Elemental analysis (for $C_{24}H_{25}N_2O_3Na \cdot 0.4H_2O$) Calcd. (%): C, 68.69; H, 6.20; N, 6.68. Found (%): C, 68.69; H, 6.36; N, 6.36.

EXAMPLE 47

2-{4-[N-(3-chloro-5,6-diphenylpyrazin-2-yl)-N-isopropylamino]butyloxy}acetic acid 218 mg of 2-{4-[N-(3-chloro-5,6-diphenylpyrazin-2-yl)-N-isopropylamino]butyloxy}acetic acid tert-butyl ester was dissolved in 2 ml of 1,4-dioxane and 2 ml of 1N hydrochloric acid was added, followed by stirring at 80° C. for one hour. The mixture was further stirred at 110° C. for 4 hours. The reaction solution was neutralized with 1N sodium hydroxide solution and then extracted with ethyl acetate. The extract was dried over anhydrous magnesium sulfate and then the solvent was evaporated under reduced pressure. The resulting crude crystal was washed with a solvent of hexane-ethyl acetate (4:1) to obtain 120 mg of the desired product as a gray crystal having a melting point of 136 to 138° C.

Elemental analysis (for $C_{25}H_{28}ClN_3O_3$) Calcd. (%): C, 66.14; H, 6.22; N, 9.26. Found (%): C, 66.10; H, 6.32; N, 9.05.

EXAMPLE 48

2-{4-[N-(5,6-di-p-tolyl-1,2,4-triazin-3-yl)-N-isopropylamino]butyloxy}acetic acid In the same manner as in Example 42, except that 2-{4-[N-(5,6-di-p-tolyl-1,2,4-triazin-3-yl)-N-isopropylamino]butyloxy}acetic acid tert-butyl ester was used, the desired compound was prepared as a yellow crystal having a melting point of 119 to 121° C.

Elemental analysis (for $C_{26}H_{32}N_4O_3$) Calcd. (%): C, 69.62; H, 7.19; N, 12.49. Found (%): C, 69.44; H, 7.15; N, 12.45.

EXAMPLE 49

2-{4-[N-(5,6-diphenyl-1,2,4-triazin-3-yl)-N-isopropylamino]butyloxy}acetic acid

In the same manner as in Example 47, except that 2-{4-[N-(5,6-diphenyl-1,2,4-triazin-3-yl)-N-isopropylamino]butyloxy}acetic acid tert-butyl ester was used, the desired compound was prepared as a yellow crystal having a melting point of 128 to 130° C.

Elemental analysis (for $C_{24}H_{28}N_4O_3$) Calcd. (%): C, 68.55; H, 6.71; N, 13.32. Found (%): C, 68.44; H, 6.64; N, 13.21.

EXAMPLE 50

2-{4-[N-(5,6-di-p-tolylpyrazin-2-yl)-N-methylamino]butyloxy}acetic acid

In the same manner as in Example 42, except that 2-{4-[N-(5,6-di-p-tolylpyrazin-2-yl)-N-methylamino]butyloxy}acetic acid tert-butyl ester was used, the desired compound was prepared as a pale yellow crystal having a melting point of 161 to 162° C.

Elemental analysis (for $C_{25}H_{29}N_3O_3$) Calcd. (%): C, 71.58; H, 6.97; N, 10.02. Found (%): C, 71.46; H, 6.97; N, 9.91.

EXAMPLE 51

2-[4-{N-[5,6-bis(4-methoxyphenyl)pyrazin-2-yl]-N-methylamino}butyloxy]acetic acid In the same manner as in Example 42, except that 2-{4-[N-[5,6-bis(4-methoxyphenyl)pyrazin-2-yl]-N-methylamino]butyloxy}acetic acid tert-butyl ester was used, the desired compound was prepared as a pale yellow crystal having a melting point of 128 to 130° C.

Elemental analysis (for $C_{25}H_{29}N_3O_5$) Calcd. (%): C, 66.50; H, 6.47; N, 9.31. Found (%): C, 66.42; H, 6.36; N, 9.18.

EXAMPLE 52

2-[4-{N-[5,6-bis(4-fluorophenyl)pyrazin-2-yl]-N-methylamino}butyloxy]acetic acid In the same manner as in Example 42, except that 2-[4-{N-[5,6-bis(4-fluorophenyl)pyrazin-2-yl]-N-methylamino}butyloxy]acetic acid tert-butyl ester was used, the desired compound was prepared as a pale yellow crystal having a melting point of 116 to 118° C.

Elemental analysis (for $C_{23}H_{23}F_2N_3O_3$) Calcd. (%): C, 64.63; H, 5.42; N, 9.83. Found (%): C, 64.76; H, 5.45; N, 9.61.

EXAMPLE 53

2-{4-[N-(5,6-diphenyl-3-methylpyrazin-2-yl)-N-methylamino]butyloxy}acetic acid sodium salt After 2-{4-[N-(5,6-diphenyl-3-methylpyrazin-2-yl)-N-methylamino]butyloxy}acetic acid tert-butyl ester was hydrolyzed in the same manner as in Example 42, the resulting 2-{4-[N-(5,6-diphenyl-3-methylpyrazin-2-yl)-N-methylamino]butyloxy}acetic acid was treated with the same amount of 1N sodium hydroxide solution to obtain the desired compound as a brownish amorphous.

Elemental analysis (for $C_{24}H_{26}N_3O_3Na \cdot 0.4H_2O$) Calcd. (%): C, 66.32; H, 6.21; N, 9.67. Found (%): C, 66.59; H, 6.67; N, 9.63.

EXAMPLE 54

2-{2-[1-(5,6-diphenylpyrazin-2-yl)piperidin-4-yl]ethoxy}acetic acid

In the same manner as in Example 42, except that 2-{2-[1-(5,6-diphenylpyrazin-2-yl)piperidin-4-yl]ethoxy}acetic acid tert-butyl ester was used, the desired compound was prepared as a pale yellow crystal having a melting point of 173 to 174° C.

Elemental analysis (for $C_{25}H_{27}N_3O_3$) Calcd. (%): C, 71.92; H, 6.52; N, 10.06. Found (%): C, 71.62; H, 6.53; N, 9.79.

EXAMPLE 55

(±)-2-{3-[1-(5,6-diphenylpyrazin-2-yl)pyrrolidin-2-yl]propyloxy}acetic acid

In the same manner as in Example 42, except that (±)-2-{3-[1-(5,6-diphenylpyrazin-2-yl)pyrrolidin-2-yl]propyloxy}acetic acid tert-butyl ester was used, the desired compound was prepared as a pale yellow crystal having a melting point of 137 to 139° C.

Elemental analysis (for $C_{25}H_{27}N_3O_3$) Calcd. (%): C, 71.92; H, 6.52; N, 10.06. Found (%): C, 72.01; H, 6.56; N, 9.80.

EXAMPLE 56

2-{4-[N-(5,6-diphenyl-1,2,4-triazin-3-yl)-N-methylamino]butyloxy}acetic acid

In the same manner as in Example 47, except that 2-{4-[N-(5,6-diphenyl-1,2,4-triazin-3-yl)-N-methylamino]butyloxy}acetic acid tert-butyl ester was used, the desired compound was prepared as a yellow crystal having a melting point of 108 to 110° C.

Elemental analysis (for $C_{22}H_{24}N_4O_3$) Calcd. (%): C, 67.33; H, 6.16; N, 14.28. Found (%): C, 67.38; H, 6.22; N, 14.22.

EXAMPLE 57

(±)-2-{4-[1-(5,6-diphenylpyrazin-2-yl)pyrrolidin-2-yl]butyloxy}acetic acid

In the same manner as in Example 42, except that (±)-2-{4-[1-(5,6-diphenylpyrazin-2-yl)pyrrolidin-2-yl]butyloxy}acetic acid tert-butyl ester was used, the desired compound was prepared as a pale yellow crystal having a melting point of 138 to 140° C.

Elemental analysis (for $C_{26}H_{29}N_3O_3$) Calcd. (%): C, 72.37; H, 6.77; N, 9.74. Found (%): C, 72.35; H, 6.85; N, 9.50.

EXAMPLE 58

(±)-2-{2-[1-(5,6-diphenylpyrazin-2-yl)piperidin-3-yl]ethoxy}acetic acid

In the same manner as in Example 42, except that (±)-2-{2-[1-(5,6-diphenylpyrazin-2-yl)piperidin-3-yl]ethoxy}acetic acid tert-butyl ester was used, the desired compound was prepared as a pale yellow crystal having a melting point of 139 to 140° C.

Elemental analysis (for $C_{25}H_{27}N_3O_3$) Calcd. (%): C, 71.92; H, 6.52; N, 10.06. Found (%): C, 71.99; H, 6.60; N, 10.00.

EXAMPLE 59

(R)-(+)-2-[3-{2-[N-(5,6-diphenylpyrazin-2-yl)-N-methylamino]-1-hydroxyethyl}phenoxy]acetic acid In the same manner as in Example 42, except that (R)-2-[3-{2-[N-(5,6-diphenylpyrazin-2-yl)-N-methylamino]-1-hydroxyethyl}phenoxy]acetic acid methyl ester was used, the desired compound was prepared as a pale yellow crystal having a melting point of 158 to 159° C.

$[\alpha]D^{20}$: +40.86 (c=0.465, methanol)

Elemental analysis (for $C_{27}H_{25}N_3O_4$) Calcd. (%): C, 71.19; H, 5.53; N, 9.22. Found (%): C, 71.21; H, 5.58; N, 9.17.

EXAMPLE 60

2-[3-1[N-(5,6-diphenylpyrazin-2-yl)-N-methylamino]methyl}phenoxy]acetic acid

In the same manner as in Example 42, except that 2-[3-{[N-(5,6-diphenylpyrazin-2-yl)-N-methylamino]methyl}phenoxy]acetic acid methyl ester was used, the desired compound was prepared as a yellowish crystal having a melting point of 182 to 187° C.

Elemental analysis (for $C_{26}H_{23}N_3O_3$) Calcd. (%): C, 73.39; H, 5.45; N, 9.88. Found (%): C, 73.26; H, 5.47; N, 9.83.

EXAMPLE 61

2-[3-{2-[N-(5,6-diphenylpyrazin-2-yl)-N-methylamino]ethyl}phenoxy]acetic acid

In the same manner as in Example 42, except that 2-[3-{2-[N-(5,6-diphenylpyrazin-2-yl)-N-methylamino]ethyl}phenoxy]acetic acid methyl ester was used, the desired compound was prepared as a yellowish crystal having a melting point of 174 to 176° C.

Elemental analysis (for $C_{27}H_{25}N_3O_3$) Calcd. (%): C, 73.79; H, 5.73; N, 9.56. Found (%): C, 73.43; H, 5.79; N, 9.32.

EXAMPLE 62

4-(carboxymethoxy)-1-[N-(5,6-diphenylpyrazin-2-yl)-N-methylamino]indane

In the same manner as in Example 42, except that 1-[N-(5,6-diphenylpyrazin-2-yl)-N-methylamino]-4-(methoxycarbonylmethoxy)indane was used, the desired compound was prepared as a pale yellow crystal having a melting point of 182 to 184° C.

Elemental analysis (for $C_{28}H_{25}N_3O_3$) Calcd. (%): C, 74.48; H, 5.58; N, 9.31. Found (%): C, 74.06; H, 5.70; N, 9.09.

EXAMPLE 63

2-[4-(5,6-diphenylpyrazin-2-yloxy)butoxy]acetic acid sodium salt

Step 1

1-(5,6-diphenylpyrazin-2-yloxy)-4-(2-tetrahydropyranyloxy)butane 1.57 g of 4-(2-tetrahydropyranyloxy)-1-butanol was dissolved in 20 ml of tetrahydrofuran and 360 mg of 60% sodium hydride was added under ice cooling, followed by stirring at room temperature for 1.5 hours. The mixture was refluxed for 30 minutes and ice-cooled again and 2.00 g of 5-chloro-2,3-diphenylpyrazine was added. After stirring for 40 minutes, the mixture was heated to 80° C., stirred at the same temperature for 4.5 hours and then stirred at room temperature for 88 hours. The reaction solution was combined with ice water, extracted with ethyl acetate and then washed with saturated brine. The extract was dried over anhydrous magnesium sulfate and the solvent was evaporated under reduced pressure to obtain 2.39 g of the desired compound as an oily substance.

Step 2

4-(5,6-diphenylpyrazin-2-yloxy)-1-butanol 2.39 g of 1-(5,6-diphenylpyrazin-2-yloxy)-4-(2-tetrahydropyranyloxy)butane was dissolved in methanol and 1.53 g of pyridium p-toluenesulfonate was added, and then the mixture was refluxed for 30 minutes. The reaction solution was cooled, poured into ice water while stirring and then extracted with ethyl acetate. The extract was dried over anhydrous magnesium sulfate and the solvent was evaporated under reduced pressure to obtain 1.74 g of the desired compound as a colorless crystal having a melting point of 93 to 95° C.

Step 3

2-[4-(5,6-diphenylpyrazin-2-yloxy)butoxy]acetic acid sodium salt 500 mg of 4-(5,6-diphenylpyrazin-2-yloxy)-1-butanol was dissolved in 3 ml of tert-butanol and 420 mg of potassium tert-butoxide was added, and then a solution of 222 mg of chloroacetic acid in 1 ml of tert-butanol was added under reflux. After 3 ml of tert-butanol was added, the mixture was refluxed for 15 hours. After ice water was added and the pH was adjusted to 4 using 1N hydrochloric acid, the reaction solution was extracted with ethyl acetate. The extract was dried over anhydrous magnesium sulfate and the solvent was evaporated under reduced pressure. The resulting oily substance was dissolved in a solvent of benzene:methanol=4:1 and excess 2M trimethylsilyldiazomethane (hexane solution) was added to form a methyl ester. The solvent was evaporated under reduced pressure and the residue was purified by silica gel column chromatography to obtain 88 mg of an ester as an oily substance. The ester was dissolved in 1 ml of methanol and 1 ml of 1N sodium hydroxide solution was added, followed by refluxing for one hour. After the solvent was evaporated under reduced pressure, the residue was combined with water, washed with ethyl acetate, neutralized with 1 ml of 1N hydrochloric acid and then extracted with ethyl acetate. The extract was dried over anhydrous magnesium sulfate and the solvent was evaporated under reduced pressure. The resulting oily substance was dissolved in methanol and the same amount of 1N sodium hydroxide solution was added, and then the solvent was evaporated under reduced pressure to obtain 60 mg of the desired compound as a colorless amorphous.

Elemental analysis (for $C_{28}H_{25}N_3O_3 \cdot 1.1H_2O$) Calcd. (%): C, 62.88; H, 5.56; N, 6.67. Found (%): C, 63.07; H, 5.51; N, 6.28.

EXAMPLE 64

2-{4-[N-(5,6-diphenylpyrazin-2-yl)-N-methylamino]butyloxy}acetic acid

In the same manner as in Example 42, except that 2-{4-[N-(5,6-diphenylpyrazin-2-yl)-N-methylamino]butyloxy}acetic acid methyl ester was used, the desired compound was prepared.

Elemental analysis (for $C_{23}H_{25}N_3O_3$) Calcd. (%): C, 70.57; H, 6.44; N, 10.73. Found (%): C, 70.44; H, 6.42; N, 10.64.

EXAMPLE 65

7-[N-(5,6-diphenylpyrazin-2-yl)-N-methylamino]heptanoic acid

In the same manner as in Example 42, except that 7-[N-(5,6-diphenylpyrazin-2-yl)-N-methylamino]heptanoic acid methyl ester was used, the desired compound was prepared as a colorless crystal having a melting point of 114 to 118° C.

Elemental analysis (for $C_{24}H_{27}N_3O_2 \cdot 0.2H_2O$) Calcd. (%): C, 73.33; H, 7.03; N, 10.69. Found (%): C, 73.32; H, 7.06; N, 10.41.

EXAMPLE 66

8-[N-(5,6-diphenylpyrazin-2-yl)-N-methylamino]octanoic acid

In the same manner as in Example 42, except that 8-[N-(5,6-diphenylpyrazin-2-yl)-N-methylamino]octanoic acid methyl ester was used, the desired compound was prepared as a colorless crystal having a melting point of 116 to 117° C.

Elemental analysis (for $C_{25}H_{29}N_3O_2$) Calcd. (%): C, 74.41; H, 7.24; N, 10.41. Found (%): C, 74.16; H, 7.25; N, 10.29.

EXAMPLE 67

9-[N-(5,6-diphenylpyrazin-2-yl)-N-methylamino]nonanoic acid

In the same manner as in Example 42, except that 9-[N-(5,6-diphenylpyrazin-2-yl)-N-methylamino]nonanoic acid methyl ester was used, the desired compound was prepared as a colorless crystal having a melting point of 103 to 105° C.

Elemental analysis (for $C_{26}H_{31}N_3O_2 \cdot 0.3H_2O$) Calcd. (%): C, 73.83; H, 7.53; N, 9.93. Found (%): C, 73.80; H, 7.55; N, 9.65.

EXAMPLE 68

6-[N-(5,6-diphenylpyrazin-2-yl)-N-methylamino]hexanoic acid

In the same manner as in Example 42, except that 6-[N-(5,6-diphenylpyrazin-2-yl)-N-methylamino]hexanoic acid ethyl ester was used, the desired compound was prepared as a colorless crystal having a melting point of 159 to 160° C.

EXAMPLE 69

2-{4-[N-(5,6-diphenylpyrazin-2-yl)-N-ethylamino]butyloxy}acetic acid sodium salt Using 2-{4-[N-(5,6-diphenylpyrazin-2-yl)-N-ethylamino]butyloxy}acetic acid tert-butyl ester, carboxylic acid was formed in the same manner as in Example 42 and the resulting carboxylic acid was treated with the same amount of 1N sodium hydroxide solution to obtain the desired compound as a pale yellow amorphous.

Elemental analysis (for $C_{24}H_{26}N_3O_3Na \cdot 1H_2O$) Calcd. (%): C, 64.71; H, 6.34; N, 9.43. Found (%): C, 64.88; H, 6.25; N, 9.16.

EXAMPLE 70

2-{4-[N-allyl-N-(5,6-diphenylpyrazin-2-yl)amino]butyloxy}acetic acid sodium salt Using 2-{4-[N-allyl-N-(5,6-diphenylpyrazin-2-yl)amino]butyloxy}acetic acid tert-butyl ester, carboxylic acid was formed in the same manner as in Example 42 and the resulting carboxylic acid was treated with the same amount of 1N sodium hydroxide solution to obtain the desired compound as a colorless amorphous.

Elemental analysis (for $C_{25}H_{26}N_3O_3Na \cdot 0.7H_2O$) Calcd. (%): C, 66.42; H, 6.11; N, 9.29. Found (%): C, 66.31; H, 5.97; N, 8.98.

EXAMPLE 71

2-{4-[N-(5,6-diphenylpyrazin-2-yl)-N-methylamino]-(Z)-2-buten-1-yloxy]acetic acid In the same manner as in Example 42, except that 2-{4-[N-(5,6-diphenylpyrazin-2-yl)-N-methylamino]-(Z)-2-buten-1-yloxy]acetic acid tert-butyl ester was used, the desired compound was prepared as a pale yellow crystal having a melting point of 148 to 150° C.

Elemental analysis (for $C_{23}H_{23}N_3O_3$) Calcd. (%): C, 70.93; H, 5.95; N, 10.79. Found (%): C, 70.71; H, 6.00; N, 10.67.

EXAMPLE 72

2-{4-[N-(5,6-diphenylpyrazin-2-yl)-N-methylamino]-(E)-2-buten-1-yloxy]acetic acid In the same manner as in Example 42, except that 2-{4-[N-(5,6-diphenylpyrazin-2-yl)-N-methylamino]-(E)-2-buten-1-yloxy]acetic acid methyl ester was used, the desired compound was prepared as a pale yellow crystal having a melting point of 128 to 130° C.

Elemental analysis (for $C_{23}H_{23}N_3O_3 \cdot 0.2H_2O$) Calcd. (%): C, 70.28; H, 6.00; N, 10.69. Found (%): C, 70.33; H, 5.94; N, 10.46.

EXAMPLE 73

2,3-diphenyl-5-{N-[4-(carboxymethoxy)butyl]-N-methylamino}pyrazine 1-oxide

In the same manner as in Example 42, except that 2,3-diphenyl-5-{N-[4-(tert-butoxycarbonylmethoxy)butyl]-N-methylamino}pyrazine 1-oxide was used, the desired compound was prepared as a colorless crystal having a melting point of 185 to 190° C.

Elemental analysis (for $C_{23}H_{25}N_3O_4$) Calcd. (%): C, 67.80; H, 6.18; N, 10.31. Found (%): C, 67.54; H, 6.18; N, 10.15.

EXAMPLE 74

2-{4-[N-(4,5-diphenylpyrimidin-2-yl)-N-methylamino]butyloxy}acetic acid

In the same manner as in Example 42, except that 2-{4-[N-(4,5-diphenylpyrimidin-2-yl)-N-methylamino]butyloxy}acetic acid tert-butyl ester was used, the desired compound was prepared.

Elemental analysis (for $C_{23}H_{25}N_3O_3$) Calcd. (%): C, 70.57; H, 6.44; N, 10.73. Found (%): C, 70.59; H, 6.42; N, 10.80.

EXAMPLE 75

2-{4-[N-(4,5-di-p-tolylpyrimidin-2-yl)-N-methylamino]butyloxy}acetic acid

In the same manner as in Example 42, except that 2-{4-[N-(4,5-di-p-tolylpyrimidin-2-yl)-N-methylamino]butyloxy}acetic acid tert-butyl ester was used, the desired compound was prepared.

Elemental analysis (for $C_{25}H_{29}N_3O_3$) Calcd. (%): C, 71.58; H, 6.97; N, 10.02. Found (%): C, 71.72; H, 6.96; N, 10.13.

EXAMPLE 76

2-{4-[(5,6-diphenylpyrazin-2-yl)thio]butyloxy}acetic acid

In the same manner as in Example 42, except that 2-{4-[(5,6-diphenylpyrazin-2-yl)thio]butyloxy}acetic acid tert-butyl ester was used in place of 2-{4-[N-(5,6-diphenylpyrazin-2-yl)-N-isopropylamino]butyloxy}acetic acid tert-butyl ester, the desired compound was prepared as a pale yellow crystal having a melting point of 86 to 88° C.

Elemental analysis (for $C_{22}H_{22}N_2O_3S$) Calcd. (%): C, 66.98; H, 5.62; N, 7.10. Found (%): C, 66.81; H, 5.57; N, 7.47.

EXAMPLE 77

5-(carboxymethoxy)-2-{[N-(5,6-diphenylpyrazin-2-yl)-N-methylamino]methyl}-1,2,3,4-tetrahydronaphthalene In the same manner as in Example-42, except that 5-(tert-butoxycarbonylmethoxy)-2-{[N-(5,6-diphenylpyrazin-2-yl)-N-methylamino]methyl}-1,2,3,4-tetrahydronaphthalene was used, the desired compound was prepared as a pale yellow crystal having a melting point of 212 to 213° C.

Elemental analysis (for $C_{30}H_{29}N_3O_3 \cdot 0.2H_2O$) Calcd. (%): C, 74.57; H, 6.13; N, 8.70. Found (%): C, 74.26; H, 6.19; N, 8.41.

EXAMPLE 78

2-{4-[N-(5,6-diphenylpyrazin-2-yl)-N-isopropylamino]butylthio]acetic acid sodium salt Using 2-{4-[N-(5,6-diphenylpyrazin-2-yl)-N-isopropylamino]butylthio}acetic acid methyl ester, carboxylic acid was formed in the same manner as in Example 42 and the resulting carboxylic acid was treated with the same amount (Preceding context, top of column 1:)

Elemental analysis (for $C_{23}H_{25}N_3O_2$) Calcd. (%): C, 73.58; H, 6.71; N, 11.20. Found (%): C, 73.16; H, 6.82; N, 11.01.

of 1N sodium hydroxide solution to obtain the desired compound as a brownish amorphous.

Elemental analysis (for $C_{25}H_{28}N_3O_2SNa \cdot 0.5H_2O$) Calcd. (%): C, 64.36; H, 6.26; N, 9.01. Found (%): C, 64.14; H, 6.05; N, 8.90.

EXAMPLE 79

2-{4-[N-(5,6-diphenylpyrazin-2-yl)-N-isopropylamino]butylsulfinyl}acetic acid

In the same manner as in Example 42, except that 2-{4-[N-(5,6-diphenylpyrazin-2-yl)-N-isopropylamino]butylsulfinyl]acetic acid methyl ester was used, the desired compound was prepared as a yellowish crystal having a melting point of 117 to 120° C. (with decomposition).

Elemental analysis (for $C_{25}H_{29}N_3O_3S$) Calcd. (%): C, 66.49; H, 6.47; N, 9.30. Found (%): C, 66.14; H, 6.47; N, 8.97.

EXAMPLE 80

2-{4-[N-(5,6-diphenylpyrazin-2-yl)-N-isopropylamino]butylsulfonyl}acetic acid

In the same manner as in Example 42, except that 2-{4-[N-(5,6-diphenylpyrazin-2-yl)-N-isopropylamino]butylsulfonyl]acetic acid methyl ester was used, the desired compound was prepared as a yellowish crystal having a melting point of 183 to 185° C.

Elemental analysis (for $C_{25}H_{29}N_3O_4S \cdot 0.2H_2O$) Calcd. (%): C, 63.73; H, 6.29; N, 8.92. Found (%): C, 63.64; H, 6.23; N, 8.66.

EXAMPLE 81

2-[4-(5,6-diphenylpyrazin-2-sulfinyl)butyloxy]acetic acid sodium salt

In the same manner as in Example 47, except that 2-[4-(5,6-diphenylpyrazin-2-sulfinyl)butyloxy]acetic acid tert-butyl ester was used, 2-[4-(5,6-diphenylpyrazin-2-sulfinyl)butyloxy]acetic acid was obtained as a pale yellow oily substance. 125 mg of the resulting oily substance was dissolved in methanol and, after adding 0.30 ml of 1N sodium hydroxide solution, the solvent was evaporated under reduced pressure. The residue was solidified by adding isopropanol and diethyl ether, washed with diethyl ether and then dried to obtain 73 mg of the desired compound as a pale yellow amorphous.

Elemental analysis (for $C_{22}H_{21}N_2O_4SNa \cdot 1.5H_2O \cdot 0.5C_3H_8O$) Calcd. (%): C, 57.66; H, 5.76; N, 5.72. Found (%): C, 58.30; H, 5.10; N, 5.45.

EXAMPLE 82

2-[4-(5,6-diphenylpyrazin-2-sulfonyl)butyloxy]acetic acid

In the same manner as in Example 47, except that 2-[4-(5,6-diphenylpyrazin-2-sulfonyl)butyloxy]acetic acid tert-butyl ester was used, the desired compound was prepared as a pale yellow crystal having a melting point of 123 to 125° C.

Elemental analysis (for $C_{22}H_{22}N_2O_5S$) Calcd. (%): C, 61.96; H, 5.20; N, 6.57. Found (%): C, 61.95; H, 5.25; N, 6.41.

EXAMPLE 83

2-[5-(5,6-diphenylpyrazin-2-yl)pentyloxy]acetic acid sodium salt

In the same manner as in Example 42, except that 2-[5-(5,6-diphenylpyrazin-2-yl)pentyloxy]acetic acid tert-butyl ester was used in place of 2-{4-[N-(5,6-diphenylpyrazin-2-yl)-N-isopropylamino]butyloxy}acetic acid tert-butyl ester, 2-[5-(5,6-diphenylpyrazin-2-yl)pentyloxy]acetic acid was obtained as an oily substance. The resulting oily substance was treated with the same amount of 1N sodium hydroxide solution to obtain the desired compound as a pale brown amorphous.

Elemental analysis (for $C_{23}H_{23}N_2O_3Na \cdot 0.5H_2O$) Calcd. (%): C, 67.80; H, 5.94; N, 6.88. Found (%): C, 68.03; H, 6.22; N, 6.48.

EXAMPLE 84

2-{4-[N-(5,6-diphenylpyrazin-2-yl)-N-isopropylamino]butyloxy}-N-(methylsulfonyl)acetamide Under an argon atmosphere, to a solution of 300 mg of 2-{4-[N-(5,6-diphenylpyrazin-2-yl)-N-isopropylamino]butyloxy}acetic acid obtained in Example 42 in 5 ml of anhydrous tetrahydrofuran, 128 mg of 1,1'-carbonyl diimidazole was added and, after stirring at room temperature for 30 minutes, the mixture was heated at reflux for 30 minutes. After air-cooling to room temperature, 69 mg of methanesulfonamide was added. After stirring for 10 minutes, 0.11 ml of 1,8-diazabicyclo[5.4.0.]-7-undecene was added dropwise. After stirring at room temperature overnight, the reaction solution was diluted with water and then extracted with diethyl ether. The extract was dried over anhydrous magnesium sulfate and the solvent was evaporated under reduced pressure, and then the residue was purified by silica gel column chromatography to obtain 272 mg of the desired compound.

Elemental analysis (for $C_{26}H_{32}N_4O_4S$) Calcd. (%): C, 62.88; H, 6.49; N, 11.28. Found (%): C, 63.06; H, 6.47; N, 10.98.

EXAMPLE 85

2-{4-[N-(5,6-diphenylpyrazin-2-yl)-N-isopropylamino]butyloxy}-N-(p-toluenesulfonyl)acetamide To a solution of 500 mg of 2-{4-[N-(5,6-diphenylpyrazin-2-yl)-N-isopropylamino]butyloxy}acetic acid obtained in Example 42 in 5 ml of anhydrous tetrahydrofuran, 214 mg of 1,1'-carbonyldiimidazole was added and, after stirring at room temperature for 30 minutes, the mixture was heated at reflux for 30 minutes. After air-cooling to room temperature, 206 mg of p-toluenesulfonamide was added. After stirring for 10 minutes, 0.18 ml of 1,8-diazabicyclo[5.4.0.]undec-7-ene was added dropwise. After stirring at room temperature overnight, almost all of the solvent was evaporated under reduced pressure. The residue was combined with water and then neutralized with 1N hydrochloric acid. The reaction solution was extracted with ethyl acetate and dried over anhydrous magnesium sulfate, the solvent was evaporated under reduced pressure. The residue was purified by silica gel column chromatography to obtain 460 mg of the desired compound.

Elemental analysis (for $C_{32}H_{36}N_4O_4S$) Calcd. (%): C, 67.11; H, 6.34; N, 9.78. Found (%): C, 67.04; H, 6.37; N, 9.65.

EXAMPLE 86

2-{4-[N-(5,6-diphenylpyrazin-2-yl)-N-isopropylamino]butyloxy}-N-(isopropylsulfonyl)acetamide In the same manner as in Example 85, except that isopropylsulfonamide was used in place of p-toluenesulfonamide, the desired compound was prepared.

Elemental analysis (for $C_{28}H_{36}N_4O_4S$) Calcd. (%): C, 64.10; H, 6.92; N, 10.68. Found (%): C, 64.19; H, 6.97; N, 10.62.

EXAMPLE 87

2-{4-[N-(5,6-diphenylpyrazin-2-yl)-N-isopropylamino]butyloxy}-N-(trifluoromethanesulfonyl)acetamide In the same manner as in Example 85, except that trifluoromethanesulfonamide was used in place of p-toluenesulfonamide, the desired compound was prepared.

Elemental analysis (for $C_{26}H_{29}F_3N_4O_4S.1.2H_2O$) Calcd. (%): C, 54.57; H, 5.53; N, 9.79. Found (%): C, 54.41; H, 5.22; N, 9.45.

EXAMPLE 88

2-{4-[N-(5,6-diphenylpyrazin-2-yl)-N-isopropylamino]butyloxy}-N-(o-toluenesulfonyl)acetamide In the same manner as in Example 85, except that o-toluenesulfonamide was used in place of p-toluenesulfonamide, the desired compound was prepared.

Elemental analysis (for $C_{32}H_{36}N_4O_4S$) Calcd. (%): C, 67.11; H, 6.34; N, 9.78. Found (%): C, 66.95; H, 6.32; N, 9.59.

EXAMPLE 89

N-(benzenesulfonyl)-2-{4-[N-(5,6-diphenylpyrazin-2-yl)-N-isopropylamino]butyloxy}acetamide In the same manner as in Example 85, except that benzenesulfonamide was used in place of p-toluenesulfonamide, the desired compound was prepared.

Elemental analysis (for $C_{31}H_{34}N_4O_4S$) Calcd. (%): C, 66.64; H, 6.13; N, 10.03. Found (%): C, 66.66; H, 6.12; N, 9.99.

EXAMPLE 90

N-(4-chlorobenzenesulfonyl)-2-{4-[N-(5,6-diphenylpyrazin-2-yl)-N-isopropylamino]butyloxy}acetamide In the same manner as in Example 85, except that 4-chlorobenzenesulfonamide was used in place of p-toluenesulfonamide, the desired compound was prepared.

Elemental analysis (for $C_{31}H_{33}ClN_4O_4S$) Calcd. (%): C, 62.77; H, 5.61; N, 9.45. Found (%): C, 62.99; H, 5.58; N, 9.50.

EXAMPLE 91

2-{4-[N-(5,6-diphenylpyrazin-2-yl)-N-isopropylamino]butyloxy}-N-(4-methoxybenzenesulfonyl)acetamide In the same manner as in Example 85, except that 4-methoxybenzenesulfonamide was used in place of p-toluenesulfonamide, the desired compound was prepared.

Elemental analysis (for $C_{32}H_{36}N_4O_5S.0.6H_2O$) Calcd. (%): C, 64.11; H, 6.25; N, 9.35. Found (%): C, 63.86; H, 5.95; N, 9.39.

EXAMPLE 92

2-{4-[N-(5,6-diphenylpyrazin-2-yl)-N-isopropylamino]butyloxy}-N-(4-fluorobenzenesulfonyl)acetamide In the same manner as in Example 85, except that 4-fluorobenzenesulfonamide was used in place of p-toluenesulfonamide, the desired compound was prepared.

Elemental analysis (for $C_{31}H_{33}FN_4O_4S$) Calcd. (%): C, 64.56; H, 5.77; N, 9.72. Found (%): C, 64.36; H, 5.88; N, 9.56.

EXAMPLE 93

2-{4-[N-(5,6-diphenylpyrazin-2-yl)-N-isopropylamino]butyloxy}-N-(2-thiophenesulfonyl)acetamide In the same manner as in Example 85, except that 2-thiophenesulfonamide was used in place of p-toluenesulfonamide, the desired compound was prepared.

Elemental analysis (for $C_{29}H_{32}N_4O_4S_2$) Calcd. (%): C, 61.68; H, 5.71; N, 9.92. Found (%): C, 61.70; H, 5.78; N, 9.76.

EXAMPLE 94

N-(aminosulfonyl)-2-{4-[N-(5,6-diphenylpyrazin-2-yl)-N-isopropylamino]butyloxy}acetamide In the same manner as in Example 85, except that sulfamide was used in place of p-toluenesulfonamide, the desired compound was prepared.

Elemental analysis (for $C_{25}H_{31}N_5O_4S$) Calcd. (%): C, 60.34; H, 6.28; N, 14.07. Found (%): C, 60.09; H, 6.27; N, 14.04.

EXAMPLE 95

N-(N,N-dimethylaminosulfonyl)-2-{4-[N-(5,6-diphenylpyrazin-2-yl)-N-isopropylamino]butyloxy}acetamide In the same manner as in Example 85, except that N,N-dimethylsulfamide was used in place of p-toluenesulfonamide, the desired compound was prepared.

Elemental analysis (for $C_{27}H_{35}N_5O_4S$) Calcd. (%): C, 61.69; H, 6.71; N, 13.32. Found (%): C, 61.60; H, 6.64; N, 13.24.

EXAMPLE 96

2-{4-[N-(5,6-diphenylpyrazin-2-yl)-N-isopropylamino]butyloxy}-N-(morpholin-4-ylsulfonyl)acetamide In the same manner as in Example 85, except that morpholin-4-ylsulfonamide was used in place of p-toluenesulfonamide, the desired compound was prepared.

Elemental analysis (for $C_{29}H_{37}N_5O_5S$) Calcd. (%): C, 61.36; H, 6.57; N, 12.34. Found (%): C, 61.11; H, 6.59; N, 12.03.

EXAMPLE 97

2-{4-[N-(5,6-diphenylpyrazin-2-yl)-N-isopropylamino]butyloxy}-N-(pyrrolidin-1-ylsulfonyl)acetamide In the same manner as in Example 85, except that pyrrolidin-1-ylsulfonamide was used in place of p-toluenesulfonamide, the desired compound was prepared.

Elemental analysis (for $C_{29}H_{37}N_5O_4S$) Calcd. (%): C, 63.13; H, 6.76; N, 12.69. Found (%): C, 63.11; H, 6.78; N, 12.49.

EXAMPLE 98

[2-{4-[N-(5,6-diphenylpyrazin-2-yl)-N-isopropylamino]butyloxy}acetyl]sulfamic acid phenyl ester In the same manner as in Example 85, except that sulfamic acid phenyl ester was used in place of p-toluenesulfonamide, the desired compound was prepared.

Elemental analysis (for $C_{31}H_{34}N_4O_5S$) Calcd. (%): C, 64.79; H, 5.96; N, 9.75. Found (%): C, 64.93; H, 6.01; N, 9.59.

EXAMPLE 99

2-{4-[N-(5,6-diphenylpyrazin-2-yl)-N-isopropylamino]butyloxy}acetamide 1.50 g of 2-{4-[N-(5,6-diphenylpyrazin-2-yl)-N-isopropylamino]butyloxy}acetic acid was dissolved in 20 ml of anhydrous tetrahydrofuran and 0.500 ml of triethylamine was added and then 0.376 ml of ethyl chlorocarbonate was added while stirring under ice cooling. After stirring under ice cooling for 45 minutes, a solution of saturated ammonia in 20 ml of tetrahydrofuran was added, followed by stirring for one hour. After removing an ice bath and stirring at room temperature for 18 hours, almost all of the solvent was evaporated. The residue was combined with water and then extracted with ethyl acetate. The extract was washed in turn with an aqueous saturated sodium hydrogen carbonate solution, 1N sodium hydroxide solution and water and dried over anhydrous magnesium sulfate, and then the solvent was evaporated under reduced pressure. The residue was washed with diethyl ether and then dried under reduced pressure to obtain 1.19 g of the desired product.

Elemental analysis (for $C_{25}H_{30}N_4O_2$) Calcd. (%): C, 71.74; H, 7.22; N, 13.39. Found (%): C, 71.79; H, 7.30; N, 13.34.

EXAMPLE 100

N-[2-{4-[N-(5,6-diphenylpyrazin-2-yl)-N-isopropylamino]butyloxy}acetyl]sulfamic acid sodium salt Under an argon atmosphere, a solution of 1.443 g of 2-picoline in 1.7 ml of 1,2-dichloroethane was cooled to −10° C. A solution of chlorosulfonic acid in 3.5 ml of 1,2-dichloroethane was added dropwise at 0° C. or lower and, after stirring for 15 minutes, 712 mg of 2-[4-[N-(5,6-diphenylpyrazin-2-yl)-N-isopropylamino]butyloxy]acetamide was added. The reaction solution was heated to 75° C. and air-cooled to room temperature after stirring for 2 hours. The reaction solution was diluted with dichloromethane and then washed in turn with an aqueous 0.6M sodium hydrogen sulfate and water. The reaction solution was dried over anhydrous magnesium sulfate and the solvent was evaporated under reduced pressure. The residue was purified by silica gel column chromatography (chloroform-methanol) to obtain 798 mg of N-[2-{4-[N-(5,6-diphenylpyrazin-2-yl)-N-isopropylamino]butyloxy}acetyl]sulfamic acid.

Elemental analysis (for $C_{25}H_{30}N_4O_5SN.0.5CHCl_3$) Calcd. (%): C, 54.86; H, 5.51; N, 10.04. Found (%): C, 54.72; H, 5.51; N, 9.84.

EXAMPLE 101

100 mg of the compound obtained in Example 100 was dissolved in 1 ml of a mixed solution of ethanol and water (1:1) and 0.200 ml of a 1N sodium hydroxide solution was added. After the solvent was evaporated, the mixture was solidified with a mixed solution of ethanol and methanol and the solid was collected by filtration and then dried under reduced pressure to obtain 49 mg of the titled compound as a colorless solid.

Elemental analysis (for $C_{25}H_{29}N_4O_5SNa.1.5H_2O$) Calcd. (%): C, 54.83; H, 5.89; N, 10.23. Found (%): C, 54.39; H, 5.48; N, 10.07.

TEST EXAMPLE 1

Human Platelet Aggregation Inhibition Test

Blood collected from healthy human volunteers into aqueous trisodium citrate solution was centrifuged at 200×g for 10 minutes and the upper layer was recovered to obtain platelet-rich plasma (PRP). The residual blood containing trisodium citrate added therein was centrifuged at 1500×g for 10 minutes and the supernatant was collected as platelet-poor plasma (PPP). The number of platelets in the PRP was adjusted to about 300,000/μl by PPP. Platelet aggregation was measured by an aggregometer. 180 μl of PRP was added to cuvettes and incubated at 37° C. for one minute, and then 10 μl of test compound solution (prepared by dissolving a test compound with a 1.5-fold mole of a sodium hydroxide solution and diluting with water) was added and the mixture was further incubated for 2 minutes. Then, 10 μl of aqueous adenosine diphosphate (ADP) solution was added to adjust the final concentration as $1×10^{-5}$ M and platelet aggregation was induced and observed for 7 minutes. Inhibition percentage of aggregation was calculated from the percentage of aggregation upon the addition of the test compound to the percentage of aggregation upon the addition of water in place of the test compound solution (control). The test compound was added to adjust the final concentration to the range from $10^{-8}$ to $10^{-4}$ M, and $IC_{50}$ values were determined by inhibition percentage of aggregation at each concentration. The results are shown in Table 1.

It is apparent that the compounds of the present invention markedly inhibit platelet aggregation in human PRP.

TABLE 1

Inhibition of human platelet aggregation

| Test compounds | $IC_{50}$ (μM) |
| --- | --- |
| Example 42 | 0.2 |
| Example 43 | 0.8 |
| Example 46 | 0.5 |
| Example 48 | 0.4 |
| Example 64 | 0.2 |
| Example 65 | 0.3 |
| Example 73 | 0.2 |
| Example 74 | 0.8 |
| Example 75 | 0.2 |
| Example 78 | 0.3 |

TEST EXAMPLE 2

$^3$H-Iloprost Binding Inhibition Test to Human Platelet Membrane

Human platelet membrane of 100 μg protein was suspended in 200 μl of 50 mM Tris-HCl buffer (pH7.4) containing 10 mM MgCl$_2$, 1 mM EGTA and 5 nM $^3$H-Iloprost and then incubated at 37° C. for 10 minutes with 5 μM non-labeled Iloprost or the compound (1 μM) of Example 64. The platelet membrane was collected on a glass filter and its radioactivity was measured after washing four times with 50 mM Tris-HCl buffer. The compound (1 μM) of Example 64 inhibited binding of $^3$H-Iloprost by 85%.

TEST EXAMPLE 3

Increase in cAMP in Human Platelet

500 μl of washed human platelet suspension (2×10$^8$/ml) containing each concentration of the compound of Example 64 was incubated at 37° C. for 10 minutes and sonicated after adding aqueous 1 M perchloric acid solution. After the sonicated solution was centrifuged and the supernatant was neutralized with an aqueous 1 M potassium hydrogen carbonate solution, centrifuged again and the supernatant was recovered. The concentration of cAMP in the supernatant was determined by an ELISA method. As shown in Table 2, the amount of cAMP in platelets was increased by the compound of Example 64 in a concentration-dependent mannar.

TABLE 2

Increase in cAMP in human platelet.

| Concentration of Example 64 (nM) | cAMP (pmol/10$^8$ platelet) |
| --- | --- |
| 10 | 3.7 |
| 30 | 6.4 |
| 100 | 20.7 |
| 300 | 28.5 |
| 1000 | 39.4 |
| 3000 | 35.3 |

As is apparent from Test Examples 1 to 3, the compounds of the present invention inhibit platelet aggregation on the basis of their PGI$_2$ receptor antagonistic activity.

TEST EXAMPLE 4

Singl-Dose Toxicity Test in Mice

The compound of Example 42 was orally administered to mice (including three mice in a group) at a dose of 10, 30 or 100 mg/kg. As a result, there were no deaths.

The compound of Example 64 was orally administered to mice (including five mice in a group) at a dose of 300 mg/kg. As a result, there were no deaths.

TEST EXAMPLE 5

Ex Vivo Platelet Aggregation Inhibition Test in Monkeys

Method

The compound of Example 84 was orally administered to two cynomolgus monkeys (*Macaca fascicularis*, male, aged 3 to 5) at a dose of 0.3 or 1 mg/kg. Before the administration or 2, 4 and 8 hours after the administration, blood (each 4.5 ml) was collected using an injection cylinder containing aqueous 3.8% citric acid solution in the amount of 1/10 of the volume of blood to be collected. Blood containing citric acid solution was centrifuged at 200×g for 10 minutes and the upper layer was collected as PRP. Furthermore, the residual blood was centrifuged at 1500×g for 10 minutes and the supernatant was collected as PPP. 190 μl of PRP was added to a cuvette and incubated at 37° C. for one minute, and then 10 μl of ADP solution (5 to 30 μM) was added to induce platelet aggregation. The percentage of platelet aggregation was measured by an aggregometer (PM8C, Mebanix, Tokyo) using PPP as the blank and inhibition percentage of platelet aggregation was determined by comparing the percentage of aggregation before administration of the compound with the percentage of aggregation after administration of the compound according to the following equation. The results are shown in Table 3.

Inhibition percentage of Platelet Aggregation (%)=100−(The percentage of Aggregation after administration of compound)/(The percentage of Aggregation before administration of compound)×100

TABLE 3

Inhibition percentage of platelet aggregation in monkeys (%)

| Time after administration (h) | Dose of Example 84 (mg/kg) | |
| --- | --- | --- |
| | 0.3 | 1 |
| 2 | 28 | 63 |
| 4 | 34 | 40 |
| 8 | 19 | 52 |

It is apparent that the compound of Example 84 inhibits platelet aggregation persistently in a dose-dependent manner after 2 to 8 hours have passed since the administration, and drug efficacy persists for a long time.

FORMULATION EXAMPLE 1

Tablets (tablets for internal use)

Formulation weighing 200 mg per tablet

| | |
| --- | --- |
| Compound of Example 40 | 20 mg |
| Corn starch | 88 mg |
| Crystalline cellulose | 80 mg |
| Calcium Carboxymethylcellulose | 10 mg |
| Light anhydrous silicic acid | 1 mg |
| Magnesium stearate | 1 mg |

Mixed powders prepared according to the above formulation were compressed to give tablets for internal use.

FORMULATION EXAMPLE 2

Tablets (tablets for internal use)

Formulation weighting 120 mg per tablet

| | |
| --- | --- |
| Compound of Example 51 | 1 mg |
| Lactose | 60 mg |

-continued

| | |
|---|---|
| Corn starch | 30 mg |
| Crystalline cellulose | 20 mg |
| Hydroxypropylcellulose | 7 mg |
| Magnesium stearate | 2 mg |

Mixed powders prepared according to the above formulation were compressed to give tablets for internal use.

FORMULATION EXAMPLE 3

Tablets (tablets for internal use)

Formulation weighing 180 mg per tablet

| | |
|---|---|
| Compound of Example 63 | 100 mg |
| Lactose | 45 mg |
| Corn starch | 20 mg |
| Low substituted hydroxypropylcellulose | 9 mg |
| Polyvinyl alcohol (partially saponified) | 5 mg |
| Magnesium stearate | 1 mg |

Mixed powders prepared according to the above formulation were compressed to give tablets for internal use.

INDUSTRIAL APPLICABILITY

The compound of the present invention is useful as a therapeutic agent such as platelet coagulation inhibitor because it has a PGI$_2$ receptor antagonistic activity and also has low toxicity.

What is claimed is:

1. A pharmaceutical composition comprising a heterocyclic compound represented by the following general formula (1) or a salt thereof as an active ingredient:

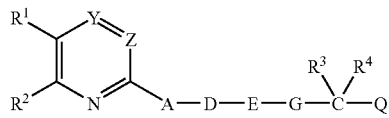

wherein $R^1$ and $R^2$ are the same or different and each represents an optionally substituted aryl, and the substituents are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro, Y represents N or N→O, Z represents $CR^6$; and $R^6$ represents hydrogen, alkyl, or halogen, A represents $NR^7$ or SO, and $R^7$ represents hydrogen, alkyl, alkenyl or cycloalkyl, D represents alkylene or alkenylene which are optionally substituted with hydroxy, or A and D are combined with each other to form a divalent group represented by the following formula (2):

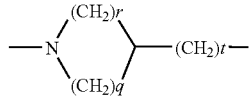

r represents an integer of 0 to 2, q represents an integer of 2 to 3, and t represents an integer of 0 to 4, E represents phenylene or single bond, or D and E are combined with each other to form a divalent group represented by the following formula (3):

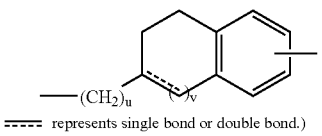

( ===== represents single bond or double bond.)

u represents an integer of 0 to 2, and v represents 0 or 1,

G represents O, S, SO, SO$_2$, or $C(R^8)(R^9)$, and $R^8$ and $R^9$ are the same or different and each represents hydrogen or alkyl, $R^3$ and $R^4$ are the same or different and each represents hydrogen or alkyl, Q represents carboxy, alkoxycarbonyl, tetrazolyl, carbamoyl, monoalkylcarbamoyl, dialkylcarbamoyl, or a group represented by the following formula (22):

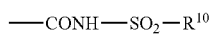

$R^{10}$ represents amino, monoalkylamino, dialkylamino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro;

and a pharmaceutically acceptable carrier.

2. The pharmaceutical composition according to claim 1, wherein, in the formula (1), $R^1$ and $R^2$ are the same or different and each represents optionally substituted phenyl, and the substituents are the same or different and 1 to 3 substituents are selected from the group consisting of halogen, alkyl and alkoxy, Y and Z correspond to either of the following cases (1) and (2):

(1) Y is N, and Z is CH, and (2) Y is N→O, and Z is CH,

A represents $NR^7$, and $R^7$ represents hydrogen, alkyl, or cycloalkyl,

D represents alkylene or alkenylene,

E represents single bond,

G represents O, S, SO, SO$_2$, or $C(R^8)(R^9)$, and $R^8$ and $R^9$ each represents hydrogen, $R^3$ and $R^4$ are the same or different and each represents hydrogen or alkyl, and Q represents carboxy, alkoxycarbonyl, tetrazolyl, or a group represented by the formula (22), and $R^{10}$ represents amino, monoalkylamino, dialkylamino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro.

3. The pharmaceutical composition according to claim 1, wherein, in the formula (1), $R^1$ and $R^2$ are the same or different and each represents optionally substituted phenyl, and the substituents are the same or different and 1 to 3 substituents are selected from the group consisting of halogen, alkyl and alkoxy, Y is N, and Z is CH,
A represents $NR^7$, and $R^7$ represents hydrogen or alkyl,
D represents alkylene,
E represents single bond,
G represents O,
$R^3$ and $R^4$ are the same or different and each represents hydrogen or alkyl,
Q represents carboxy, tetrazolyl, or a group represented by the formula (22), and $R^{10}$ represents amino, monoalkylamino, dialkylamino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro.

4. The pharmaceutical composition according to claim 1, wherein, in the formula (1), $R^1$ and $R^2$ are the same or different and each represents optionally substituted phenyl, and the substituents are the same or different and 1 to 3 substituents are selected from the group consisting of halogen, alkyl and alkoxy, Y represents N, and Z represents CH,
A represents $NR^7$, and $R^7$ represents alkyl,
D represents alkylene,
E represents single bond,
G represents O,
$R^3$ and $R^4$ are the same or different and each represents hydrogen or alkyl, and
Q represents carboxy or a group represented by the formula (22), and $R^{10}$ represents amino monoalkylamino, dialkylamino, hydroxy, optionally substituted alkyl, optionally substituted aryl, optionally substituted aryloxy or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro.

5. The pharmaceutical composition according to claim 1, wherein the hetero cyclic compound is selected from the group consisting of the following compounds (1) to (27):

(1) 2-{4-[N-(5,6-di-p-tolylpyrazin-2-yl)-N-methylamino]butyloxy}acetic acid,
(2) 2-{4-[N-(5,6-diphenylpyrazin-2-yl)-N-methylamino]butyloxy}acetic acid,
(3) 2-{4-[N-(5,6-diphenylpyrazin-2-yl)-N-isopropylamino]butyloxy}acetic acid,
(4) 2-{4-[N-(5,6-di-p-tolylpyrazin-2-yl)-N-isopropylamino]butyloxy}acetic acid,
(5) 2,3-diphenyl-5-{N-[4-(carboxymethoxy)butyl]-N-methylamino}pyrazine 1-oxide,
(6) 7-[N-(5,6-diphenylpyrazin-2-yl)-N-methylamino]heptanoic acid,
(7) 2-{4-[N-(5,6-diphenylpyrazin-2-yl)-N-isopropylamino]butylthio}acetic acid,
(8) 2-{4-[N-(5,6-diphenylpyrazin-2-yl)-N-methylamino]-(Z)-2-buten-1-yloxy}acetic acid,
(9) 2-{4-[N-(5,6-diphenylpyrazin-2-yl)-N-ethylamino]butyloxy}acetic acid,
(10) 2-{4-[N-(5,6-diphenylpyrazin-2-yl)-N-isopropylamino]butylsulfinyl}acetic acid,
(11) 2-{4-[N-(5,6-diphenylpyrazin-2-yl)-N-isopropylamino]butyloxy}-N-(p-toluenesulfonyl)acetamide,
(12) 2-{4-[N-(5,6-diphenylpyrazin-2-yl)-N-isopropylamino]butyloxy}-N-(isopropylsulfonyl)acetamide,
(13) 2-{4-[N-(5,6-diphenylpyrazin-2-yl)-N-isopropylamino]butyloxy}-N-(trifluoromethanesulfonyl)acetamide,
(14) 2-{4-[N-(5,6-diphenylpyrazin-2-yl)-N-isopropylamino]butyloxy}-N-(o-toluenesulfonyl)acetamide,
(15) N-(benzenesulfonyl)-2-{4-[N-(5,6-diphenylpyrazin-2-yl)-N-isopropylamino]butyloxy}acetamide,
(16) N-(4-chlorobenzenesulfonyl)-2-{4-[N-(5,6-diphenylpyrazin-2-yl)-N-isopropylamino]butyloxy}acetamide,
(17) 2-{4-[N-(5,6-diphenylpyrazin-2-yl)-N-isopropylamino]butyloxy}-N-(4-methoxybenzenesulfonyl)acetamide,
(18) 2-{4-[N-(5,6-diphenylpyrazin-2-yl)-N-isopropylamino]butyloxy}-N-(4-fluorobenzenesulfonyl)acetamide,
(19) 2-{4-[N-(5,6-diphenylpyrazin-2-yl)-N-isopropylamino]butyloxy}-N-(2-thiophenesulfonyl)acetamide,
(20) N-(aminosulfonyl)-2-{4-[N-(5,6-diphenylpyrazin-2-yl)-N-isopropylamino]butyloxy}acetamide,
(21) N-(N,N-dimethylaminosulfonyl)-2-{4-[N-(5,6-diphenylpyrazin-2-yl)-N-isopropylamino]butyloxy}acetamide,
(22) 2-{4-[N-(5,6-diphenylpyrazin-2-yl)-N-isopropylamino]butyloxy}-N-(morpholin-4-ylsulfonyl)acetamide,
(23) 2-{4-[N-(5,6-diphenylpyrazin-2-yl)-N-isopropylamino]butyloxy}-N-(pyrrolidin-1-ylsulfonyl)acetamide,
(24) N-[2-{4-[N-(5,6-diphenylpyrazin-2-yl)-N-isopropylamino]butyloxy}acetyl]sulfamic acid phenyl ester,
(25) N-[2-{4-[N-(5,6-diphenylpyrazin-2-yl)-N-isopropylamino]butyloxy}acetyl]sulfamic acid,
(26) N-[2-{4-[N-(5,6-diphenylpyrazin-2-yl)-N-isopropylamino]butyloxy}acetyl]sulfamic acid sodium salt, and
(27) 2-{4-[N-(5,6-diphenylpyrazin-2-yl)-N-isopropylamino]butyloxy}-N-(methylsulfonyl)acetamide.

6. A method of inhibiting platelet aggregation, comprising administering to a subject in need thereof an effective amount of a pharmaceutical composition according to claim 1.

7. A method of treating arteriosclerosis obliterans, comprising administering to a subject in need thereof an effective amount of a pharmaceutical composition according to claim 1.

8. A method of treating intermittent claudication, comprising administering to a subject in need thereof an effective amount of a pharmaceutical composition according to claim 1.

9. A method of treating peripheral arterial embolism, comprising administering to a subject in need thereof an effective amount of a pharmaceutical composition according to claim 1.

10. A heterocyclic compound represented by the following general formula (1z) or a salt thereof:

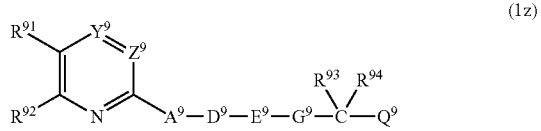

(1z)

wherein:
$R^{91}$ and $R^{92}$ are the same or different and each represents optionally substituted aryl, and the substituents are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro, $Y^9$ represents N or N→O, $Z^9$ represents $CR^{96}$, and $R^{96}$ represents hydrogen, alkyl, or halogen, $A^9$ represents $NR^{97}$ or SO, and $R^{97}$ represents hydrogen, alkyl, alkenyl, or cycloalkyl, $D^9$ represents alkylene or alkenylene which are optionally substituted with hydroxy, or $A^9$ and $D^9$ are combined with each other to form a divalent group represented by the following formula (2z):

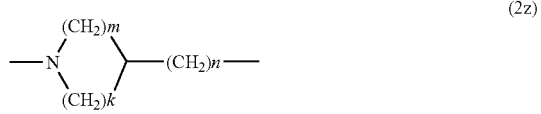

(2z)

m represents an integer of 0 to 2, k represents an integer of 2 to 3, and n represents an integer of 0 to 4, $E^9$ represents phenylene or single bond, or $D^9$ and $E^9$ are combined with each other to form a divalent group represented by the following formula (3z):

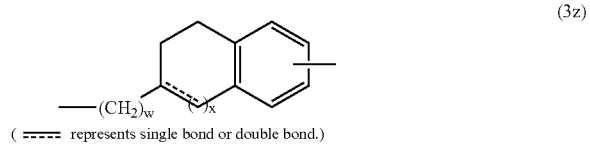

(3z)

( ≈≈≈ represents single bond or double bond.)

w represents an integer of 0 to 2, and x represents 0 or 1,
$G^9$ represents O, S, SO, $SO_2$, or $C(R^{98})(R^{99})$, and $R^{98}$ and $R^{99}$ are the same or different and each represents hydrogen or alkyl, $R^{93}$ and $R^{94}$ are the same or different and each represents hydrogen or alkyl, $Q^9$ represents carboxy, alkoxycarbonyl, tetrazolyl, carbamoyl, monoalkylcarbamoyl, dialkylcarbamoyl, or a group represented by the following formula (22z):

(22z)

$R^{910}$ represents amino, monoalkylamino, dialkylaxuino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro.

11. The heterocyclic compound according to claim 10, wherein, in the formula (1z), substituents correspond to the following case:

$R^{91}$ and $R^{92}$ are the same or different and each represents optionally substituted phenyl, and the substituents are the same or different and 1 to 3 substituents are selected from the group consisting of halogen, alkyl and. alkoxy, $Y^9$ and $Z^9$ correspond to either of the following cases (1) and (2):
(1) $Y^9$ is N, and $Z^9$ is CH, and
(2) $Y^9$ is N→O, and $Z^9$ is CH, $A^9$ represents $NR^{97}$, and $R^{97}$ represents hydrogen, alkyl, or cycloalkyl, $D^9$ represents alkylene, $E^9$ single bond, $G^9$ represents O, S. SO, $SO_2$, or $C(R^{98})(R^{99})$, and $R^{98}$ and $R^{99}$ each represents hydrogen, $R^{93}$ and $R^{94}$ are the same or different and each represents hydrogen or alkyl, and $Q^9$ represents carboxy, alkoxycarbonyl, tetrazolyl, or a group represented by the formula (22z), $R^{910}$ represents amino, monoalkylarnino, dialkylamino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro.

12. The heterocyclic compound according to claim 10, wherein, in the formula (1z), $R^{91}$ and $R^{92}$ are the same or different and each represents optionally substituted phenyl, and the substituents are the same or different and 1 to 3 substituents are selected from the group consisting of halogen, alkyl and alkoxy, $Y^9$ represents N, $Z^9$ represents CH, $A^9$ represents $NR^{97}$, and $R^{97}$ represents hydrogen or alkyl, $D^9$ represents alkylene, $E^9$ represents single bond, $G^9$ represents O, $R^{93}$ and $R^{94}$ are the same or different and each represents hydrogen or alkyl, $Q^9$ represents carboxy, tetrazolyl, or a group represented by the formula (22z), $R^{910}$ represents amino, monoalkylamino, dialkylamino, hydroxy, optionally substituted alkyl, optionally substituted aryl, optionally substituted aryloxy, or optionally substituted heterocyclic group, and the substituents of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro.

13. The heterocyclic compound according to claim 10, wherein $R^{91}$ and $R^{92}$ are the same or different and each represents optionally substituted phenyl, and the substituents are the same or different and 1 to 3 substituents are selected from the group consisting of halogen, alkyl and alkoxy, $Y^9$ represents N, and $Z^9$ represents CH, $A^9$ represents $NR^{97}$, and $R^{97}$ represents alkyl, $D^9$ represents alkylene, $E^9$ single bond, $G^9$ represents O, $R^{93}$ and $R^{94}$ are the same or different and each represents hydrogen or alkyl, $Q^9$ represents carboxy or a group represented by the formula (22z), $R^{910}$ represents amino, monoalkylamino, dialkylamino, hydroxy, optionally substituted alkyl, optionally substituted aryl, optionaiiy substituted aryloxy, or optionally substituted heterocyclic group, and the substitunets of alkyl, aryl, aryloxy or heterocyclic group are the same or different and 1 to 3 substituents are selected from the group consisting of halogen, alkyl, haloalkyl, arylalkyl, alkoxy, alkylthio, alkoxyalkyl, alkylsulfonyl, hydroxy, amino, monoalkylamino, dialkylamino, carboxy, cyano and nitro.

14. The heterocyclic compound according to claim 10, wherein the heterocyclic compound is selected from the following compounds (1) to (27):

(1) 2-{4-[N-(5,6-di-p-tolylpyrazin-2-yl)-N-methylamino]butyloxy}acetic acid, (2) 2-{4-[N-(5,6-diphenylpyrazin-2-yl)-N-methylamino]butyloxy}acetic acid, (3) 2-{4-[N-(5,6-diphenylpyrazin-2-yl)-N-isopropylamino]butyloxy}acetic acid, (4) 2-{4-[N-(5,6-di-p-tolylpyrazin-2-yl)-N-isopropylamino]butyloxy}acetic acid, (5) 2,3-diphenyl-5-{N-[4-(carboxymethoxy)butyl]-N-methylamino}pyrazine 1-oxide, (6) 7-[N-(5,6-diphenylpyrazin-2-yl)-N-methylamino]heptanoic acid, (7) 2-{4-[N-(5,6-diphenylpyrazin-2-yl)-N-isopropylamino]butylthio}acetic acid, (8) 2-{4-[N-(5,6-diphenylpyrazin-2-yl)-N-methylamino]-(Z)-2-buten-1-yloxy}acetic acid, (9) 2-{4-[N-(5,6-diphenylpyrazin-2-yl)-N-ethylamino]butyloxy}acetic acid,

(10) 2-{4-[N-(5,6-diphenylpyrazin-2-yl)-N-isopropylamino]butylsulfinyl}acetic acid,

(11) 2-{4-[N-(5,6-diphenylpyrazin-2-yl)-N-isopropylamino]butyloxy}-N-(p-toluenesulfonyl)acetamide,

(12) 2-{4-[N-(5,6-diphenylpyrazin-2-yl)-N-isopropylamino]butyloxy}-N-(isopropylsulfonyl)acetamide,

(13) 2-{4-[N-(5,6-diphenylpyrazin-2-yl)-N-isopropylamino]butyloxy}-N-(trifluoromethanesulfonyl)acetamide,

(14) 2-{4-[N-(5,6-diphenylpyrazin-2-yl)-N-isopropylamino]butyloxy}-N-(o-toluenesulfonyl)acetamide,

(15) N-(benzenesulfonyl)-2-{4-[N-(5,6-diphenylpyrazin-2-yl)-N-isopropylamino]butyloxy}acetamide,

(16) N-(4-chlorobenzenesulfonyl)-2-{4-[N-(5,6-diphenylpyrazin-2-yl)-N-isopropylamino]butyloxy}acetamide,

(17) 2-{4-[N-(5,6-diphenylpyrazin-2-yl)-N-isopropylamino]butyloxy}-N-(4-methoxybenzenesulfonyl)acetamide,

(18) 2-{4-[N-(5,6-diphenylpyrazin-2-yl)-N-isopropylamino]butyloxy}-N-(4-fluorobenzenesulfonyl)acetamide,

(19) 2-{4-[N-(5,6-diphenylpyrazin-2-yl)-N-isopropylamino]butyloxy}-N-(2-thiophenesulfonyl)acetamide,

(20) N-(aminosulfonyl)-2-{4-[N-(5,6-diphenylpyrazin-2-yl)-N-isopropylamino]butyloxy}acetamide,

(21) N-(N,N-dimethylaminosulfonyl)-2-{4-[N-(5,6-diphenylpyrazin-2-yl)-N-isopropylamino]butyloxy}acetamide,

(22) 2-{4-[N-(5,6-diphenylpyrazin-2-yl)-N-isopropylamino]butyloxy}-N-(morpholin-4-ylsulfonyl)acetamide,

(23) 2-{4-[N-(5,6-diphenylpyrazin-2-yl)-N-isopropylamino]butyloxy}-N-(pyrrolidin-1-ylsulfonyl)acetamide,

(24) N-[2-{4-[N-(5,6-diphenylpyrazin-2-yl)-N-isopropylamino]butyloxy}acetyl]sulfamic acid phenyl ester,

(25) N-[2-{4-[N-(5,6-diphenylpyrazin-2-yl)-N-isopropylamino]butyloxy}acetyl]sulfamic acid,

(26) N-[2-{4-[N-(5,6-diphenylpyrazin-2-yl)-N-isopropylamino]butyloxy}acetyl]sulfamic acid sodium salt, and

(27) 2-{4-[N-(5,6-diphenylpyrazin-2-yl)-N-isopropylamino]butyloxy}-N-(methylsulfonyl)acetamide.

15. A method of treating pulmonary hypertension, comprising administering to a subject in need thereof an effective amount of a pharmaceutical composition according to claim 1.

* * * * *

UNITED STATES PATENT AND TRADEMARK OFFICE

(12)        CERTIFICATE EXTENDING PATENT TERM
UNDER 35 U.S.C. 156

(68) PATENT NO. : 7,205,302

(45) ISSUED : April 17, 2007

(75) INVENTOR : Tetsuo Asaki et al.

(73) PATENT OWNER : Nippon Shinyaku Co., Ltd.

(95) PRODUCT : UPTRAVI® (selexipag)

This is to certify that an application under 35 U.S.C. 156 has been filed in the United States Patent and Trademark Office, requesting extension of the term of U.S. Patent No. 7,205,302 based upon the regulatory review of the product UPTRAVI® (selexipag) by the Food and Drug Administration. According to United States Patent and Trademark Office records, the original expiration date of the patent as of the date of issuance of this certificate is April 4, 2023. Because it appears that the requirements of the law have been met, this certificate extends the term of the patent for the period of

(94)                        1,306 days subject to the payment of maintenance fees as provided by law, with all rights pertaining thereto as provided by 35 U.S.C. 156.

I have caused the seal of the United States Patent and Trademark Office to be affixed this 12th day of November 2021.

Drew Hirshfeld
Commissioner for Patents, Performing the Functions and Duties of the Under Secretary of Commerce for Intellectual Property and Director of the United States Patent and Trademark Office